US008266878B2

(12) United States Patent
Luciano, Jr. et al.

(10) Patent No.: US 8,266,878 B2
(45) Date of Patent: Sep. 18, 2012

(54) SYSTEM AND METHOD FOR VERIFYING AND ASSEMBLING A MULTIPLE PRESCRIPTION PACKAGE

(75) Inventors: Robert A. Luciano, Jr., Reno, NV (US); Leslie Baker, Reno, NV (US); Larry Luciano, Somerville, NJ (US)

(73) Assignee: Edge Medical Properties, LLC, Reno, NV (US)

( * ) Notice: Subject to any disclaimer, the term of this patent is extended or adjusted under 35 U.S.C. 154(b) by 410 days.

(21) Appl. No.: 11/923,321

(22) Filed: Oct. 24, 2007

(65) Prior Publication Data

US 2008/0312957 A1    Dec. 18, 2008

Related U.S. Application Data

(63) Continuation-in-part of application No. 11/796,123, filed on Apr. 25, 2007, now Pat. No. 7,690,173, which is a continuation-in-part of application No. 11/796,124, filed on Apr. 25, 2007, now Pat. No. 8,074,426, application No. 11/923,321, which is a continuation-in-part of application No. 11/796,125, filed on Apr. 25, 2007, application No. 11/923,321, which is a continuation-in-part of application No. 11/241,783, filed on Sep. 30, 2005, now Pat. No. 8,123,036.

(60) Provisional application No. 60/854,341, filed on Oct. 24, 2006, provisional application No. 60/795,413, filed on Apr. 26, 2006, provisional application No. 60/795,446, filed on Apr. 26, 2006, provisional application No. 60/795,370, filed on Apr. 26, 2006, provisional application No. 60/615,267, filed on Oct. 1, 2004.

(51) Int. Cl.
*B65B 1/04* (2006.01)
(52) U.S. Cl. ............ 53/473; 53/396; 235/375; 700/216; 705/2

(58) Field of Classification Search .................... 53/154, 53/493, 473, 396; 221/92, 123, 124, 133; 705/2; 235/375; 700/216, 219, 244
See application file for complete search history.

(56) References Cited

U.S. PATENT DOCUMENTS

| | | | |
|---|---|---|---|
| 3,933,245 | A | 1/1976 | Mullen |
| 4,039,080 | A | 8/1977 | Cappuccilli |
| 4,318,477 | A | 3/1982 | Kerpe |

(Continued)

FOREIGN PATENT DOCUMENTS

DE    3502647    7/1986

(Continued)

*Primary Examiner* — Thanh Truong
(74) *Attorney, Agent, or Firm* — Michael A. Kerr; Kerr IP Group, LLC

(57) ABSTRACT

A method for verifying a multiple prescription order having a plurality of different medications is described. The method comprises receiving a prescription order that includes a first medication that is different from a second medication. Additionally, the prescription order indicates that the first medication and second medication are to be taken at regular intervals. After entering the prescription order into a graphical user interface, the method verifies the entered prescription order by comparing the entered prescription order to the multiple prescription order. Multiple prescription packages are generated that combines the first medication and second medication in the same package that are intended to be taken at the prescribed interval. Each multiple prescription package is then inspected, and a verification process is initiated that confirms that the first medication and second medication are within each multiple prescription package. The multiple prescription packages are then placed into a container that is sealed.

12 Claims, 50 Drawing Sheets

U.S. PATENT DOCUMENTS

| | | |
|---|---|---|
| 4,546,901 A | 10/1985 | Buttarazzi |
| 4,693,371 A | 9/1987 | Malpass |
| 4,749,085 A | 6/1988 | Denney |
| 4,953,745 A | 9/1990 | Rowlett, Jr. |
| 5,186,345 A | 2/1993 | Ching An |
| 5,199,636 A | 4/1993 | Young |
| 5,597,995 A * | 1/1997 | Williams et al. ............... 235/375 |
| 5,883,370 A * | 3/1999 | Walker et al. ................. 235/375 |
| 6,202,923 B1 * | 3/2001 | Boyer et al. ................... 235/375 |
| 6,318,630 B1 * | 11/2001 | Coughlin et al. ............. 235/375 |
| 6,324,253 B1 | 11/2001 | Yuyama et al. |
| 6,449,927 B2 * | 9/2002 | Hebron et al. .................. 53/501 |
| 6,523,694 B2 | 2/2003 | Lux, Jr. et al. |
| 6,581,798 B2 * | 6/2003 | Liff et al. ......................... 221/13 |
| 6,757,898 B1 | 6/2004 | Ilsen et al. |
| 2002/0029223 A1 | 3/2002 | Rice et al. |
| 2002/0042725 A1 | 4/2002 | Mayaud |
| 2003/0018495 A1 | 1/2003 | Sussman |
| 2003/0174326 A1 * | 9/2003 | Rzasa et al. .................... 356/326 |
| 2004/0011961 A1 | 1/2004 | Platt et al. |
| 2004/0069674 A1 | 4/2004 | Siegel |
| 2004/0088187 A1 * | 5/2004 | Chudy et al. ....................... 705/2 |
| 2004/0123564 A1 | 7/2004 | McErlean et al. |
| 2004/0225528 A1 * | 11/2004 | Brock ................................ 705/2 |
| 2005/0049747 A1 | 3/2005 | Willoughby et al. |
| 2005/0061825 A1 | 3/2005 | Willoughby et al. |
| 2005/0209879 A1 | 9/2005 | Chalmers |

FOREIGN PATENT DOCUMENTS

| | | |
|---|---|---|
| WO | WO 96/13790 A1 | 5/1996 |
| WO | WO 2004/082561 A1 | 9/2004 |

* cited by examiner

FIG. 4

SYSTEM AND METHOD FOR VERIFYING AND ASSEMBLING A MULTIPLE PRESCRIPTION PACKAGE

CROSS REFERENCE

The present patent application claims priority from provisional patent application Ser. No. 60/854,341 entitled "METHOD FOR VERIFYING AND ASSEMBLING A MULTIPLE PRESCRIPTION PACKAGE" having a filing date of Oct. 24, 2006, and is a continuation-in-part of patent application Ser. No. 11/796,123 entitled "MULTIPLE PRESCRIPTION PRODUCTION FACILITY" having a filing date of Apr. 25, 2007 now U.S. Pat. No. 7,690,173 that claims priority from provisional patent application Ser. No. 60/795,413 having a filing date of Apr. 26, 2006, and is a continuation-in-part of patent application Ser. No. 11/796,124 entitled "MULTIPLE PRESCRIPTION PACKAGE AND METHOD FOR FILLING THE PACKAGE" having a filing date of Apr. 25, 2007 now U.S. Pat. No. 8,074,426 that claims priority from provisional patent application Ser. No. 60/795,446 having a filing date of Apr. 26, 2006, and is a continuation-in-part of patent application Ser. No. 11/796,125 entitled "SYSTEM AND METHOD FOR REMOTELY PROCESSING A MULTIPLE PRESCRIPTION ORDER" having a filing date of Apr. 25, 2007 that claims priority from provisional patent application Ser. No. 60/795,370 having a filing date of Apr. 26, 2006, and is a continuation-in-part of patent application Ser. No. 11/241,783 entitled "PILL ASSEMBLY FOR PILL PACKAGING AND DELIVERY SYSTEMS" having a filing date of Sep. 30, 2005 now U.S. Pat. No. 8,123,036 that claims priority from provisional patent application Ser. No. 60/615,267 having a filing date of Oct. 1, 2004, wherein the contents of each patent application are incorporated by reference.

BACKGROUND

1. Field

This description relates to a method for verifying and assembling a multiple prescription package. More particularly, the description relates to a method for verifying and assembling the multiple prescription packages for a particular individual.

2. Description of Related Art

One of the major problems in taking prescribed daily medications emanates from patients having to take more than one medication in the form of pills or tablets. A principal concern is determining whether all medications are in compliance with the prescribed daily regimen. Many times this concern is compounded by the requirement that portions of the various medications must be taken at different times during the day.

The fear of taking improper dosages of prescribed medication can be particularly acute in the elderly, many of whom have some degree of mental dementia and can easily be confused as to whether they have taken all of their medications at the correct time. Some patients have difficulty sorting out the medications prior to taking them and taking the medication in a timely manner. Providing medications to disabled or incapacitated individuals can also be complicated because one caregiver may oversee the medication of many patients.

One solution to the problem of taking multiple medications is to pre-package the multiple medications so that users can take the pre-packaged medications at a predetermined time. Generally, these methods of pre-packaging medications are targeted to patients that may lack maturity or mental capacity to take the correct medications at the correct time. For example, young children in a school or campground, and elderly individuals in elder care centers, or nursing homes are target groups for the pre-packaging of medications. Some of the pre-packaged medications are placed in a small plastic bag, which may be easily misplaced. Other pre-packaged medications are placed in sealed cups that are difficult to open.

Additionally, the pre-packaging of multiple medications is also limited by distributing pre-packaged medications to a limited geographical location. For example, the pre-packaging of multiple medications is only provided in hospitals, medical institutions, campgrounds, or schools. Thus, the geographic limitation makes it difficult to effectively distribute the pre-packaged medications to a broad group of people over a broad geographic area.

Furthermore, pre-packaged multiple medications are difficult to order because the pre-packaging of multiple medications is a specialty service that has not been automated. The manual ordering systems are expensive to administer because they lack automation. Therefore, there is a need for a highly automated ordering system and process that is simple and cost effective for a patient or a pharmacist to use. An automated system and method for receiving orders would make it substantially easier to process a multiple prescription order, which would in turn make the process much more cost effective.

Although multiple prescription filling systems are available, e.g. the McKesson PACMED system, these systems has limited labeling capabilities. Additionally, these filling systems do not have procedures to verify the multiple prescription order before filling a pouch or cup. Furthermore, these filling systems fail to provide a method for assembling a multiple prescription order that can be easily transported and administered, so that the multiple medications can be taken at the appropriate time. Further still, these filling systems fail to verify that each pouch in a filled prescription order has the appropriate medication.

SUMMARY

A method for verifying a multiple prescription order having a plurality of different medications is described. The method comprises receiving a prescription order that is associated with a particular patient. The prescription order comprises a plurality of medications having a first medication that is different from a second medication. Additionally, the prescription order indicates that the first medication and second medication are to be taken at regular intervals, e.g. morning, noon, afternoon, or bedtime. After entering the prescription order into a graphical user interface, the method proceeds to verify the entered prescription order by comparing the entered prescription order to the multiple prescription order. A plurality of preliminary packages that combines the first medication and second medication in the same package are generated. The preliminary packages are to be taken at the prescribed interval. Each preliminary package is then inspected, and a verification process is initiated that confirms that the first medication and second medication are within each preliminary package. The preliminary packages are then placed into a container, which is sealed.

A method for assembling a multiple prescription package having a plurality of different medications is also described. The method for assembling the multiple prescription order also comprises communicating the prescription order to a filling system configured to produce a plurality of preliminary packages that comprises the first medication and second medication.

A method for verifying a filled multiple prescription order for a plurality of different medications is also provided. The method for verifying the filled multiple prescription order comprises producing a plurality of labels associated with the prescription, validating the plurality of labels by comparing the labels to the prescription, and applying the labels to each container that is configured to receive the preliminary packages.

DRAWINGS

The present invention will be more fully understood by reference to the following drawings which are for illustrative, not limiting, purposes.

FIG. 4 shows an illustrative graphical user interface (GUI) for receiving an order.

Figure 20A:
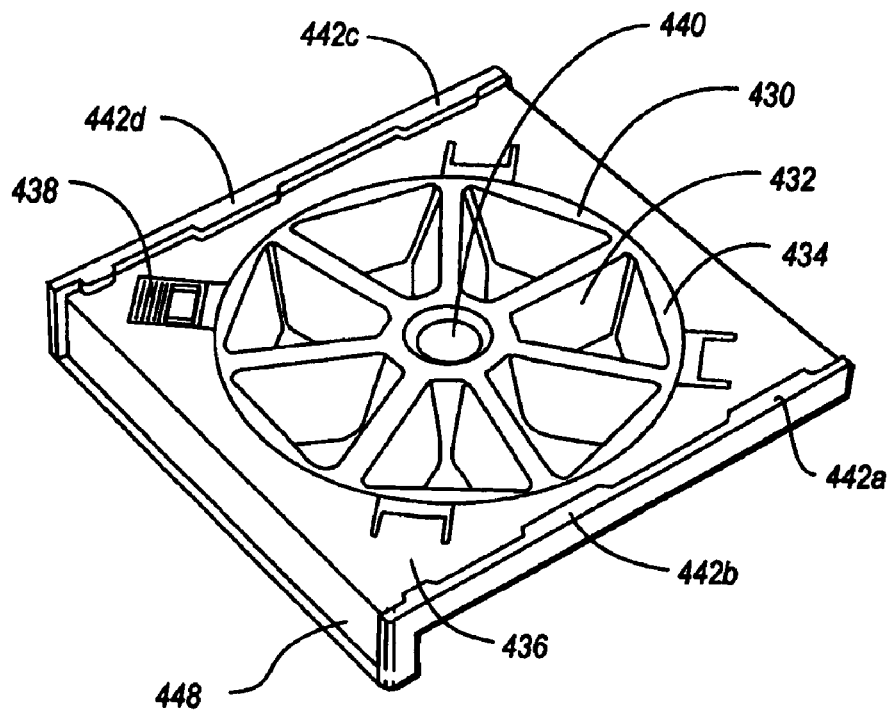

FIG. 20A there is a top view of a dispensing sleeve housing a plurality of rounded multiple prescription containers.

Figure 20B:
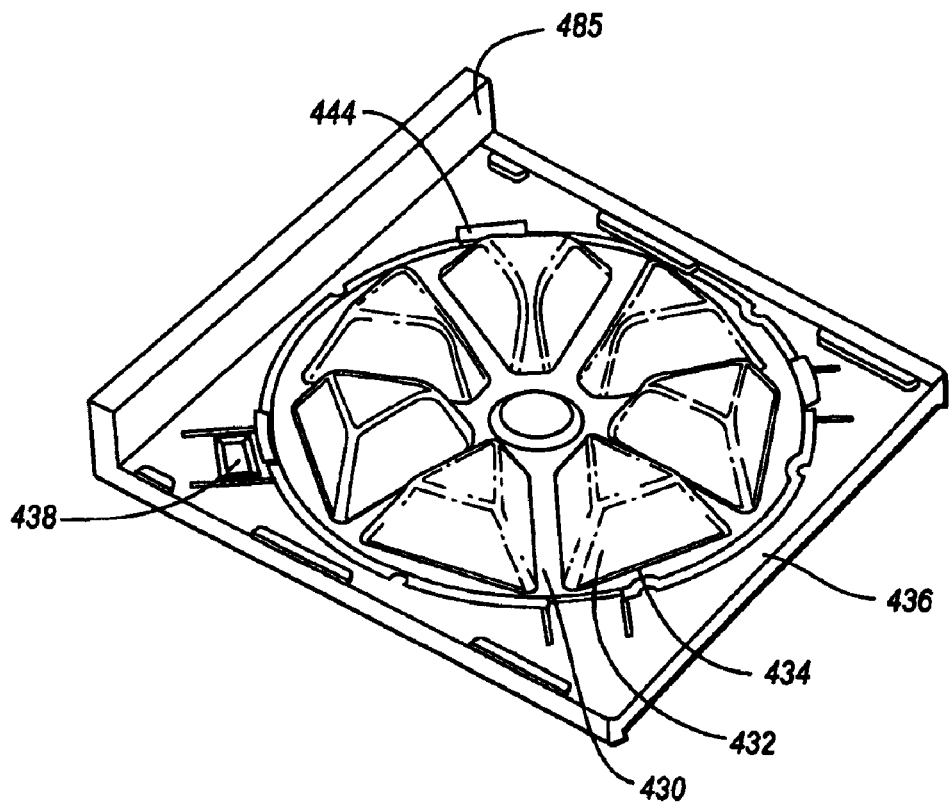

FIG. 20B is a bottom view of the dispensing sleeve housing the rounded containers described in FIG. 20A.

Figure 21A:
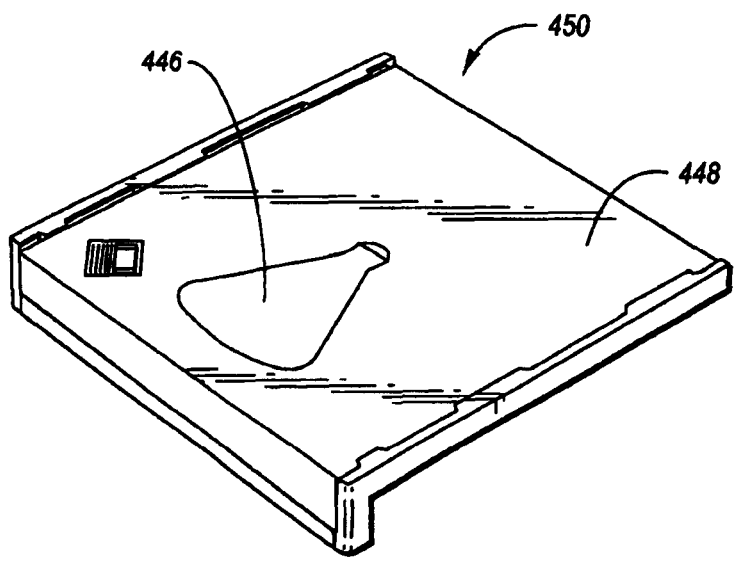

FIG. 21A is the dispensing sleeve housing the rounded containers having a first lid and a cover.

Figure 22:
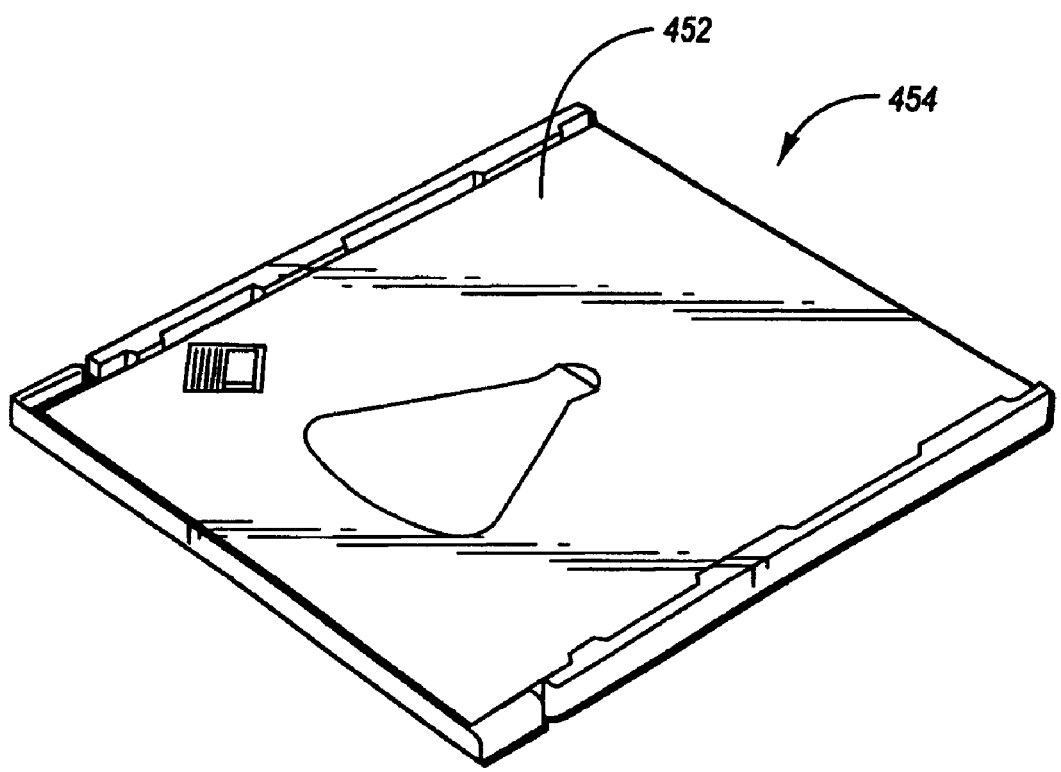

FIG. 22 shows an alternative sleeve that does not comprise a rim.

Figure 23A:
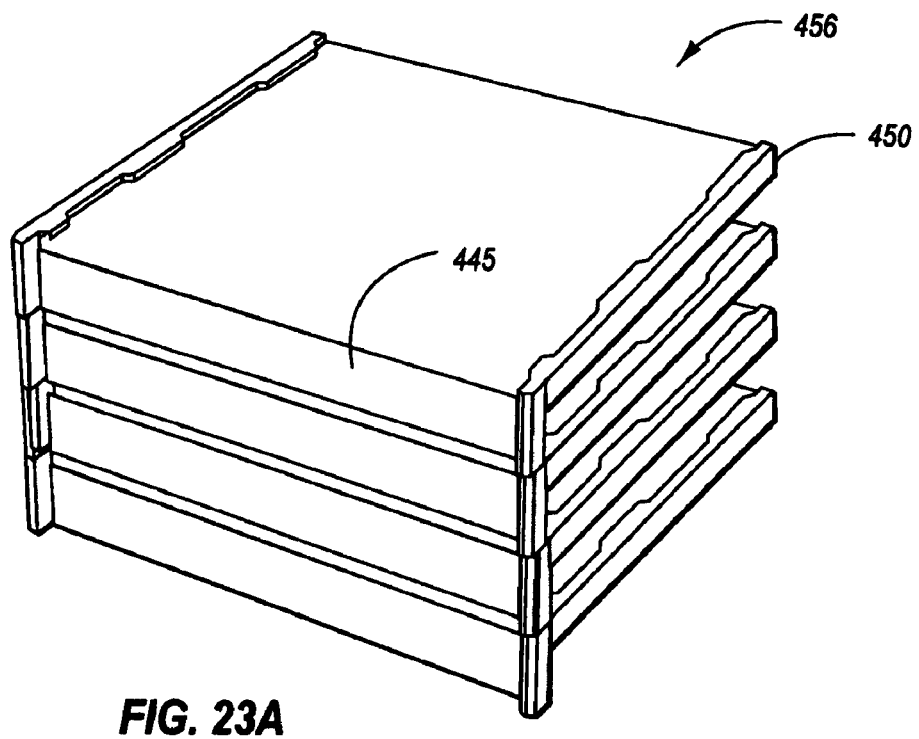
Figure 23B:
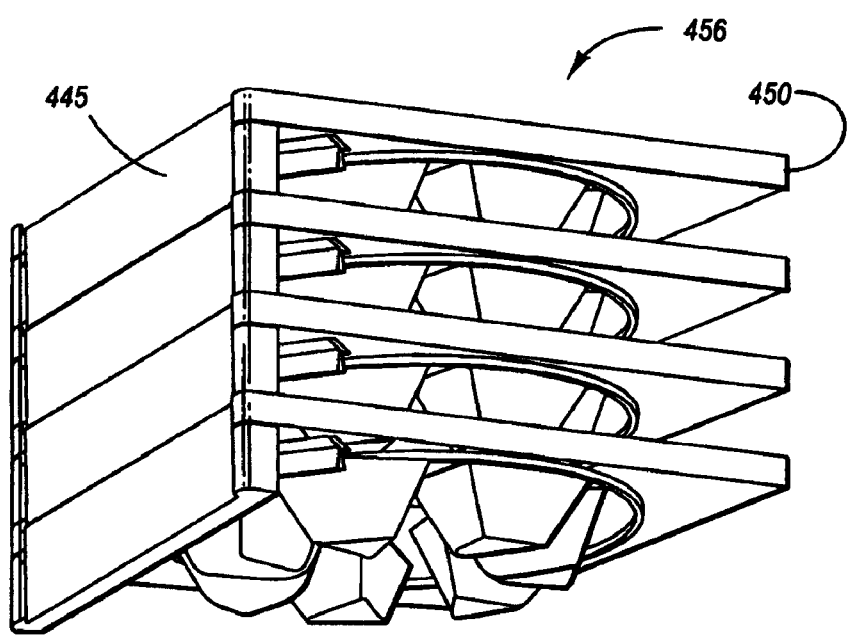

FIGS. 23A and 23B show two separate perspective views of a plurality of stacked rounded multiple prescription container assemblies.

Figure 24A:
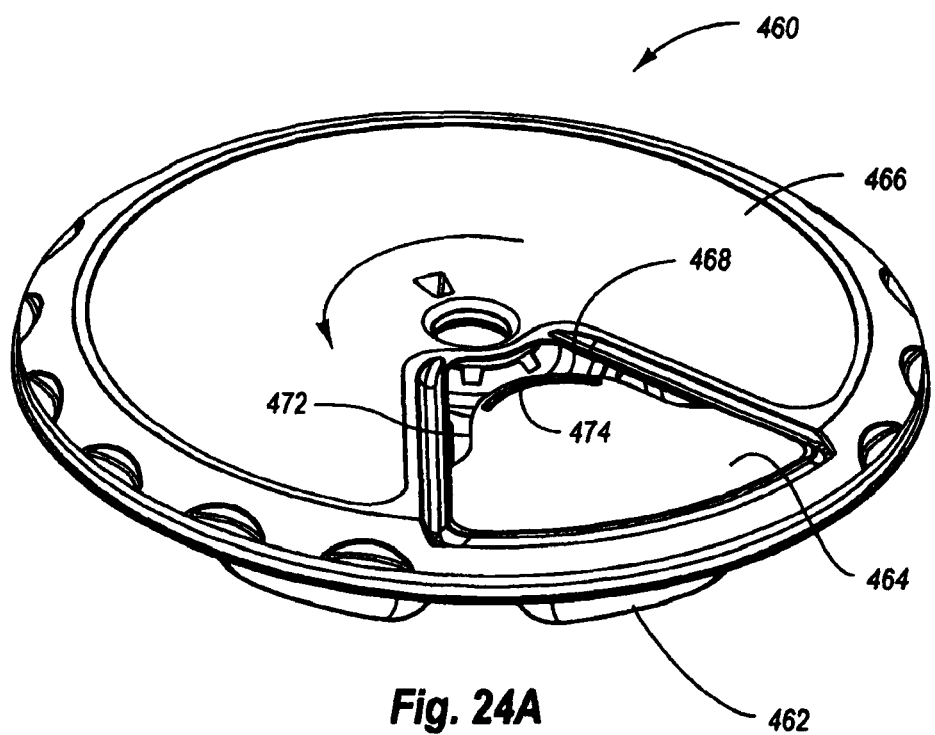

FIG. 24A is a perspective view of a circular multiple prescription container assembly.

Figure 24B:
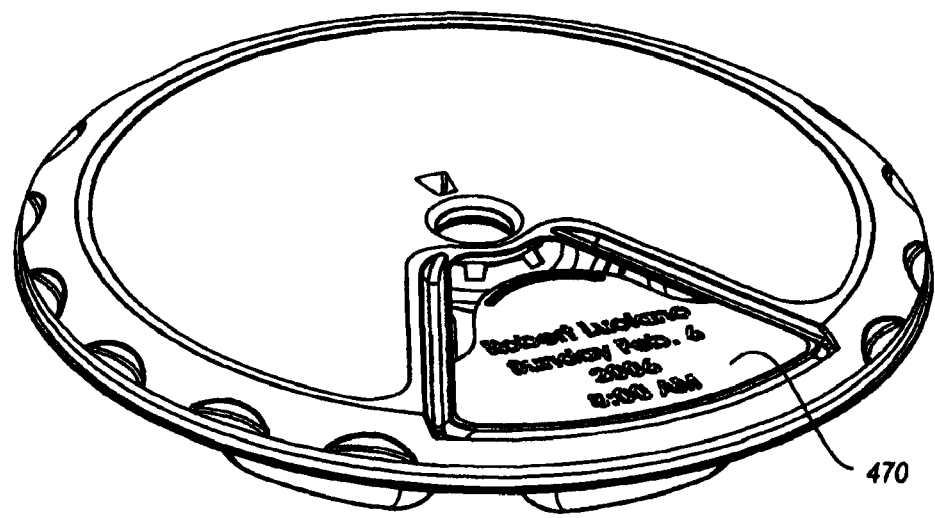

FIG. 24B is an illustrative embodiment in which the lid has printed information.

Figure 25:
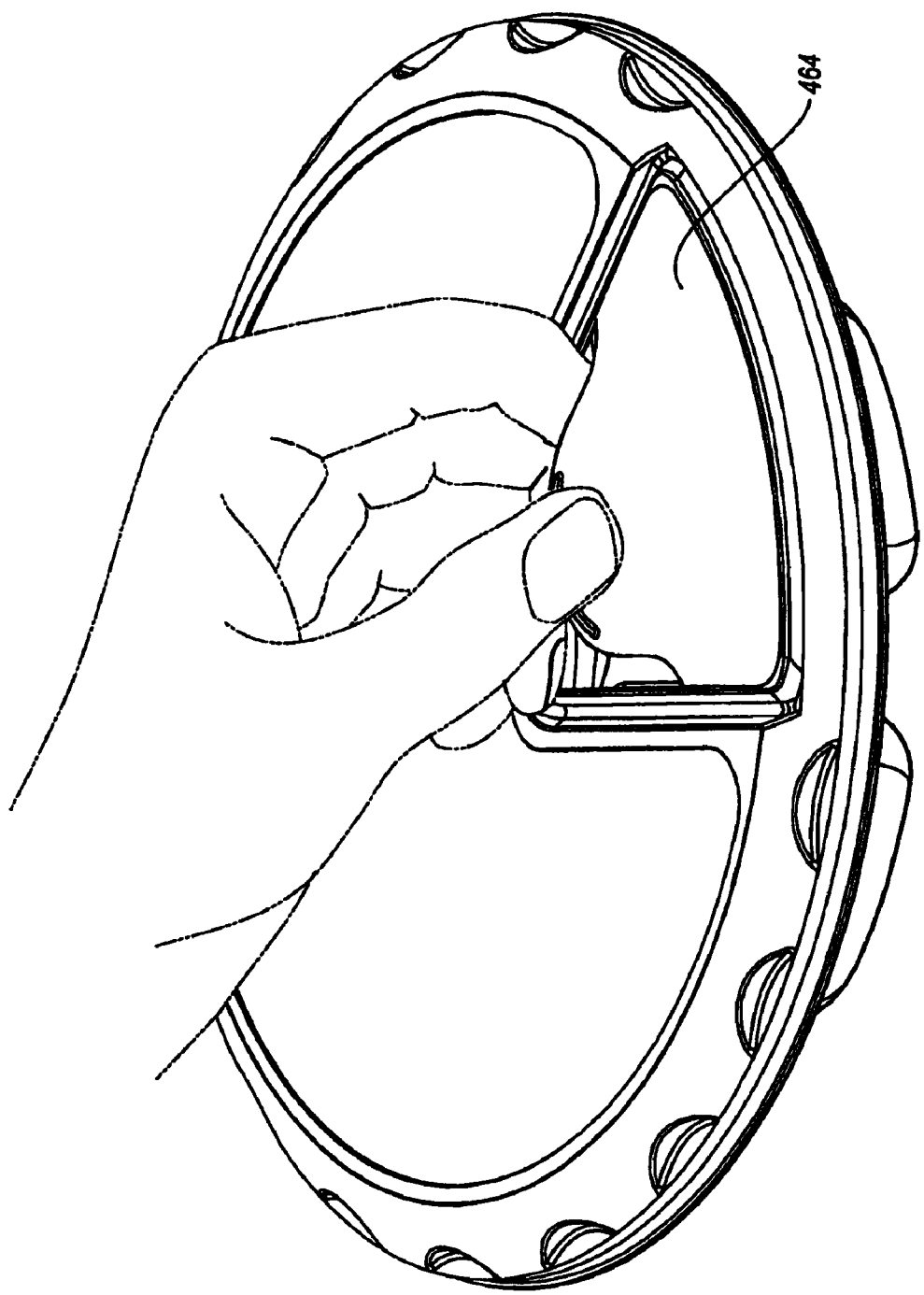

FIG. 25 provides a more detailed view of a patient or caregiver removing the lid from the circular multiple prescription container in FIGS. 24A and 24B.

Figure 26:
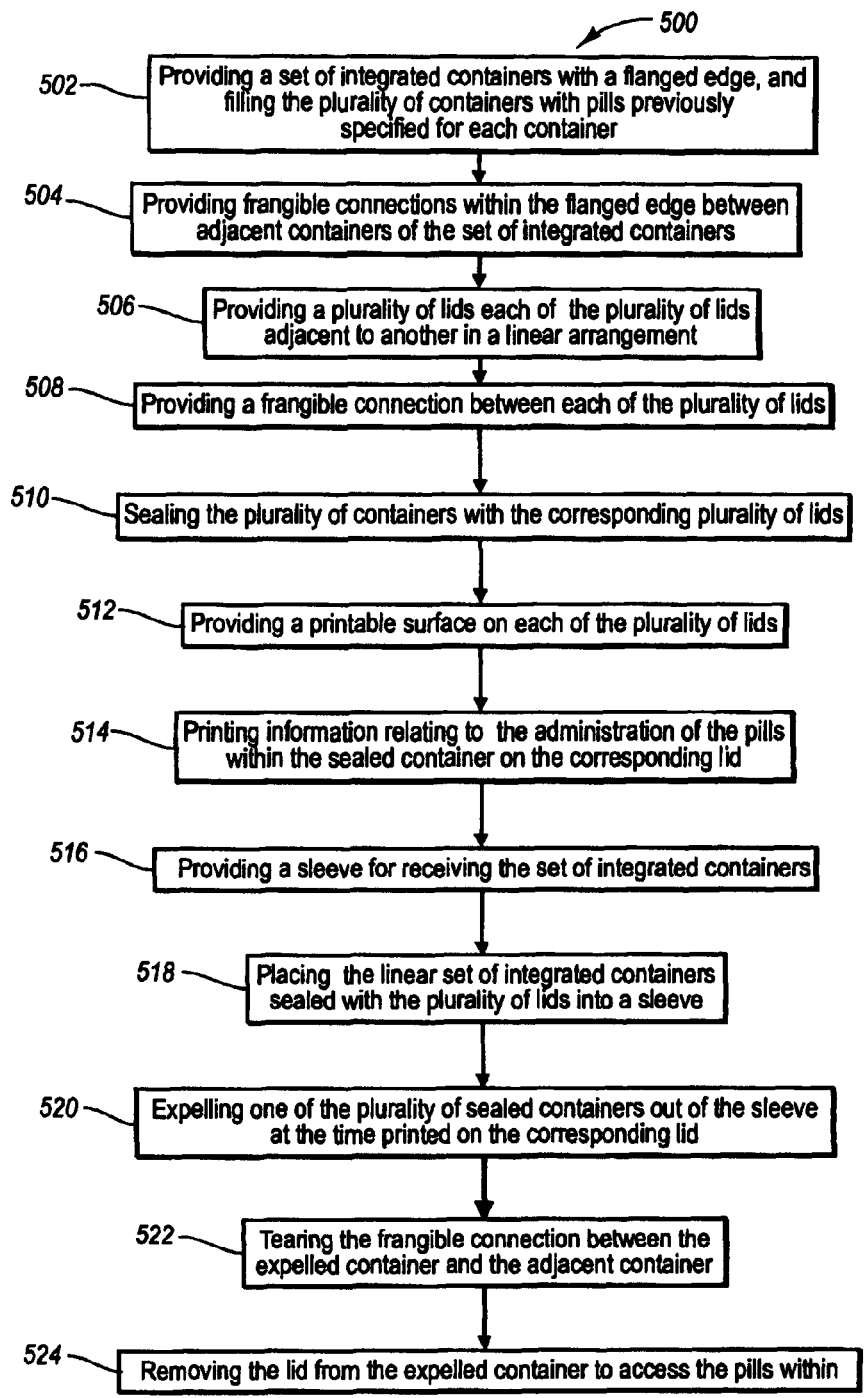

FIG. 26 is a flowchart showing an illustrative embodiment of the method for dispensing tablets which utilizes a secondary package or sleeve for receiving a multiple prescription container.

Figure 27:
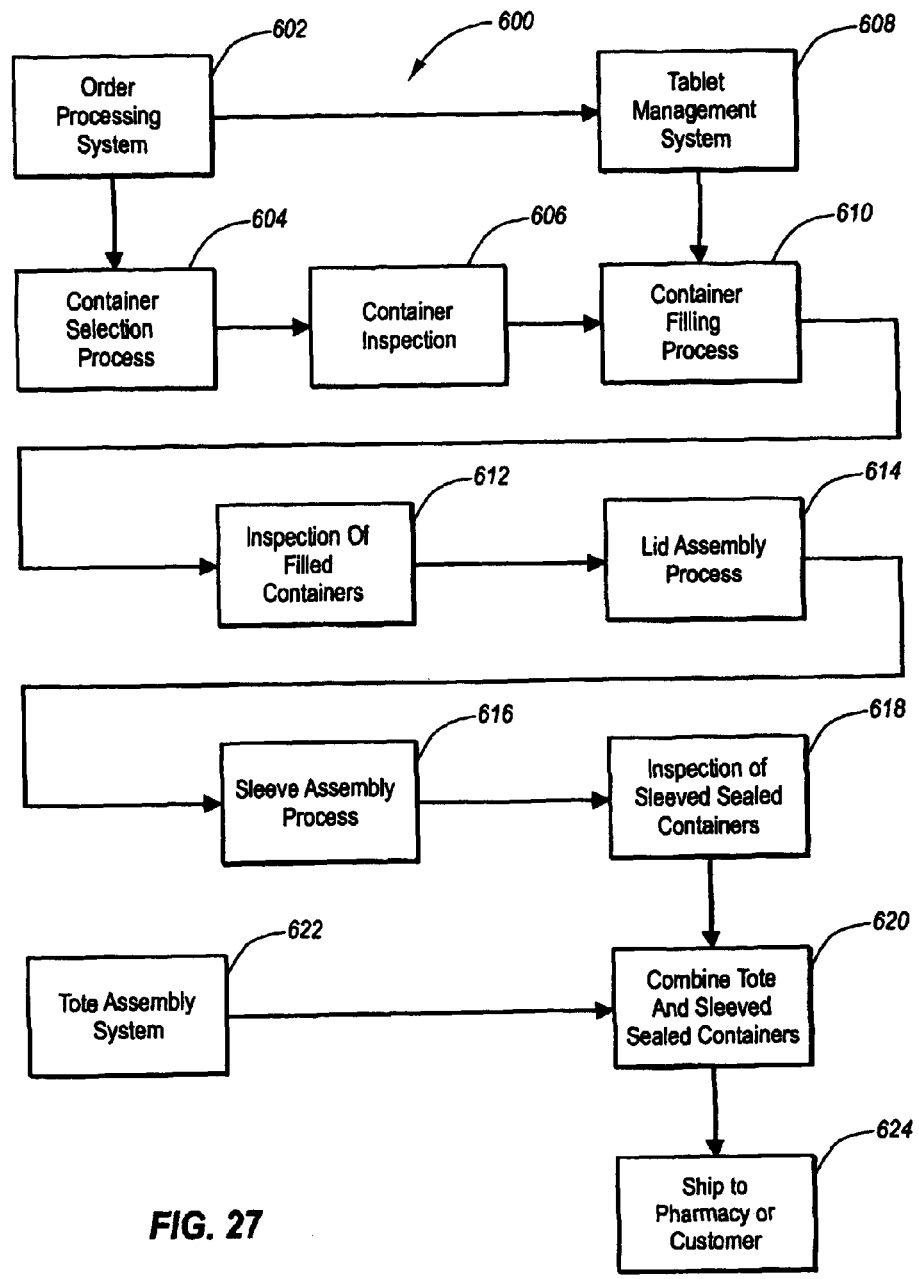

FIG. 27 is a flowchart showing the processes and systems used by a production facility to fill a prescription order.

Figure 28:
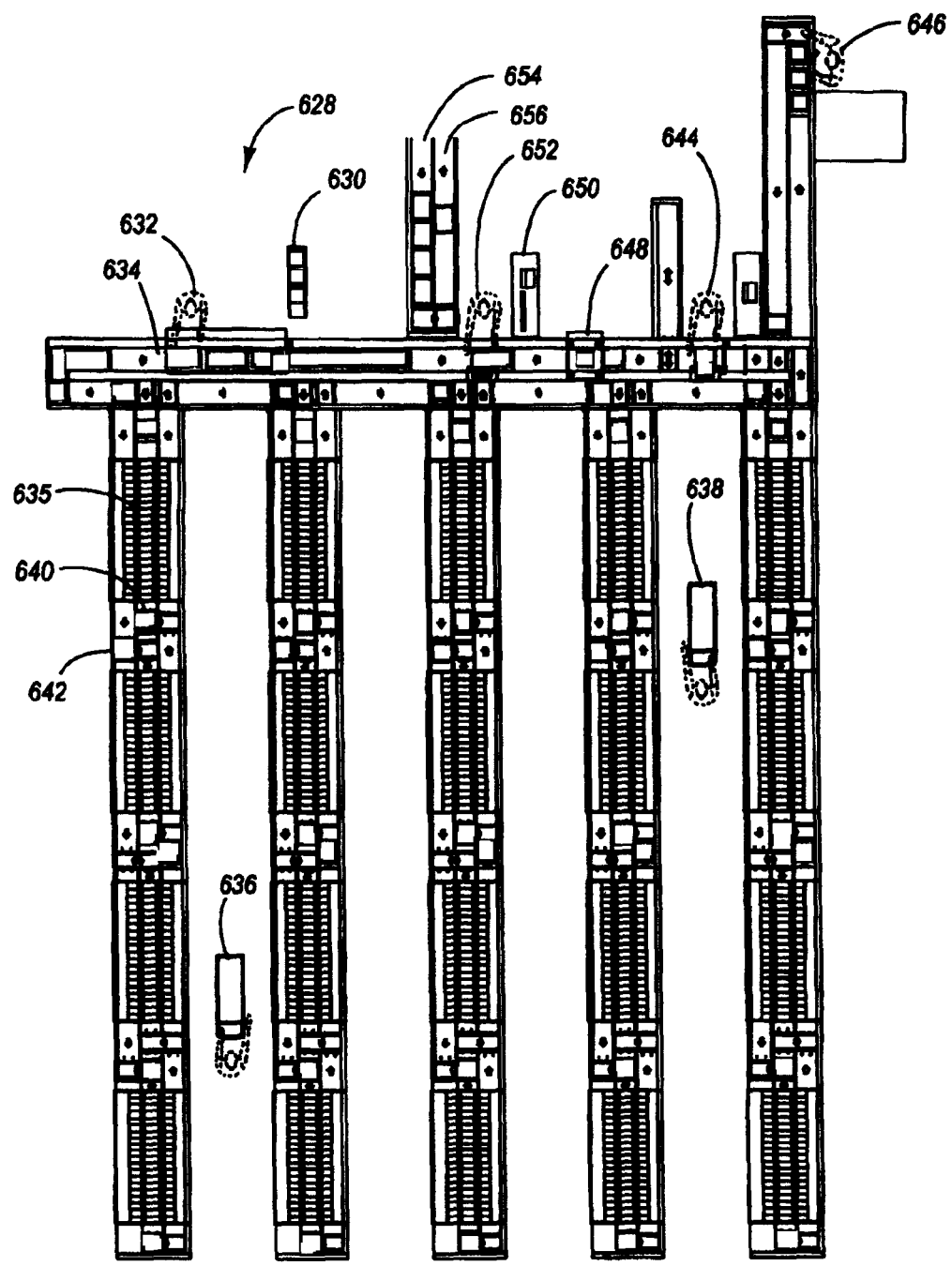

FIG. 28 is a top view of an illustrative manufacturing floor that fills the prescription order.

Figure 29:
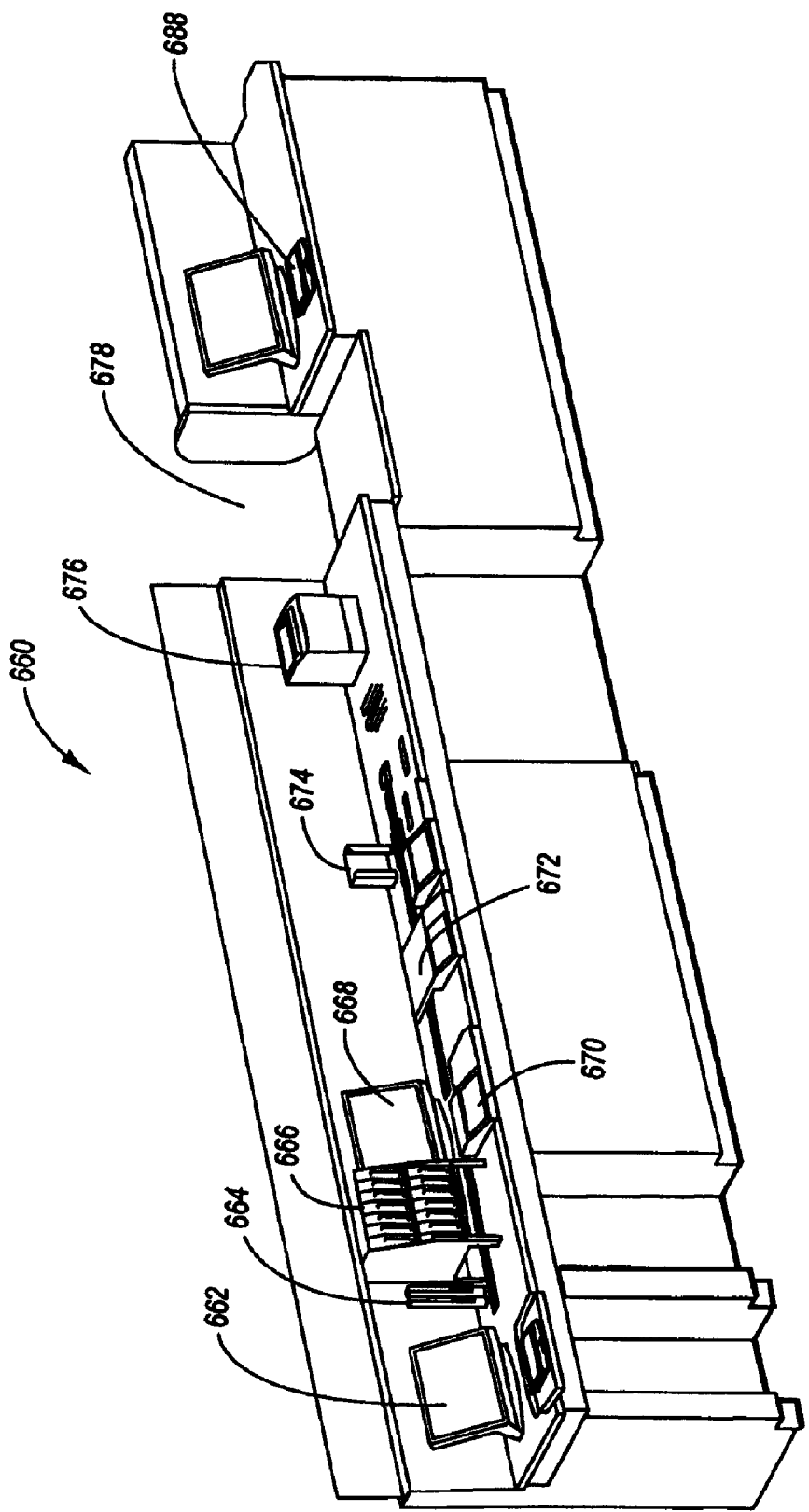

FIG. 29 is an isometric view of an illustrative tabletop system that can also fill the prescription order.

Figure 30:
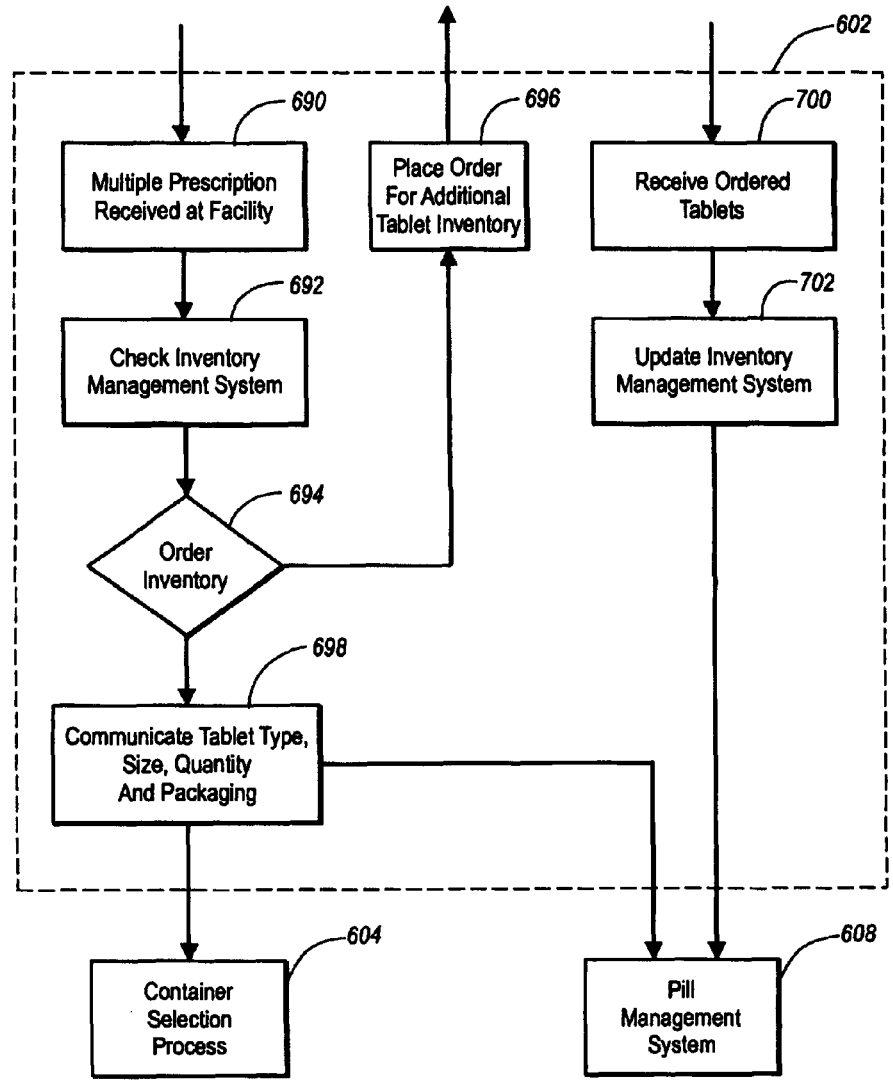

FIG. 30 is a block diagram of an illustrative order processing system.

Figure 31:
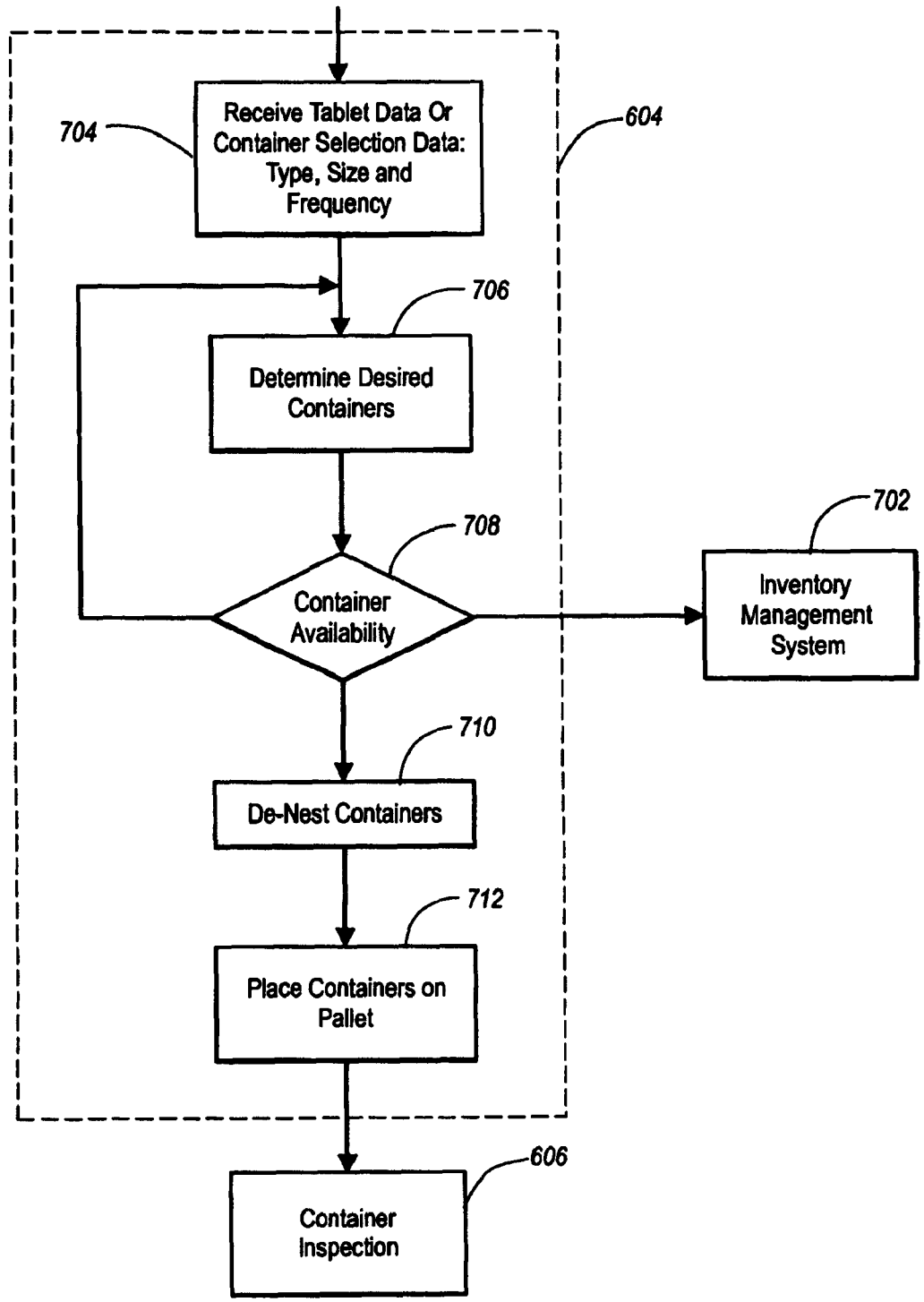

FIG. 31 is a flowchart of an illustrative container selection process.

Figure 32:
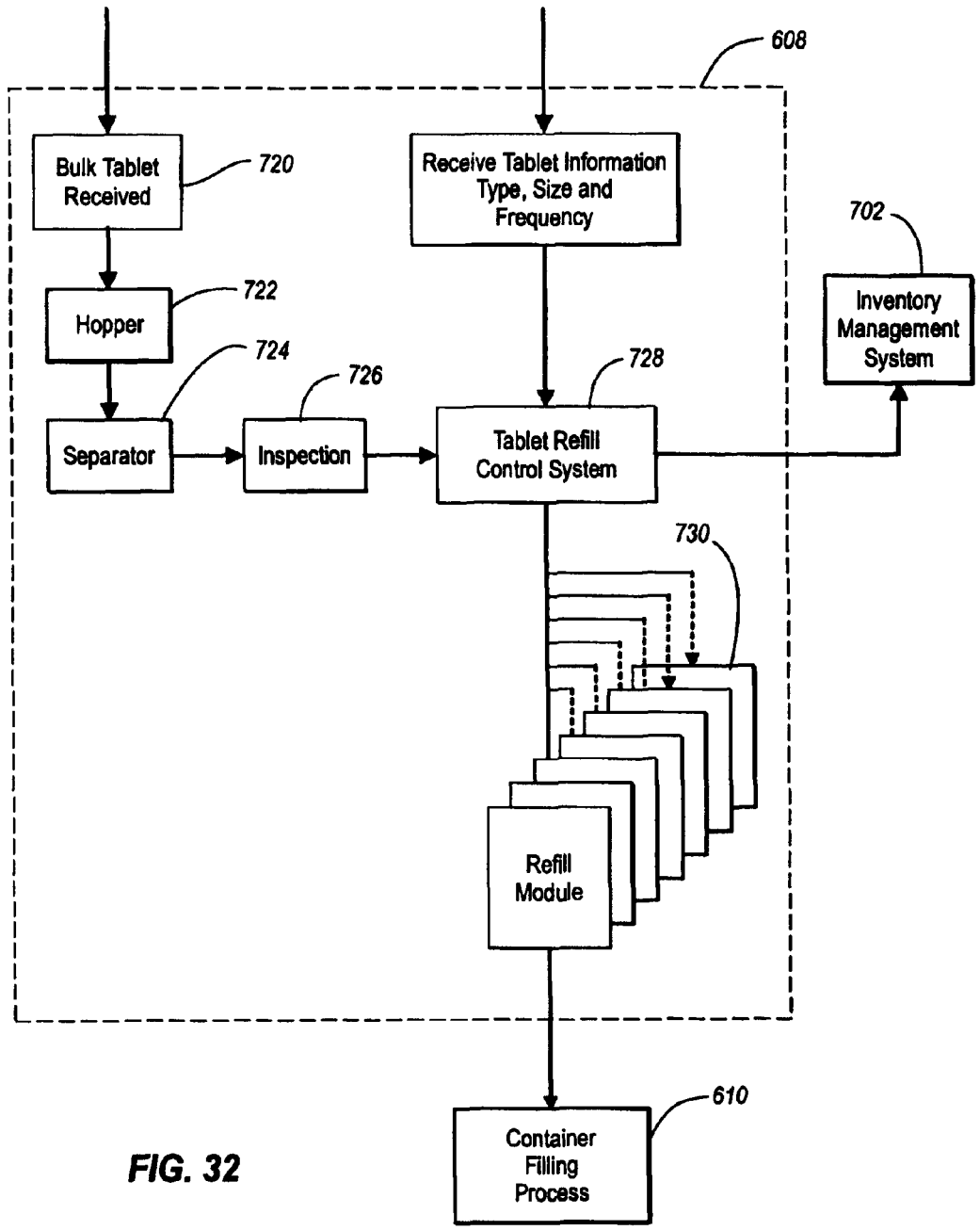

FIG. 32 is a block diagram of an illustrative pill management system.

Figure 33:
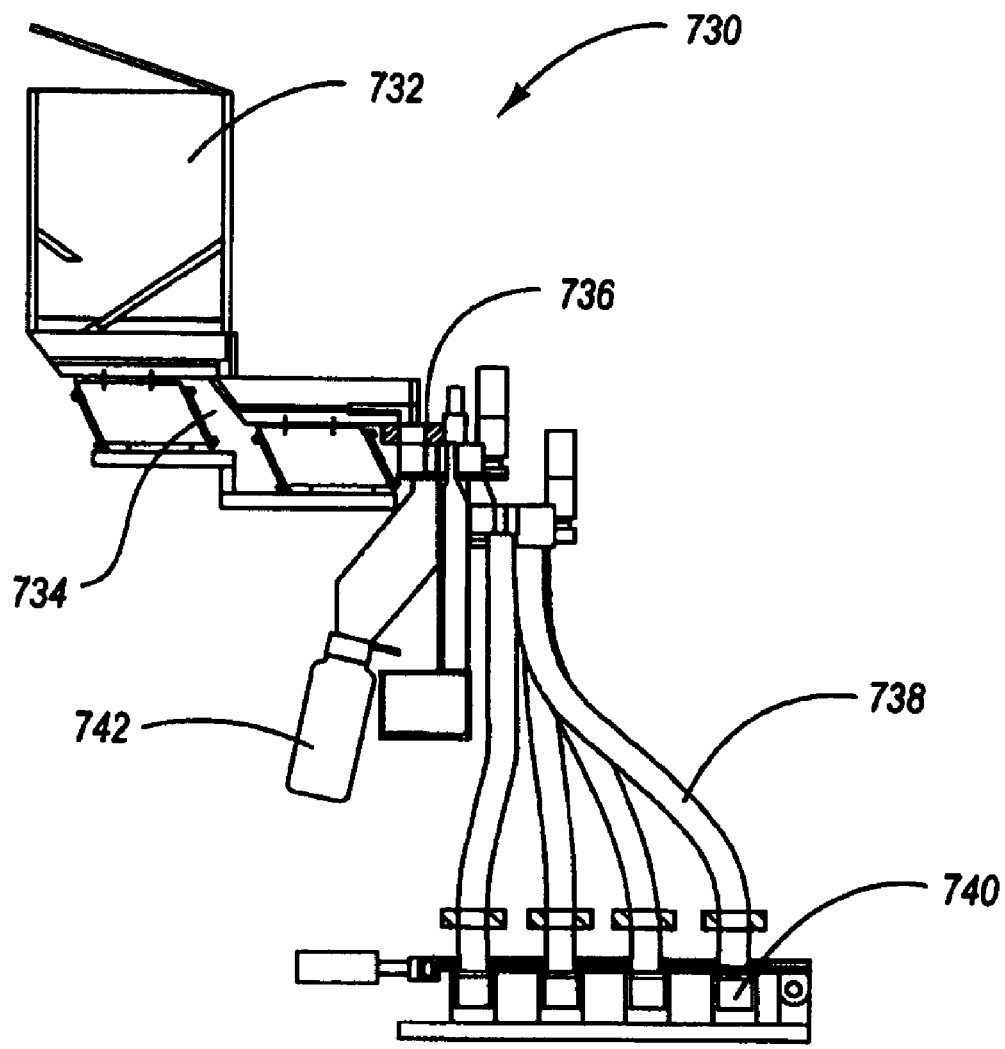

FIG. 33 is a side view of an illustrative refill module.

Figure 34:
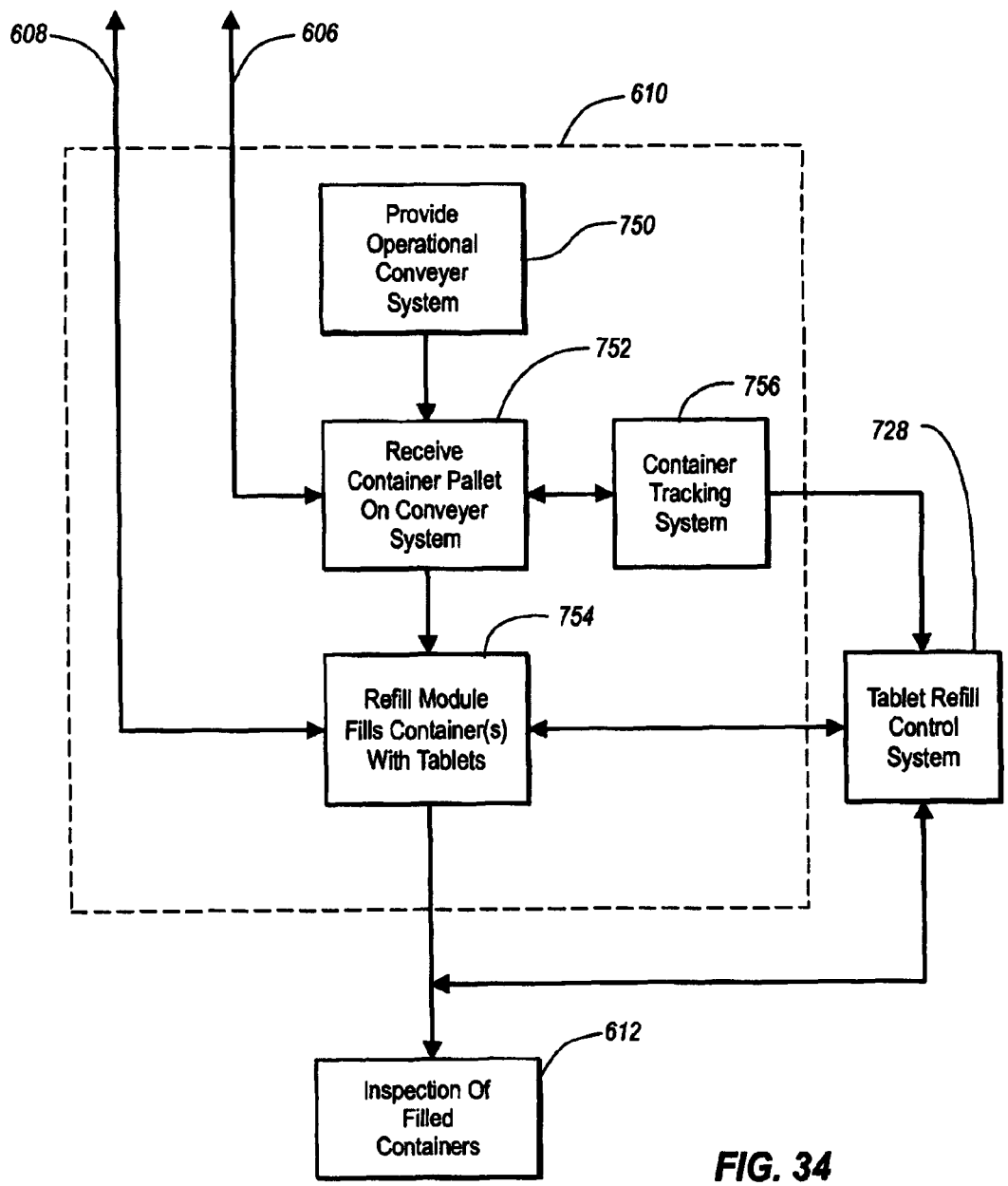

FIG. 34 is a flowchart of an illustrative container filling process.

Figure 35:
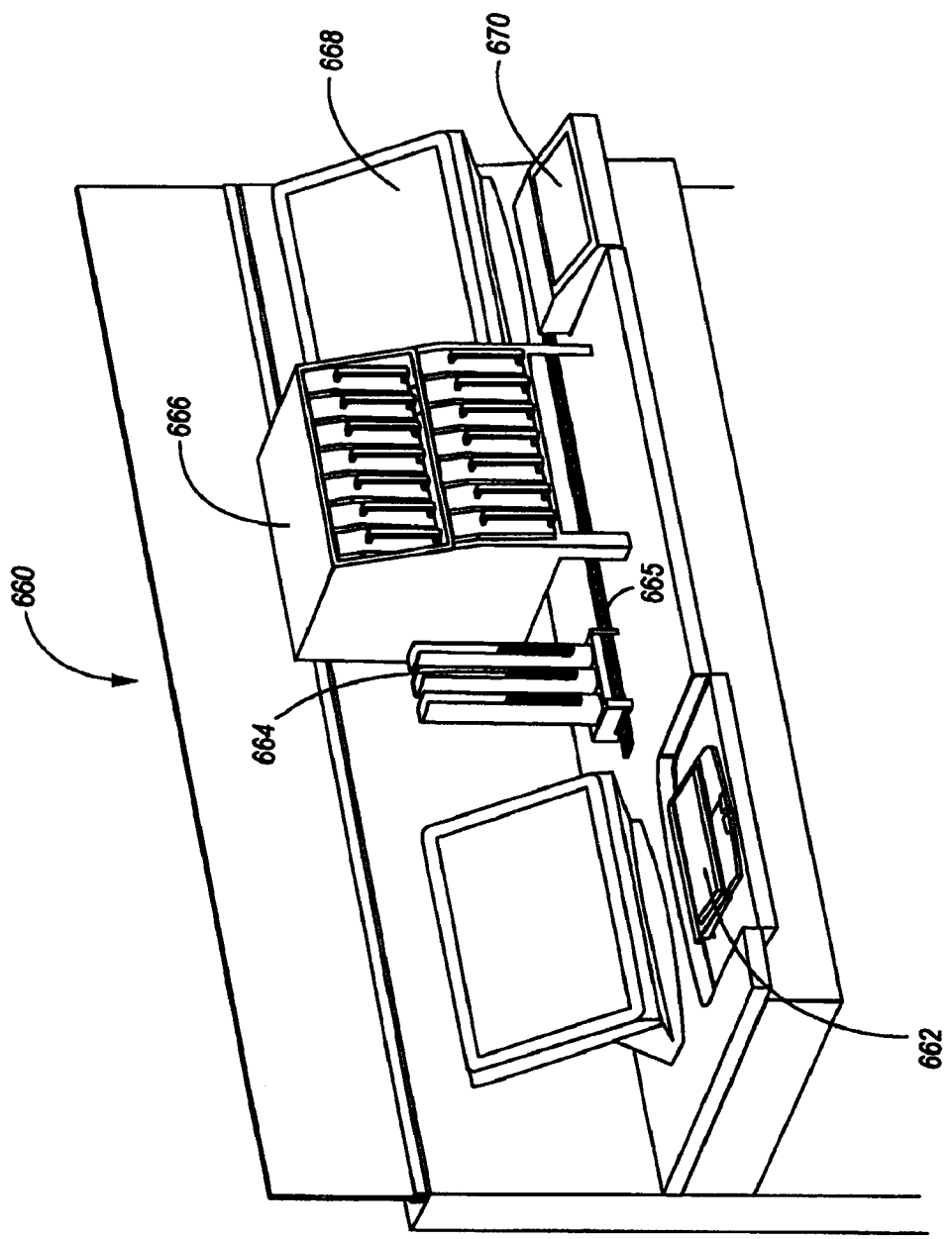

FIG. 35 is an isometric view of an illustrative tabletop system including order processing, pill management, container selection, container inspection, and container filling.

Figure 36:
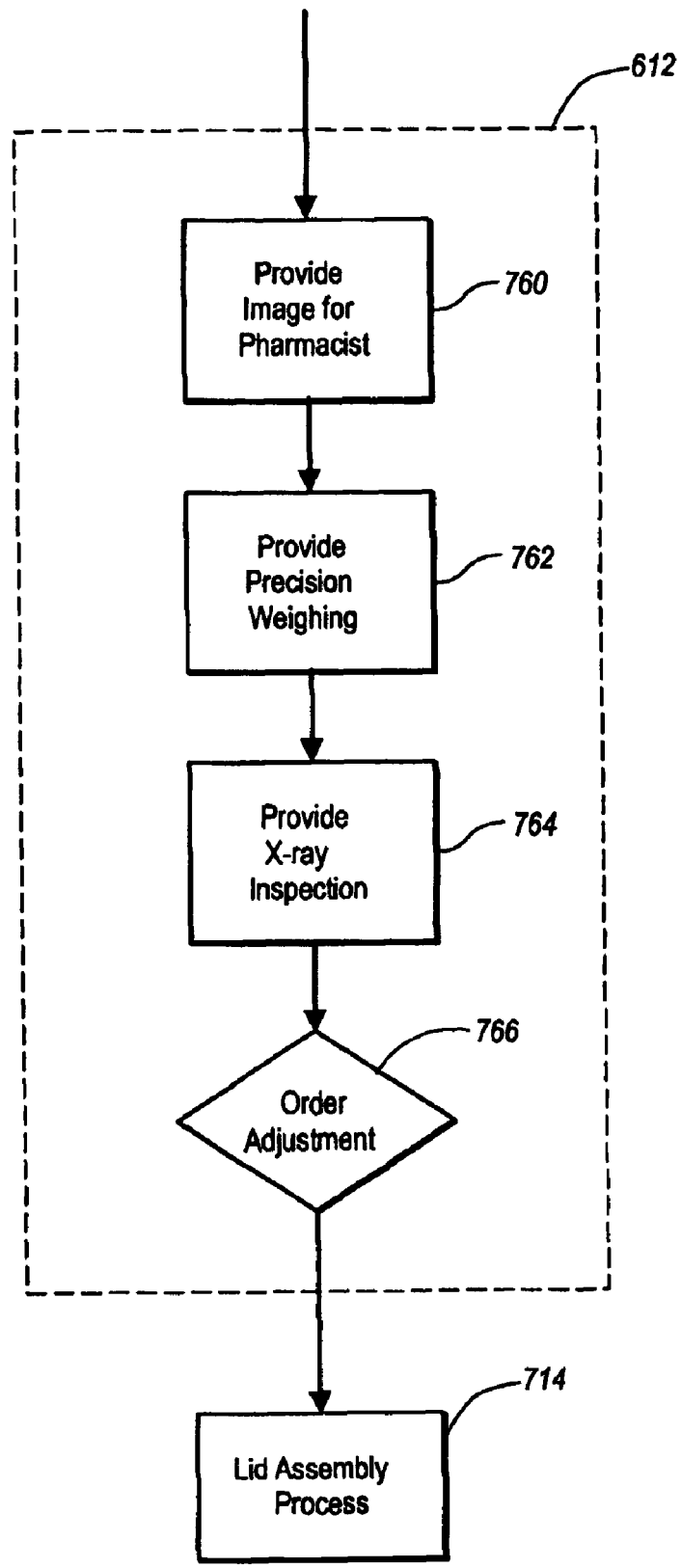

FIG. 36 is a flowchart showing the inspection of filled multiple prescription containers.

Figure 37:
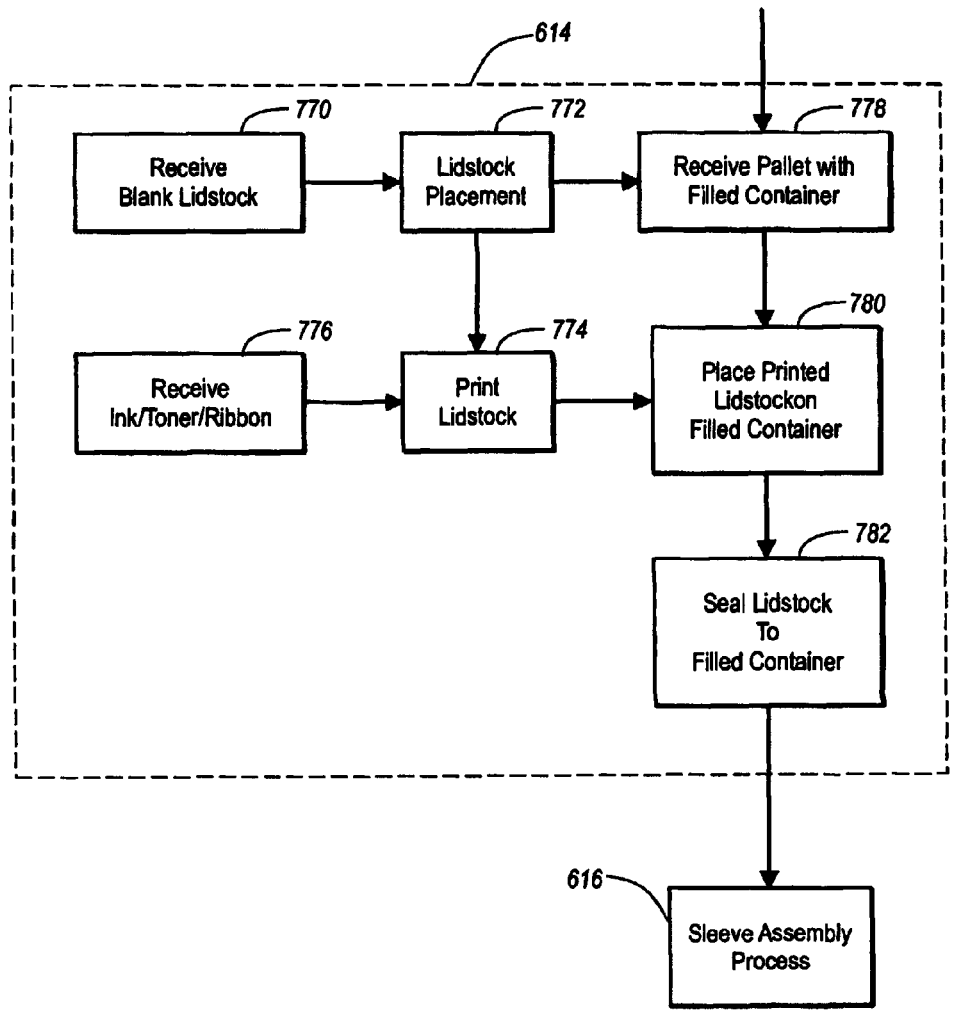

FIG. 37 is a flowchart showing an illustrative lid assembly process.

Figure 38:
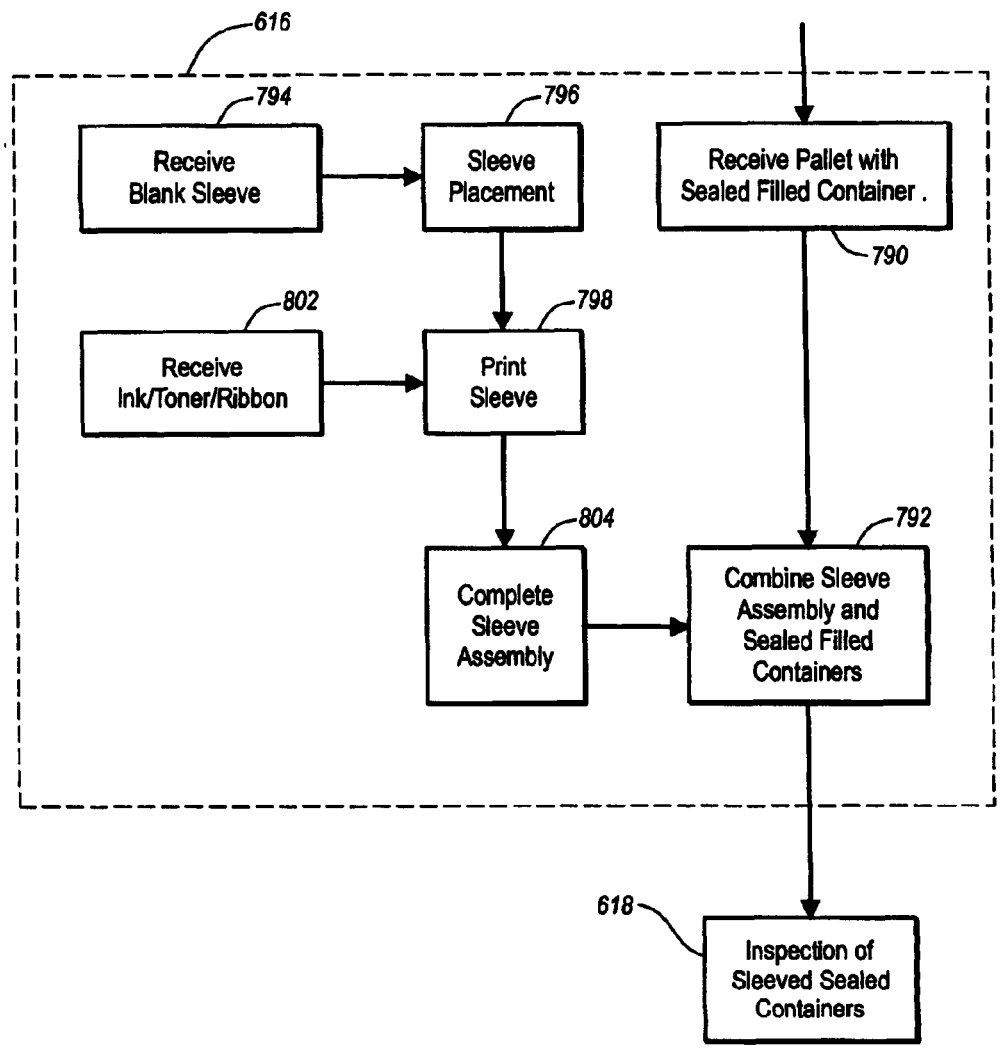

FIG. 38 is a flowchart of an illustrative sleeve assembly process.

Figure 40:
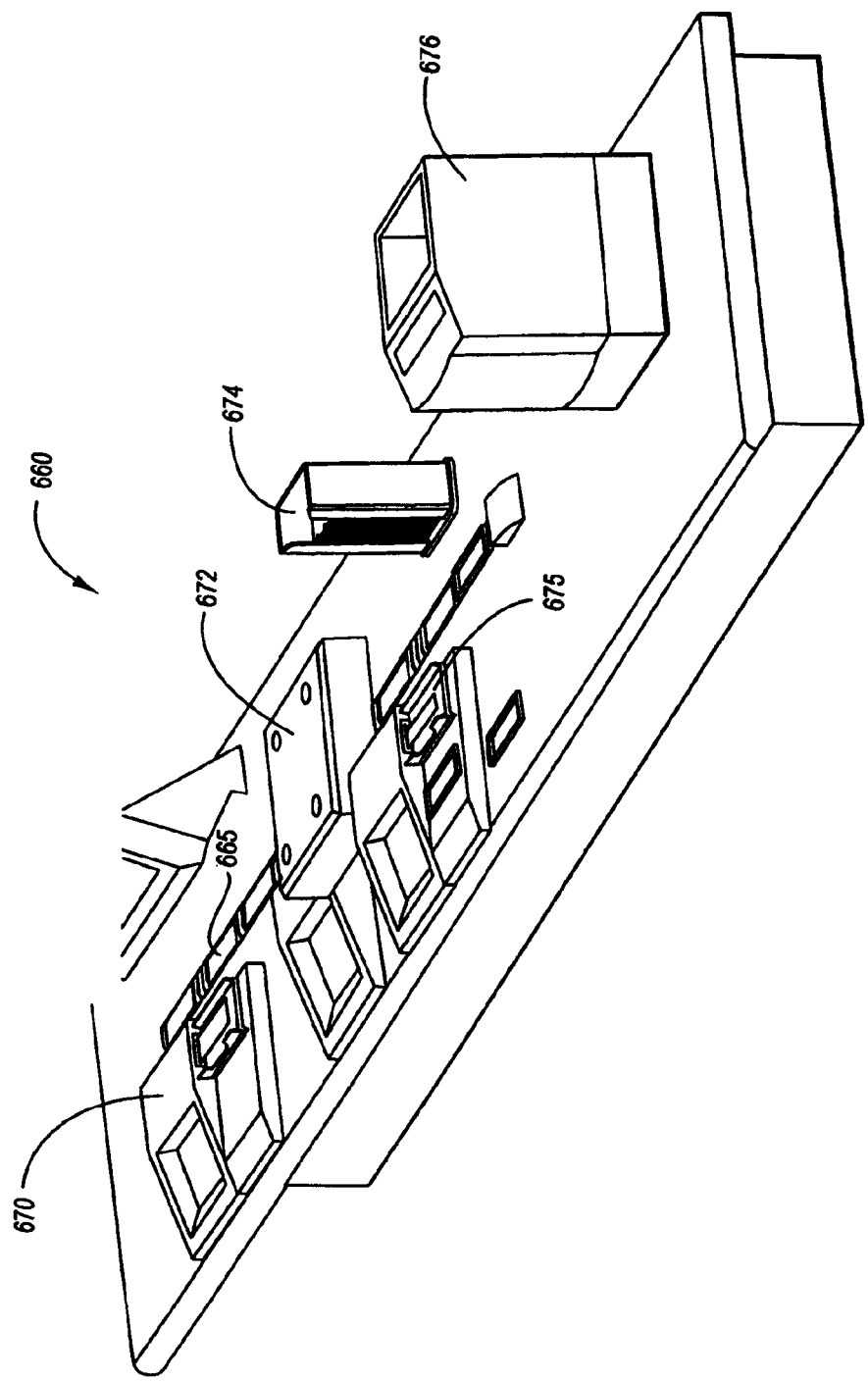

FIG. 40 is an isometric view of the illustrative tabletop system with filled container inspection, lid assembly, sleeve assembly, and inspection of sleeved and sealed containers.

Figure 41:
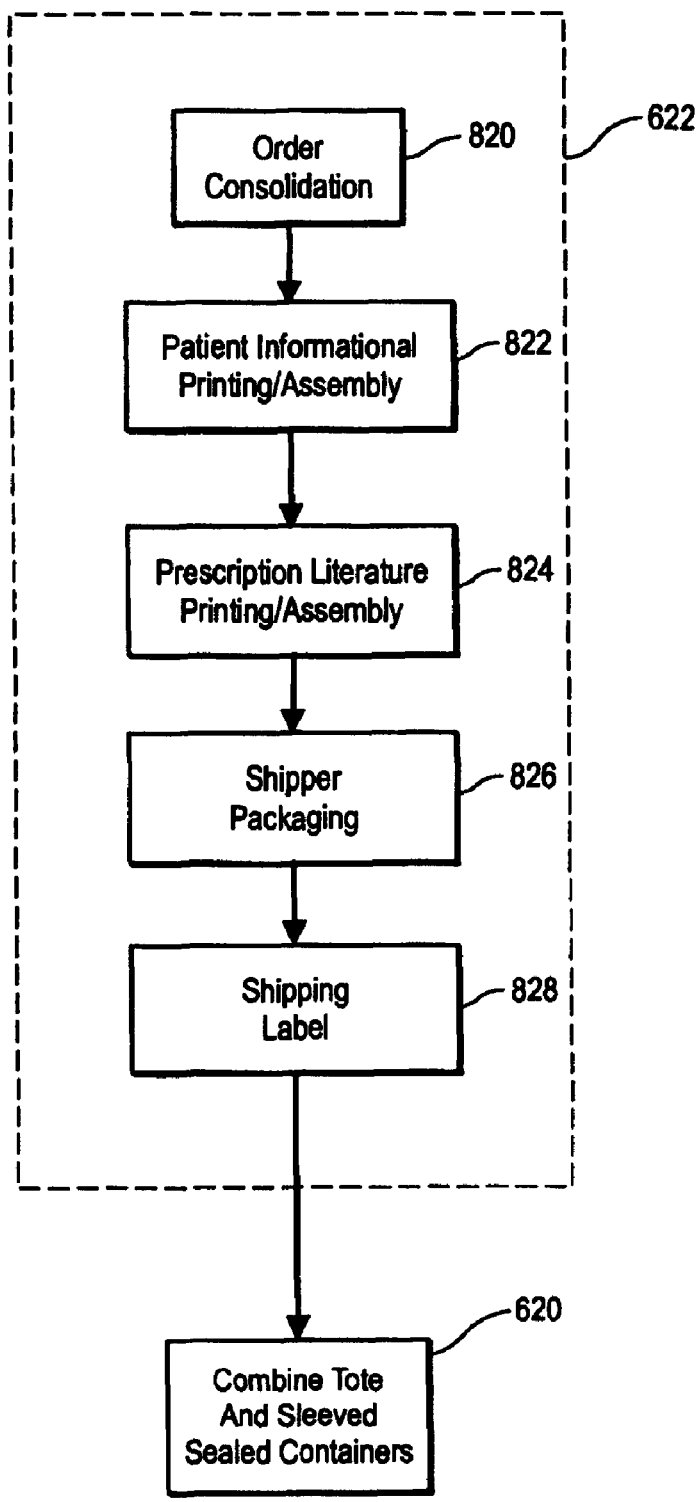

FIG. 41 is a block diagram of a tote assembly system.

Figure 42:
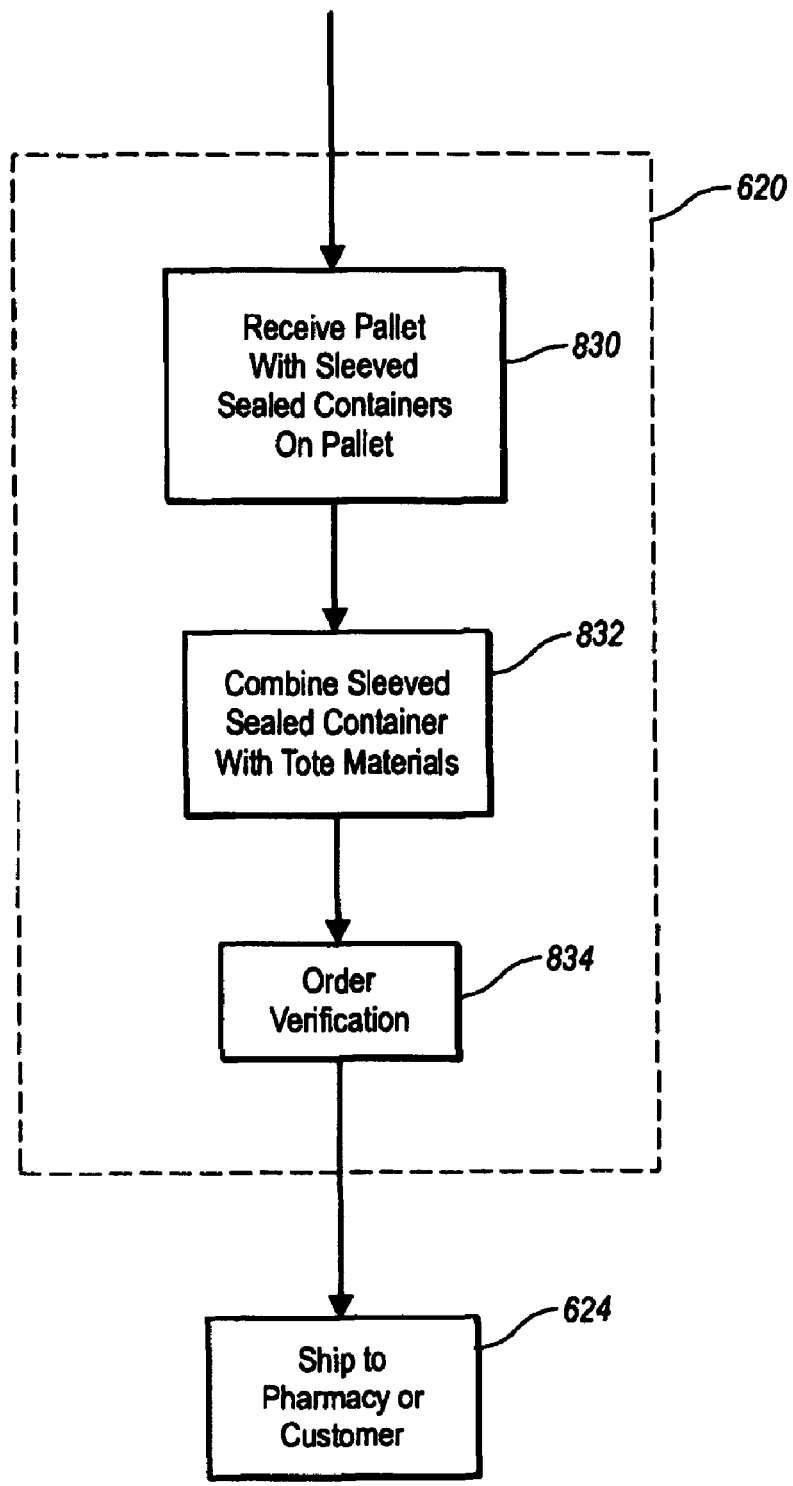

FIG. 42 is a block diagram showing the combining of the tote and sealed multiple prescription containers.

Figure 43:
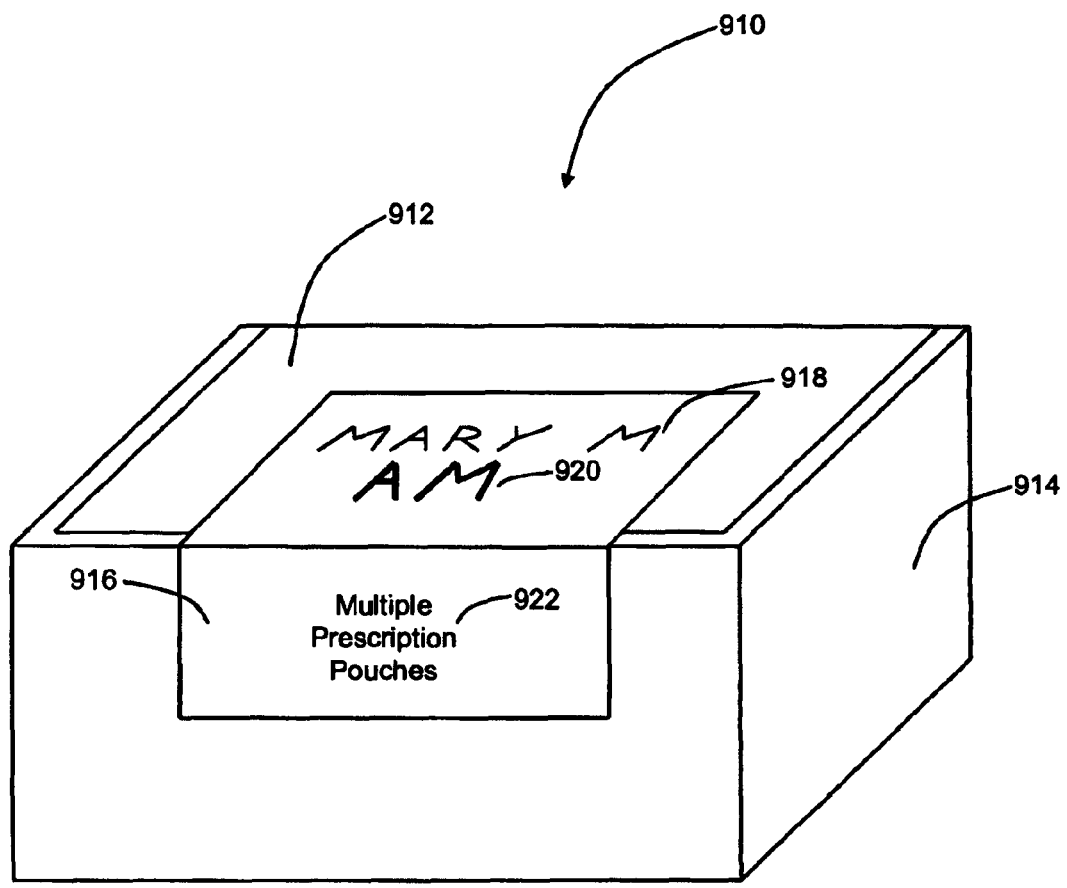

FIG. 43 shows a perspective view of an illustrative sealed outer box or "final package" for an alternative packaging assembly and apparatus.

Figure 44:
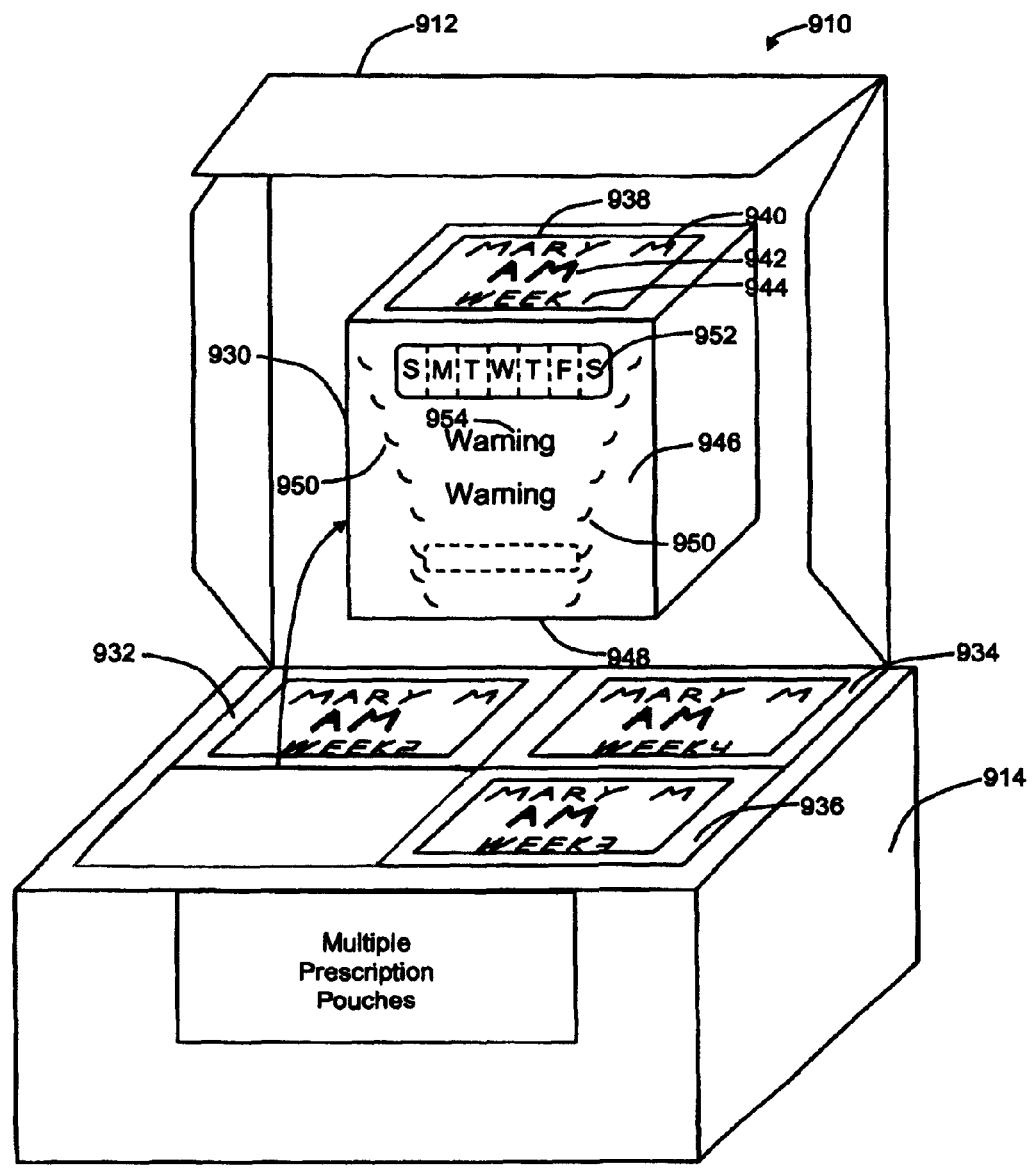

FIG. 44 shows the opened final package and a plurality of sealed containers or "primary packages" of FIG. 43.

Figure 45:
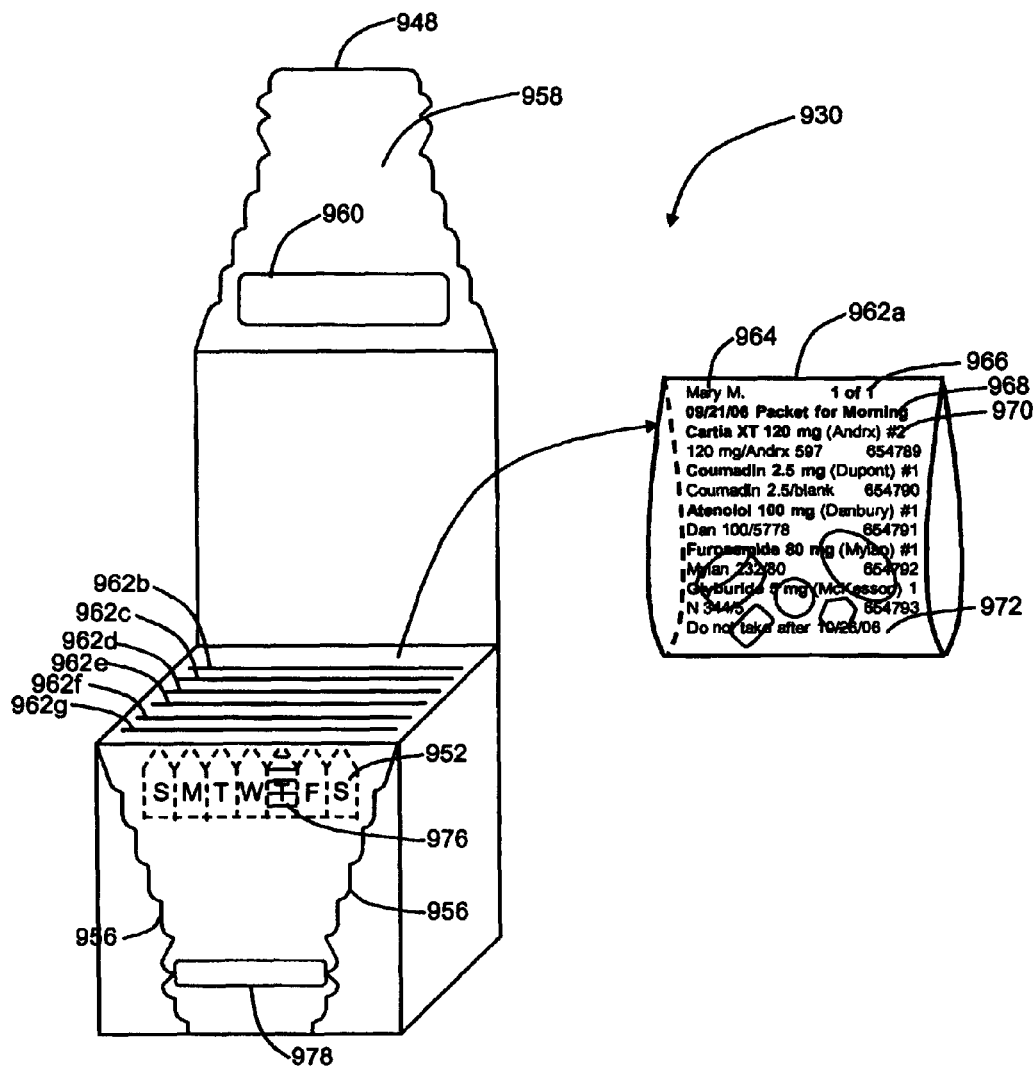

FIG. 45 shows a perspective view of an opened primary package housing a plurality of pouches.

Figure 46A:
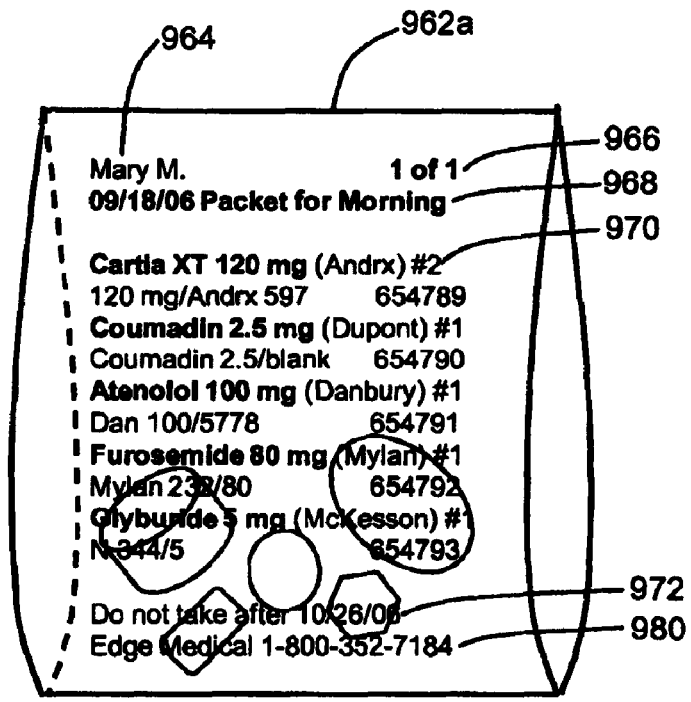

FIG. 46A shows an exploded view of an illustrative sealed pouch or "preliminary package" comprising a plurality of tablets associated with different medications.

Figure 46B:
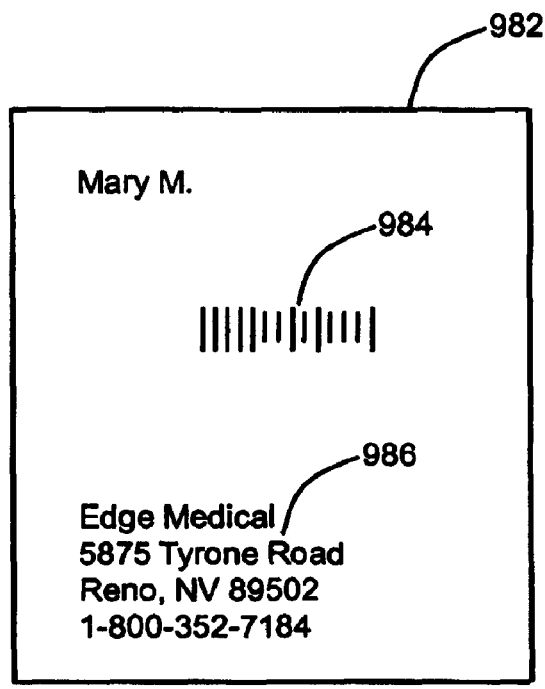

FIG. 46B shows a first illustrative label that is associated with a primary package.

Figure 47:
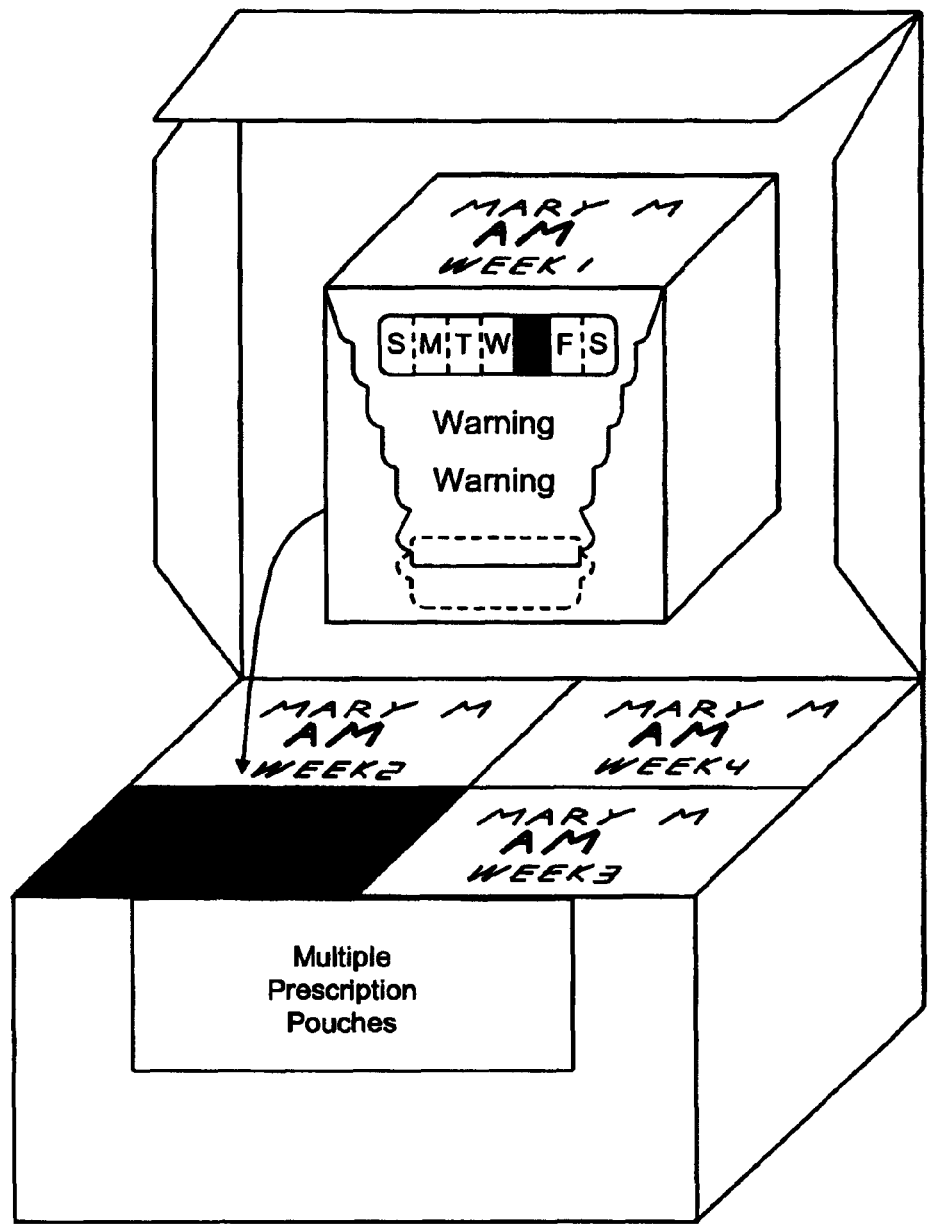

FIG. 47 shows a perspective view of the opened primary package being placed back into the final package.

Figure 48:
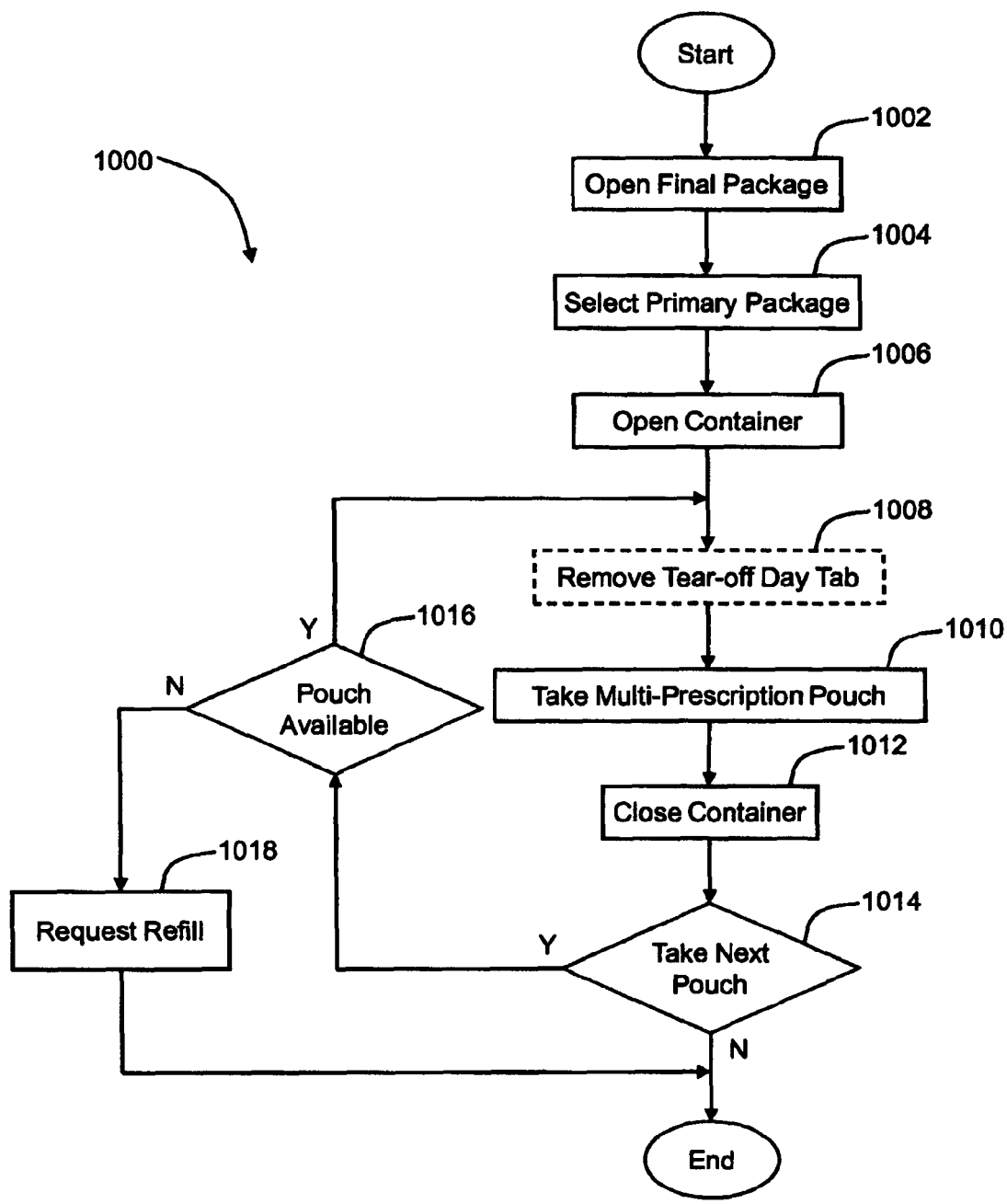

FIG. 48 is a flowchart that described the method for accessing a plurality of different medications.

Figure 49A:
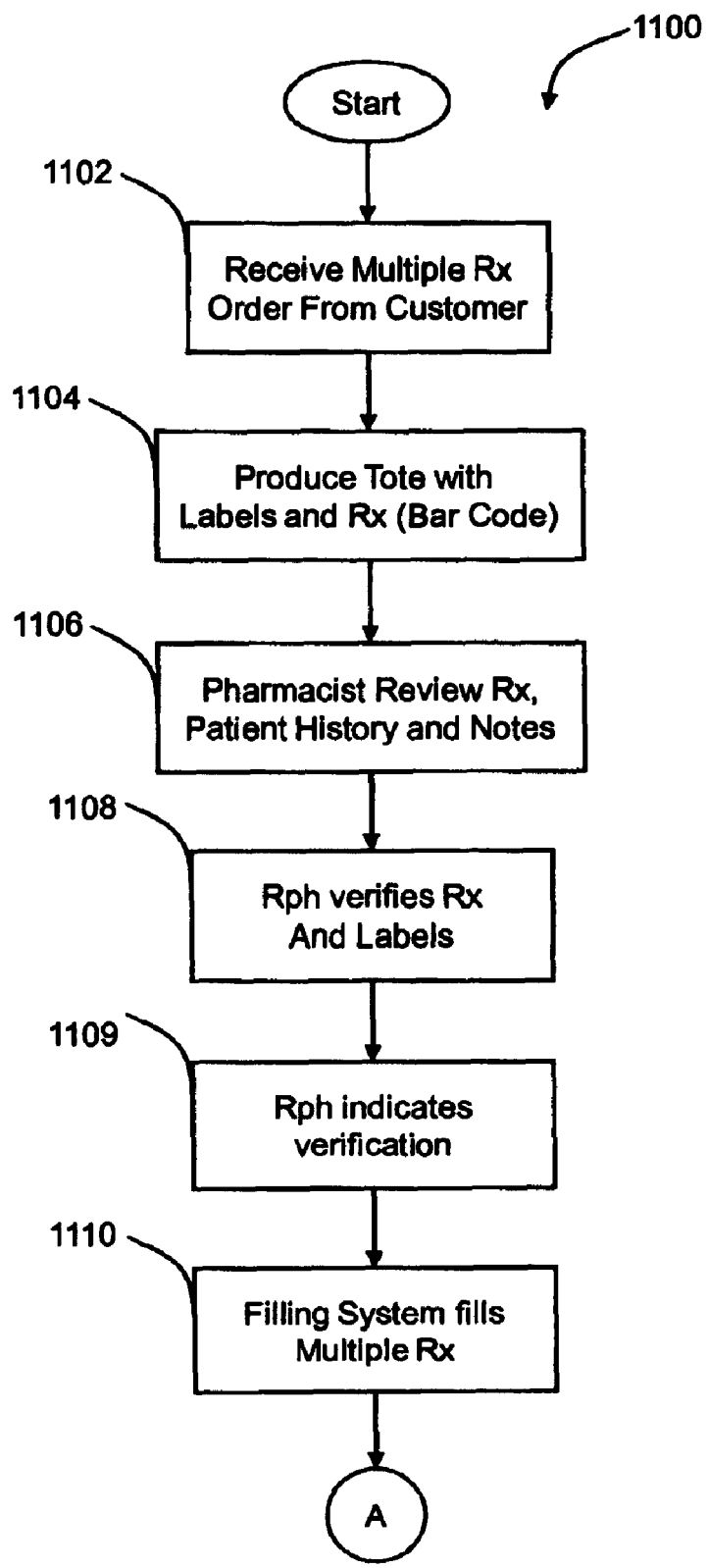
Figure 49B:
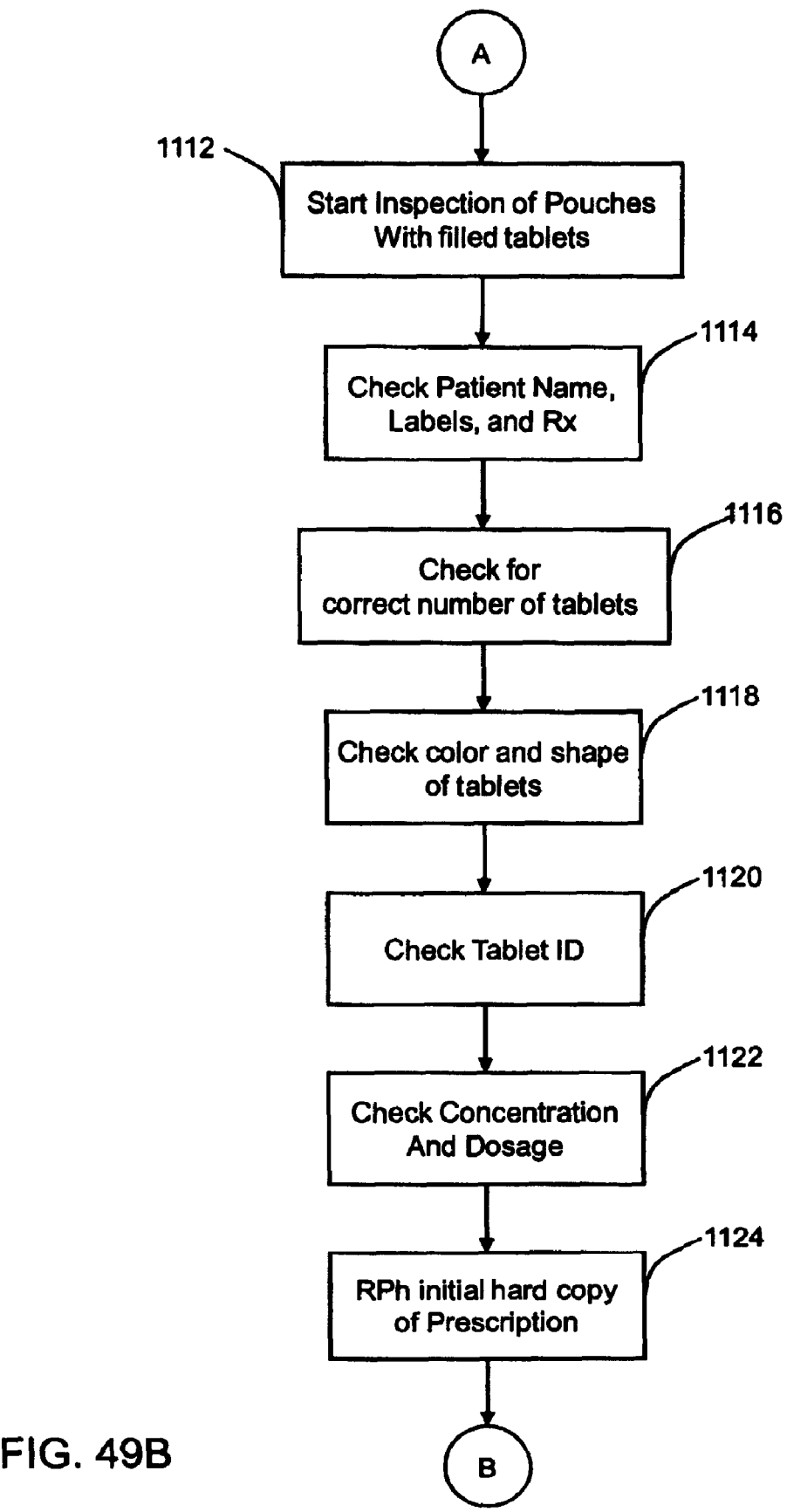
Figure 49C:
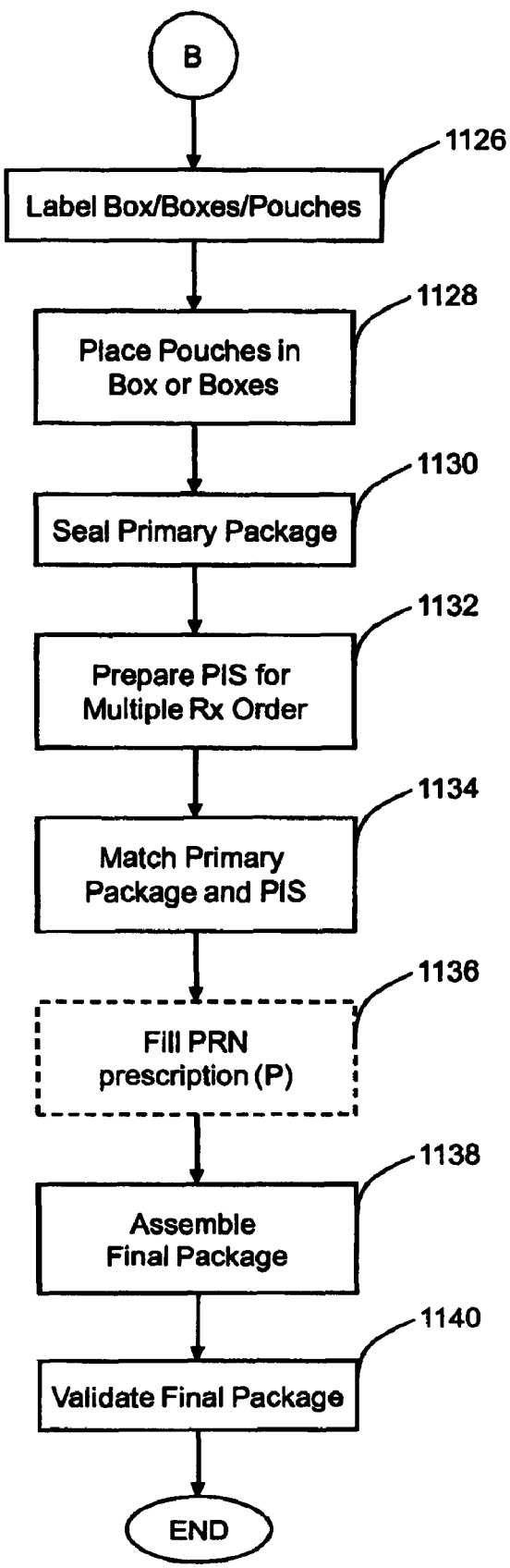

FIGS. 49A, 49B and 49C is an illustrative flowchart showing a method for the assembly of a primary package and a final package.

Figure 50A:
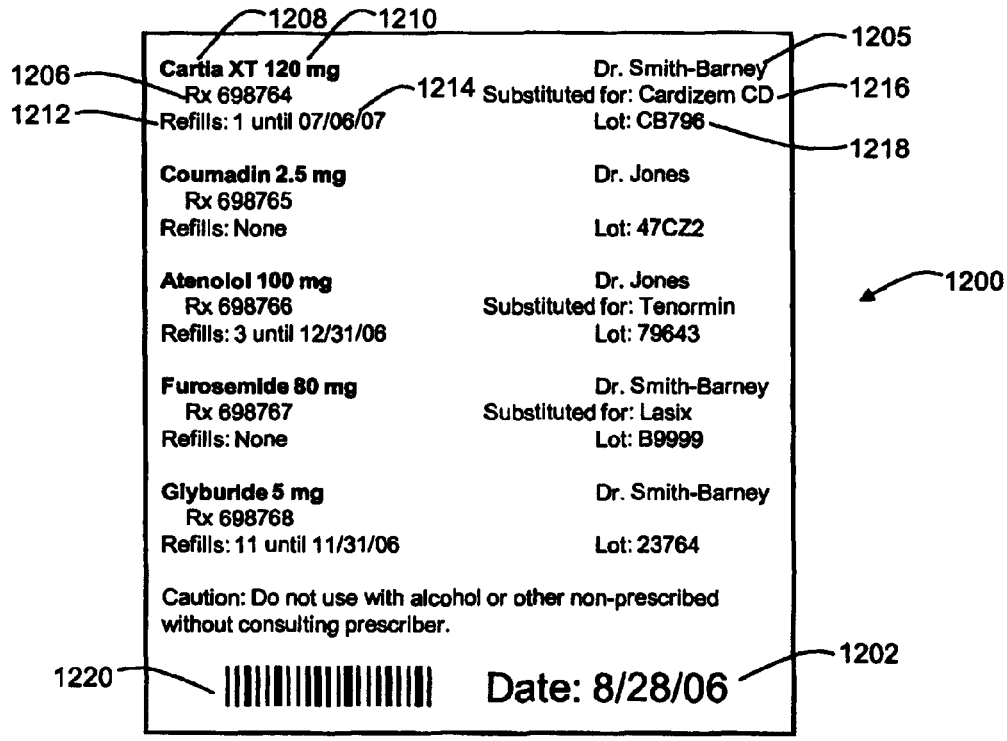
Figure 50B:
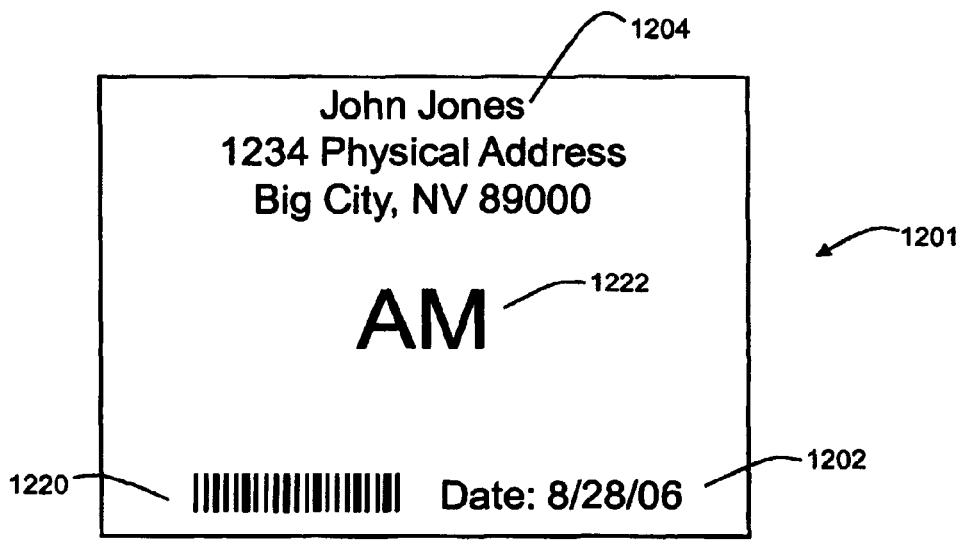

FIGS. 50A and 50B depict two illustrative labels applied to a primary package.

DESCRIPTION

Before the present assembly, apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Figure 1:
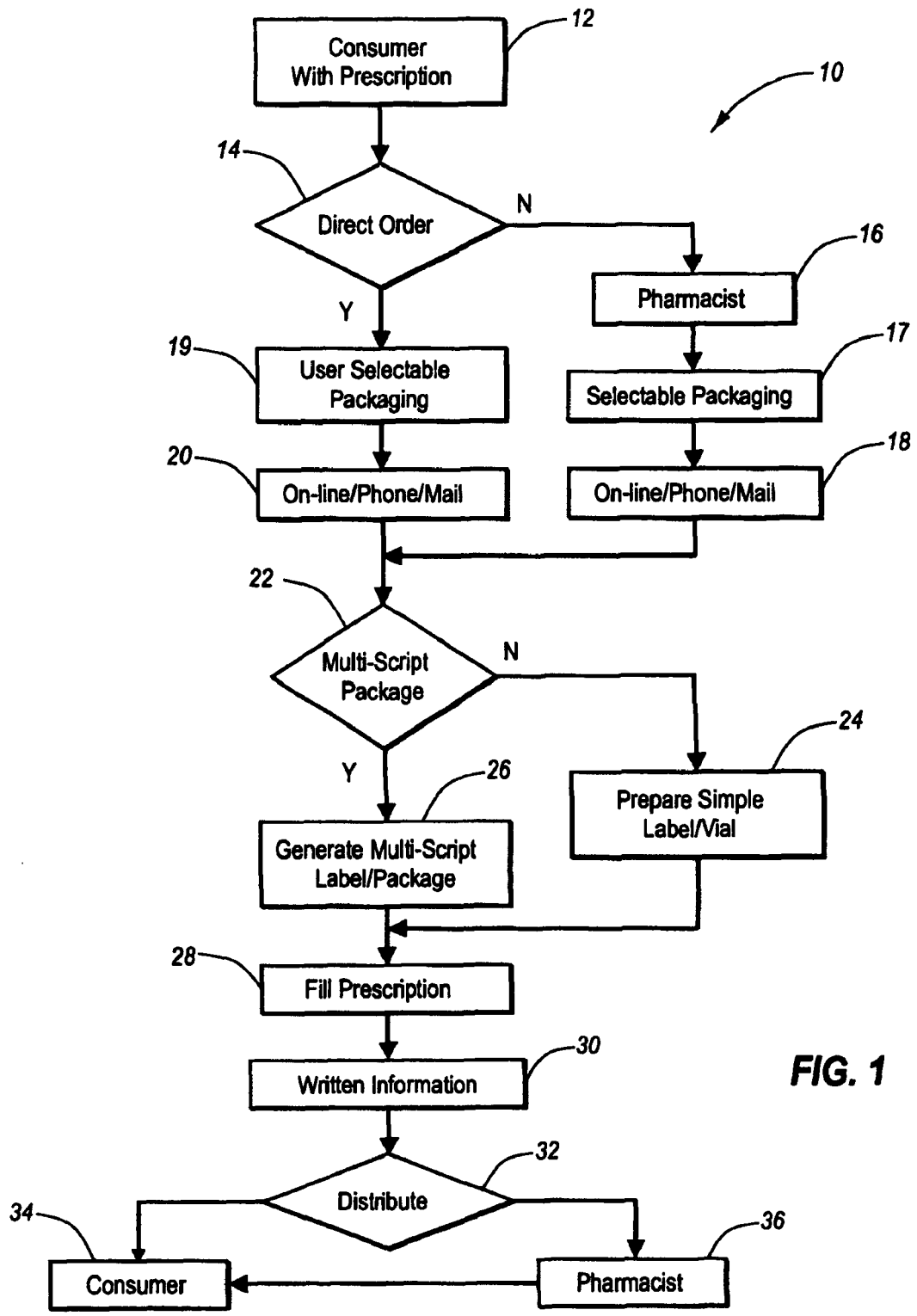
FIG. 1 is an illustrative flowchart showing a method for receiving and processing at least one prescription.

Referring to FIG. 1 there is shown a flowchart showing a general method for receiving and processing at least one prescription. A prescription generally comprises at least one medication that is dispensed as a tablet. The method may be initiated with a consumer having a doctor's prescription at block 12. By way of example and not of limitation, a consumer may be a patient or caregiver. A consumer may also be a person or entity authorized to conduct a transaction for at least one product that includes prescription medication, over-the-counter medication, vitamins, supplements, herbs, oils, or any such substances. A prescription may not be required for processing a prescription order. For example, a prescription may not be required for dispensing certain tablets such as vitamins, herbs, oils, over-the-counter medications, supplements, and other such products. Additionally, in some jurisdictions a prescription for dispensing medications may not be required.

A direct order may then be placed at decision diamond 14. A "direct order" is an order that must be placed by a pharmacist. By way of example and not of limitation, the order is placed using a graphical user interface (GUI) resident on a browser running on a computer that is in communication with the Internet by a pharmacist, patient or caregiver.

If the direct order requires a pharmacist, the method proceeds to block 16 where a pharmacist places the order for the appropriate medications. After block 16, the method proceeds to block 17 in which the pharmacist may be prompted for at least one packaging option. A variety of different packaging options may be provided to the pharmacist. The packaging options may comprise at least one multiple prescription container as described in further detail below. Alternatively, as described by block 18, the order may also be placed by telephone, fax, mail, scanned order, or any other such means for placing an order that does not employ a graphical user interface.

If the direct order can be placed without the need for a pharmacist, the method proceeds to block 19 where the user is prompted to select at least one packaging option. Generally, the user is either a patient or a caregiver. A variety of packaging options may be provided to the caregiver or consumer. The various packaging options are described throughout this specification. As described above, the order may also be placed on-line, by telephone, fax, mail, or other such means for communicating the order.

After receiving an order, the method proceeds to decision diamond 22 where a decision about how to process a multiple prescription order is made. A multiple prescription order or "Multi-Script" order is an order that comprises two or more tablets or medications wherein a first tablet or medication is different from a second tablet or medication. Generally, a multiple prescription order requires taking multiple tablets or medications at approximately the same time. If the order is not a multiple prescription order, the method proceeds to block 24, in which a single vial is prepared with a simple label. However, if the order is a multiple prescription order, the method proceeds to block 26 where a multiple prescription container is selected and the appropriate label is generated. At block 28, either the simple vial or the multiple prescription container is filled.

At block 30, a plurality of written information may also be generated. This plurality of information may include information related to each medication, summary information about each medication, appropriate labeling, some summary information about the patient, a drug interaction report, or any such combination thereof. The drug interaction report may provide information to help individuals properly take the prescribed medication. The drug interaction report includes information about the various drug interactions that may be associated with each prescription. For example, certain foods may interact with a particular prescription. Additionally, there may be a group of particular drugs that may interact with the prescription, and this information may not be readily available to the patient or the patient's caregiver. The drug interaction report may be used to help identify foods, medications, vitamins, supplements, or any combination thereof that may interact with the patient's filled prescription. The written information may also include a summary of the medications being taken as described in further detail below.

The method then proceeds to decision diamond 32 where a decision is made about how to distribute the filled order. If the filled order must be distributed to a pharmacist 36, the pharmacist 36 provides the prescription to the consumer 34 that may be a patient or caregiver. Alternatively, the filled prescription may be distributed directly to the particular consumer 34.

Figure 2:
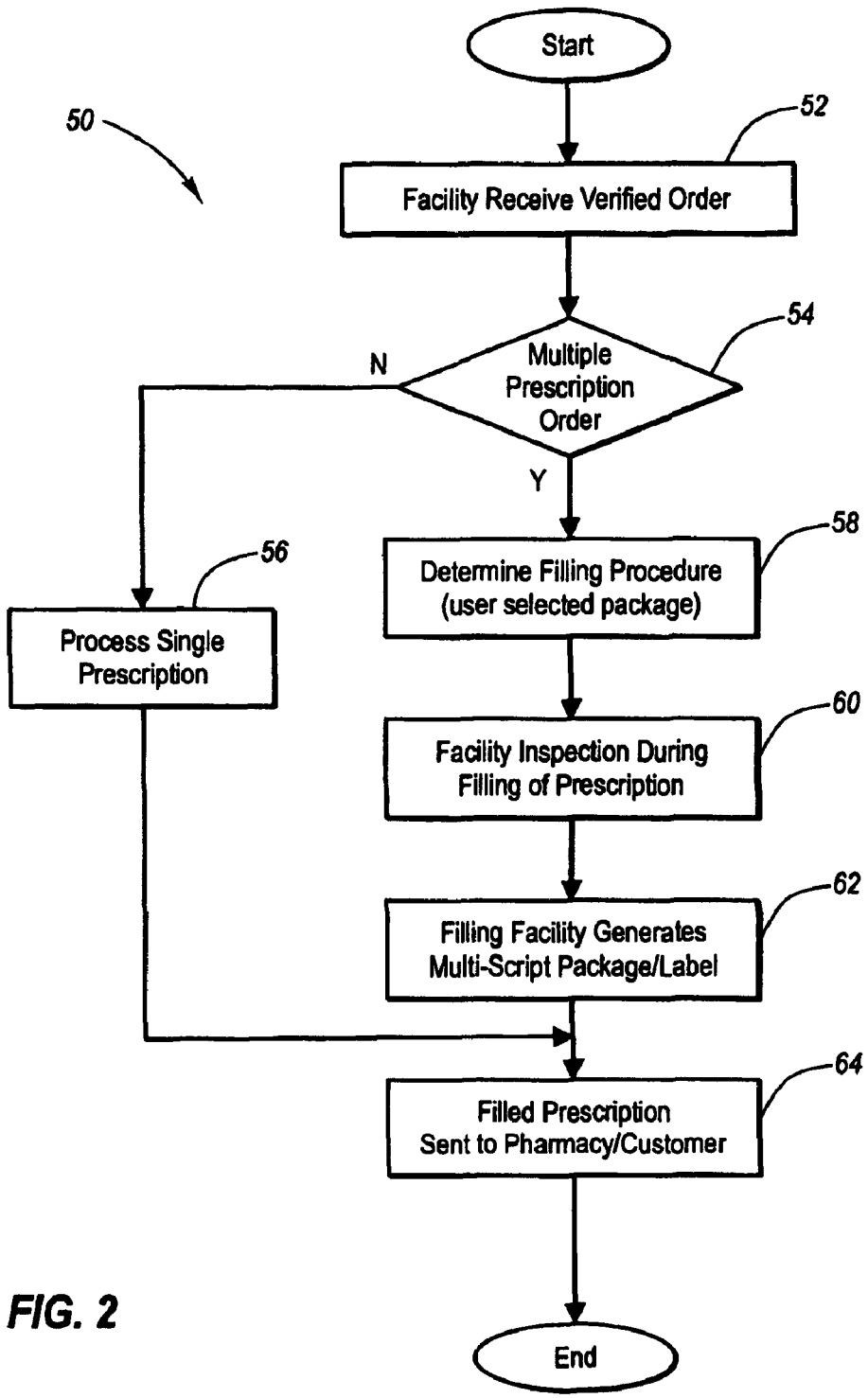
FIG. 2 is an illustrative high-level flowchart of a production facility processing a prescription order.

Referring to FIG. 2 there is shown an illustrative high-level flowchart of a production facility processing a prescription order. Recall, FIG. 1 describes a general method for receiving and processing a prescription order. FIG. 2 provides an illustrative flowchart from the perspective of a production facility processing a verified prescription order. The method is initiated at block 52 where the production facility receives a verified prescription order. A verified prescription order is an order that has been "verified" according to local jurisdictional requirements, insurance requirements, co-pay requirements, transactional requirements, or a combination thereof. For example, in certain jurisdictions a verified prescription order may require a medical doctor's signature, and may have to be processed by a pharmacist. Additionally, a verified order may require approval from an insurance company, Medicare or any such entity. In other jurisdictions, the only form of verification may include confirming that funds are available from the particular individual or organization charged, which satisfies transactional requirements. By way of example and not of limitation, verification of the availability of funds may include simply receiving authorization to charge a credit card and confirming that the credit card is a valid card.

The method then proceeds to decision diamond 54 where a determination is made if the verified order was a multiple prescription order. If the order is not a multiple prescription order, the method proceeds to block 56 where a single prescription order is processed, and then subsequently the filled prescription is sent to a pharmacy or customer as shown in block 64.

If the verified prescription order is a multiple prescription order, the method proceeds to block 58 where the facility determines the filling procedure to use. The filling procedure will depend on a host of variables such as the type of user selectable packaging. The method then proceeds to block 60 where the production facility inspects the tablets that have been placed in the multiple prescription containers. The type of inspection depends on the particular design of the production facility. For example the inspection may be conducted by tablet counters, RFID counters, by using X-ray or near IR technology, or other such technology capable of inspecting the multiple prescription containers. Alternative methods of inspecting the filled multiple prescription will readily suggest themselves to those of ordinary skill in the art.

After completing the inspection, the production facility generates the plurality of written information shown in block 62. The written information may also be referred to as packaging information. The written information may comprise information about each substance, appropriate labeling, summary information as described below, a drug interaction report as described in this specification, or a combination thereof. At block 64, the filled prescription order is then sent to a designated entity or individual including, but not limited to, the patient, the caregiver, the pharmacist, the user, or the consumer.

Figure 3:
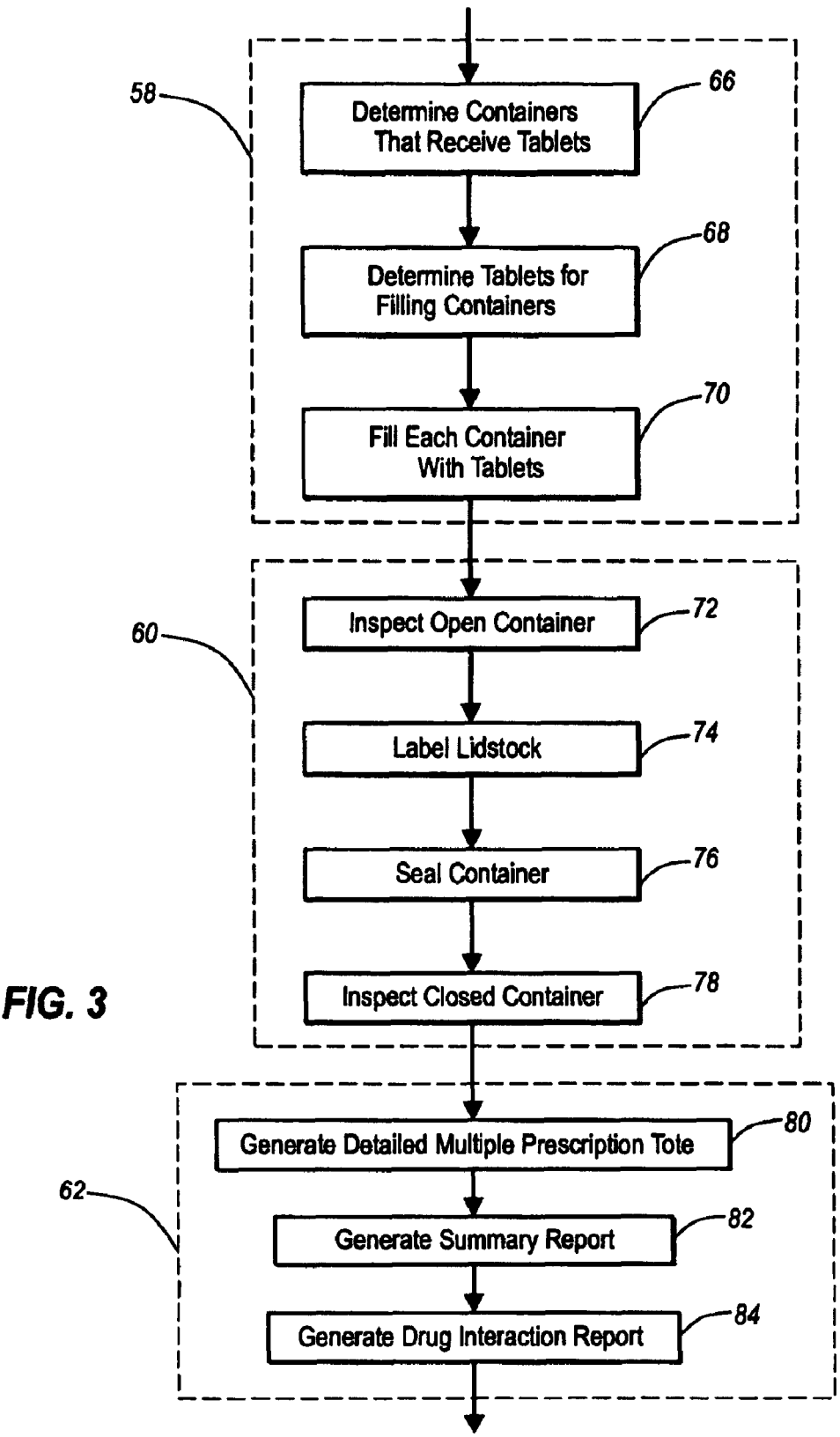
FIG. 3 is a more detailed flowchart showing how a multiple prescription order is processed within the production facility.

Referring to FIG. 3 there is shown a more detailed flowchart of a multiple prescription order being processed within the production facility. A more detailed view of block 58 is shown in FIG. 3, which includes a description of the user selectable packaging that may be determined by the user, consumer, patient, caregiver, or pharmacist. In the illustrative embodiment, a variety of different packaging options are presented. By way of example and not of limitation, the verified prescription order may include 10 tablets taken three times per day, which requires mid-size multiple prescription containers. In another example, the patient and/or user may desire a package design that may be easily used by a caregiver. In yet another illustrative example, the patient may want a package design that is small and portable. Based on the patients needs, the appropriate user selectable options may be provided. Thus, an individual requesting the filling of a multiple prescription order will provide sufficient information so that appropriately sized containers are identified as represented by block 66. The containers may be stacked. In certain embodiments, the containers may be placed on a conveyer belt system which allows the containers to travel along the conveyor system to the designated filler module containing the correct medications. The containers may also be placed on trays configured to hold a plurality of containers and situated on a conveyor system which allows the filling facility to track the position of each container within the filling facility.

Additionally, sufficient information is provided so that the appropriate tablets can be associated with the appropriate multiple prescription containers at the appropriate dosing times as represented by block 68. The method then proceeds to block 70 where each of the multiple prescription containers is filled with the appropriate tablets. A more detailed explanation of the method for filling each of the multiple prescription containers is described in further detail below.

A more detailed view of block 60 where the production facility inspects the containers is also described. The inspection may be conducted either before the multiple prescription containers are sealed as represented by block 72. A label may then be printed on lidstock 74 and the multiple prescription container may then be sealed 76. Additionally, the medications within the multiple prescription container may be inspected after the multiple prescription containers are sealed as represented by block 78. Thus, the filled multiple prescription container may be inspected either before the multiple prescription containers is sealed, after the multiple prescription container is sealed, or both.

A more detailed view of block 62 is also presented in FIG. 3 where after the inspection 60, the production facility generates the plurality of written information. The written information may also be referred to as packaging information. The written information may comprise information about each substance which is described in the multiple prescription tote 80. The written information may also include summary information about the various medications and is represented by block 82. A drug interaction report may also be generated at block 84.

Figure 4:
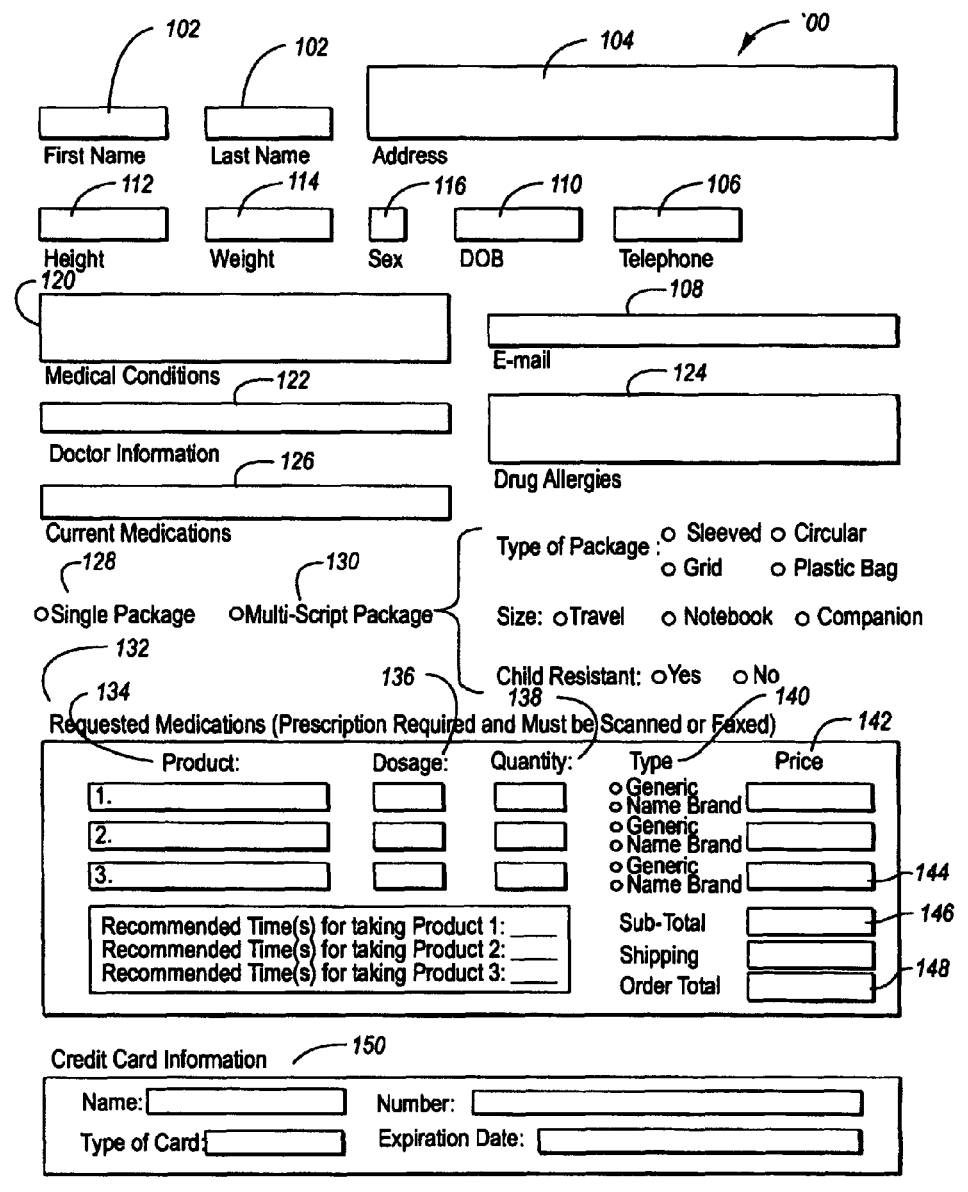

Referring to FIG. 4 there is shown an illustrative graphical user interface (GUI) for receiving on-line orders. The illustrative GUI 100 embodiment is configured to receive a prescription order, a direct order, or any such order related to medications, vitamins, supplements, herbs, oils, or any such substance that is associated with a particular patient. The illustrative GUI 100 includes fields for the name of the patient 102 and the patient's address 104. Additional information about the individual placing the order may also be requested, such as the individual's telephone number 106 and e-mail address 108. Information about the patient such as date of birth 110, height 112, weight 114, and sex 116 can also provided to the illustrative GUI 100. The user can input information about the patient's particular medical condition 120, information about the patient's doctor 122, allergies 124, and current medications 126 being taken by the patient.

Furthermore, the user may provide specific ordering options such as instructing about the type of user selectable packaging. For example, a plurality of single packages 128 may be requested for multiple medications. Also, a multiple prescription package 130 or "multi-script" package may be requested. The multiple prescription package may include a variety of user selectable options such as type of package, size of package, and child resistant packaging. The type of package may include a sleeved package or a circular package as described below. Alternatively, the packaging may employ other packaging techniques such as grid packaging or the use of plastic bags. The size of package may also vary and may come in three different sizes: travel (small), notebook (medium), and companion (large).

Data fields are also provided for identifying the requested medications 132 that include a description of the product 134, the dosage 136, the quantity 138, and the type of drug 140. The type of drug 140 may include information about whether the drug is generic or name brand. If the product is available, the on-line ordering system would then provide a price 142 for the product. A sub-total 144 is then provided, and shipping costs 146 are identified. A final order total 148 is then presented to the user. The patient may then provide a card 150 such as a credit card, a debit card or any other such information for conducting an on-line transaction. The name, the card number, the type of card and the expiration date of the card are requested in the illustrative embodiment.

Figure 5:
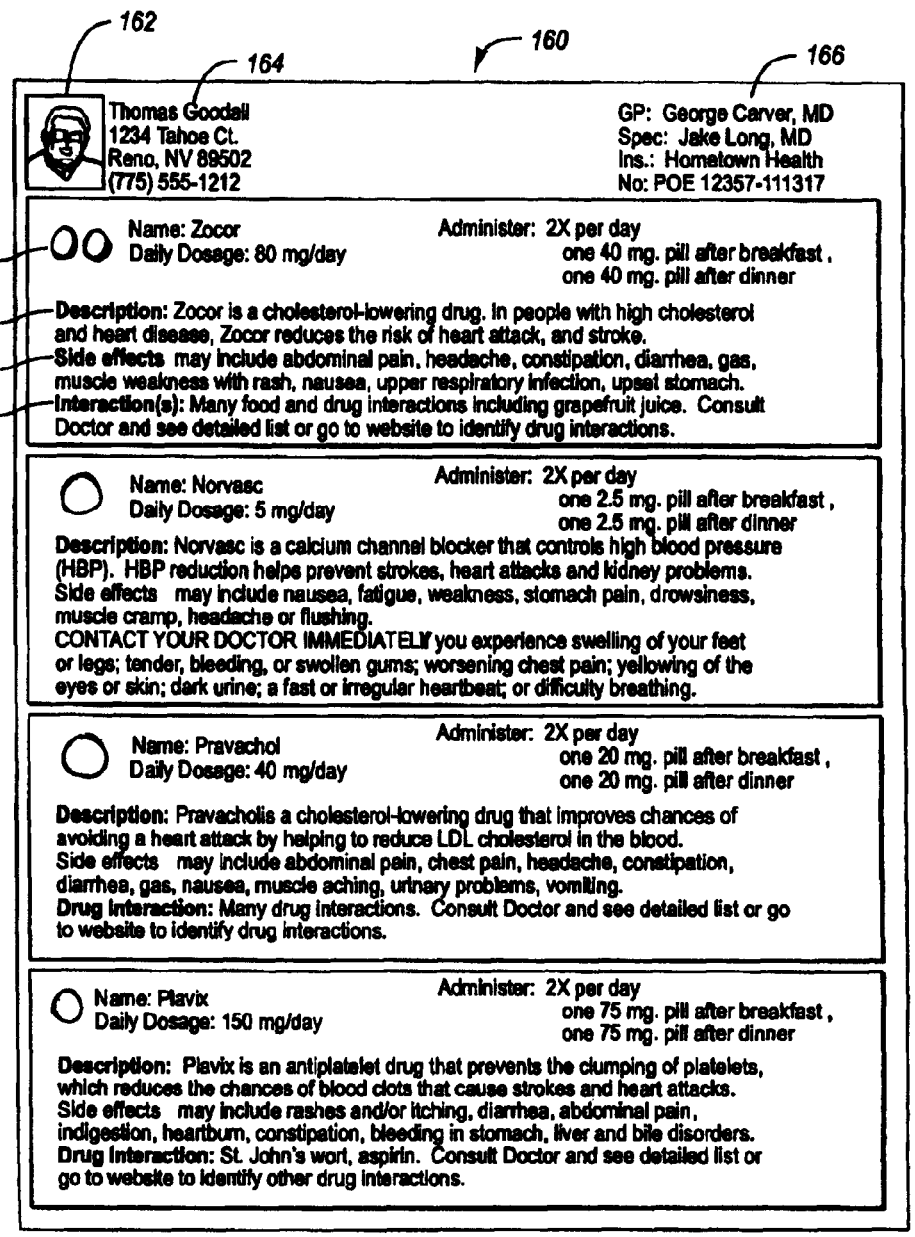
FIG. 5 shows an illustrative label that is generated by the production facility.

Referring to FIG. 5 there is shown an illustrative label that is generated by the production facility. By way of example and not of limitation, the illustrative label 160 may contain written information that is related to each medication such as summary information about each medication, summary information about the patient, the name of the patient, a picture of the patient, pictures of the first tablet and the second tablet that are to scale, a drug interaction description, or any combination thereof. The illustrative label may be folded and conveniently coupled to a multiple prescription container. For example, the illustrative label 160 can be coupled to a dispensing sleeve, which is described in further detail below.

The illustrative label 160 includes a picture 162 of the particular patient, and the name and address 164 of the patient. Furthermore, there may be additional unique information about the patient printed on the label, such as the doctor's name 166 and telephone number, and health insurance information. The label 160 also includes pictures 168 of the pills that have been prescribed. Additionally, there may be a particular description 170 about each pill on the folded label that may include manufacturer's latest labeling information, a summary of expected side effects 172, and a short description of possible drug interactions 174. This information may be presented in a manner similar to the Physician's Desk Reference, which includes a color picture of the pill with summary information about each pill. Additionally, information about how to administer products 176 may be provided. This information may be used by a caregiver, to help in dispensing the appropriate medications.

Figure 6:
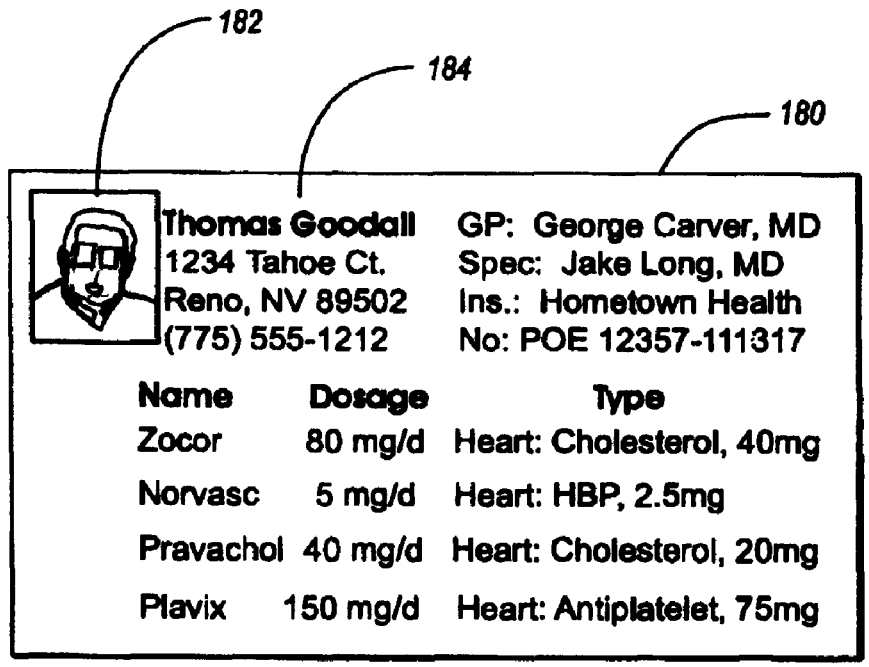
FIG. 6 is an illustrative summary label that may be generated by the production facility.
Figure 7:
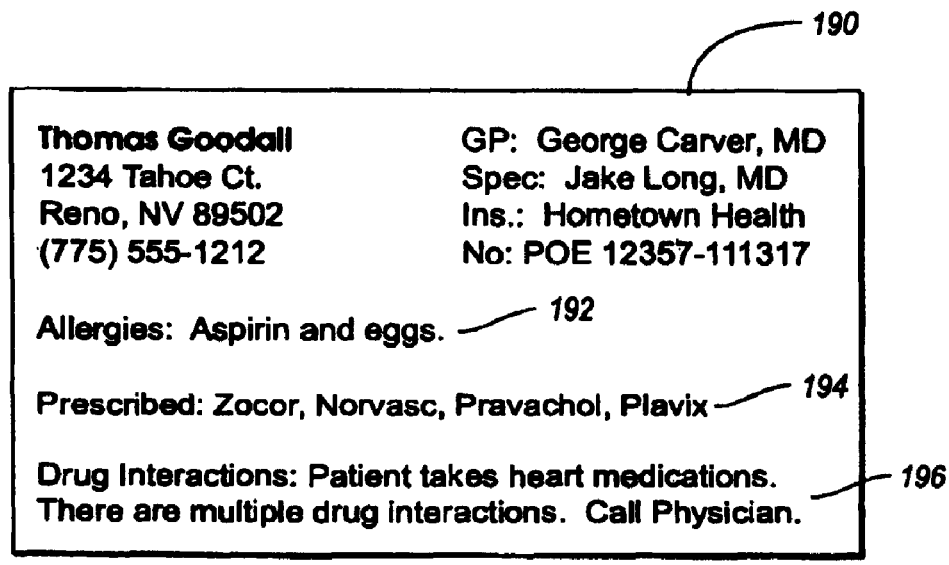
FIG. 7 is an alternative summary label that may be generated by the production facility.

Referring to FIG. 6 and FIG. 7 there is shown two different summary labels that may be generated by the production facility. In FIG. 6, the summary label 180 may be conveniently configured to fit into a wallet, or may be configured to be attached to the back of an insurance card or driver's license. The illustrative label 180 comprises a picture 182 of the patient, pictures of the first tablet and the second tablet that are to scale, his name and address 184, and other such information. Information about the prescriptions and dosages may be provided with information about the patient's doctors and other health information. In FIG. 7 an alternative summary label 190 is shown that includes the patient's name, name of the patient's doctors, insurance, and insurance number. Additionally, summary label 190 includes information about the patient's allergies 192, the patient's prescriptions 194, and a warning about possible drug interactions 196. The particular summary label may be dependent on the patient's condition, the patient's caregiver, a physician's recommendation, statutory requirements, or any other such entity charged with assisting the patient.

FIG. 1 through FIG. 7 provides an overview of the systems and methods for processing a multiple prescription order. In the illustrative embodiment an emphasis was placed on performing an on-line transaction. The on-line systems and methods for processing the prescription order are described in further detail in FIG. 8 through FIG. 12. These on-line systems may be open and use the Internet or may be networked using alternative networking architectures as described below.

Figure 8:
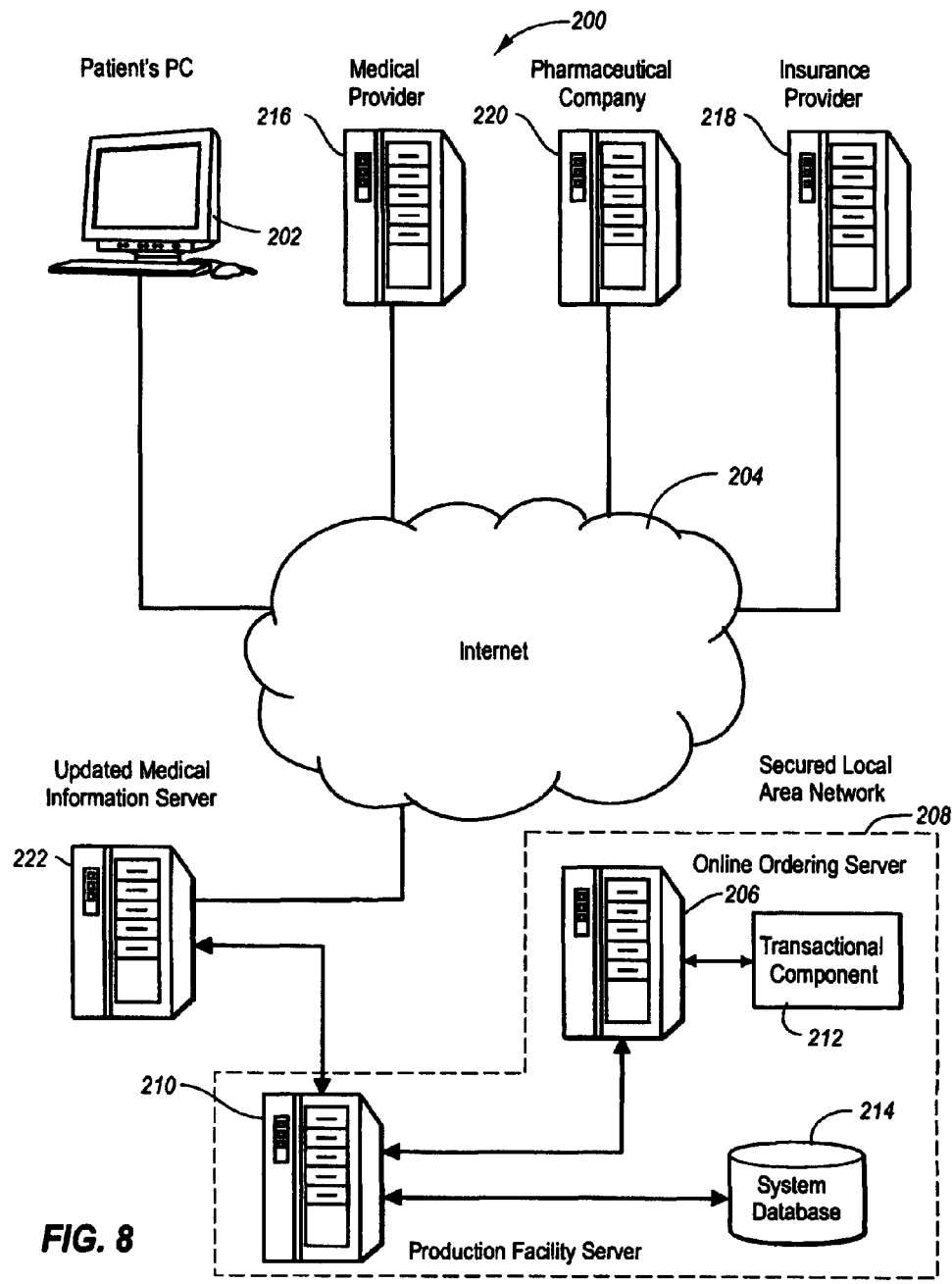
FIG. 8 is a block diagram of an illustrative system that receives a pill order via the Internet.

Referring to FIG. 8 there is shown a block diagram of an illustrative system 200 configured to receive a pill order via the Internet. The illustrative patient's personal computer (PC) or "client" 202 displays the illustrative GUI 100. The illustrative client 202 is communicatively coupled to the Internet 204. By way of example and not of limitation, a standard off-the-shelf personal computer and operating system would operate as a client.

The PC 202 is configured to remotely communicate with an online ordering server 206. The online server 206 is behind a firewall and is part of a secure local area network (LAN) 208 located at a production facility. Generally, the production facility is configured to generate a filled multiple prescription order as described throughout this specification. The secure LAN also comprises a production server 210. In the illustrative example of FIG. 8, the production server 210 and online server 206 are both housed in the production facility. An alternative embodiment in which the online server is located in a separate location is described below in FIG. 9.

The online ordering server 206 is communicatively coupled to the production server 210. The online ordering server 206 is configured to communicate with the user and/or clients that are placing the on-line order. The ordering server 206 also contains the hardware and software necessary for addressing queries about inventory in the production facility. The online server 206 may be configured to query the user about a particular prescription, about health insurance, and other pertinent information. The online server 206 may comprise software and hardware that permits the client 202 to pull up notes, research the prescribed medication(s), research side effects and drug interactions with other medications, vitamins, foods, and other such information that would help the patient properly consume the products ordered by the patient.

The production server 210 controls the processing of the multiple prescription orders at the production facility that generates containers having a plurality of different tablets in each container. The illustrative production server 210 comprises a system database 214 that stores information about the products available at the production facility such as prescription medication, over-the-counter medication, vitamins, supplements, herbs, oils, or other such substances. Additionally, the system database 214 may include historical prescription information that is associated with the patient, so that the user may access the multiple prescription order at a later time. In one illustrative example, the production server contains and maintains all the information to control the production facility. The production server 210 may be configured with management software that manages all the filling, inspection, printing, sealing, order tracking, and tablet assembly traffic control functions.

While placing an order, the online ordering server 206 may request information from a medical provider server 216 or provide information to the medical provider. For example, a medical provider such as a medical doctor or nurse can confirm that a specific medication has been ordered and will be administered in a particular manner. Additionally, the medical provider may also include notes for the patient on how the medicine should be taken, and this information may be printed by the production facility and associated with the patient's on-line order. Additionally, historical prescription order information may also be stored on the medical provider server 216.

The online ordering server may also request information on the accuracy or changes in the end user's medical insurance from the insurance provider server 218. The online ordering server 216 may also request information from the pharmaceutical company server 220 about certain prescribed medications. These queries to the pharmaceutical company server 220 may occur during the online ordering process initiated by the end user or at various times when updating the system database. Additional queries may be made to government agencies, private medical facilities, on-line search engines, websites, databases, or any combination thereof.

The online ordering server 206 and/or the production facility server 210 may also be communicatively connected to an updated medical information server 222 via the Internet or a secure wide area network connection. The updated medical information server 222 may be a private or government maintained server with compiled updated information on the various drugs stored in the production facility. The updated information may comprise new warnings on drug interactions, updated expiration dates, toxicity information and the like. The updated information is communicated to the second labeling component. This information is valuable in assuring the multi-drug prescriptions are effective and safe.

Additionally, the online ordering server 206 comprises a transactional component 212 that processes the user's financial information. The transactional component enables the online ordering server 206 to obtain pertinent information from the user, healthcare provider and the user's insurance company to verify the prescription. The transactional component is also configured to carry out the payment of the order and informs the user if the prescription has been processed or if the financial transaction has failed.

Figure 9:
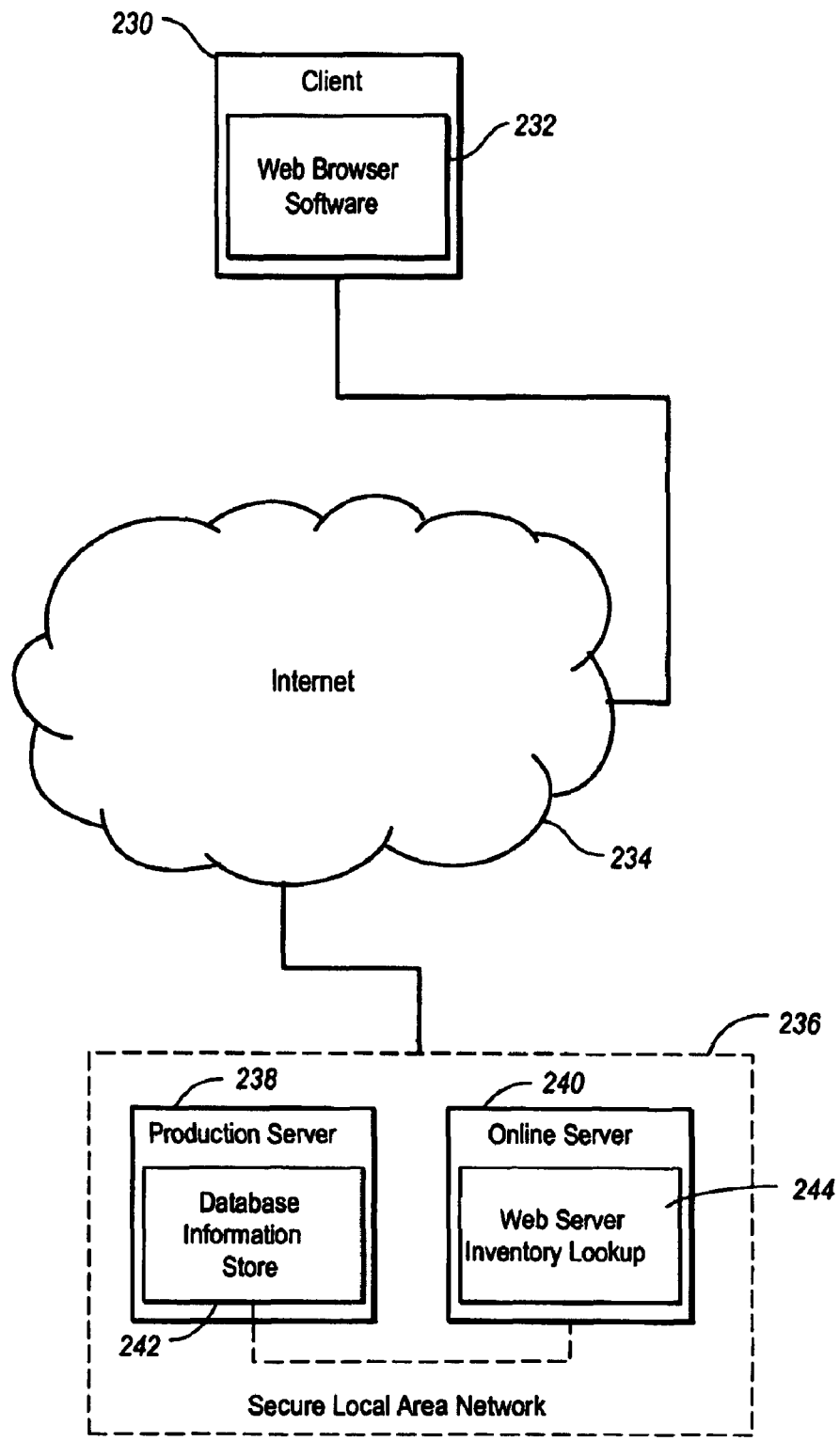
FIG. 9 is a block diagram of a client server architecture that out-sources the filling of the multiple prescription order to a production facility.

Referring to FIG. 9 there is shown a block diagram of a simplified client server architecture in which the multiple prescription packaging is outsourced to the production facility. In this embodiment, the user requests a prescription refill from a client 230 computer that displays a GUI viewed using a standard web browser 232, and the client 230 is communicatively connected to a wide area network (WAN) such as the Internet 234. The client 230 then proceeds to access the web site that displays the illustrative GUI 100. The client 230 computer may be a portable terminal, a notebook computer, a hand-held personal digital assistant, or other such device that can be networked and can process browser software. It shall be appreciated by those skilled in the art that the end user of the GUI may be a patient, parent, caregiver, physician, hospital personnel, or any other person that has permission from the patient to access their prescription data.

The client 232 then proceeds to communicate with the secure LAN 236 that comprises a production server 238 and an online server 240. The production server 238 is associated with managing the inventory in the production facility and comprises an inventory database module 242 that determines if the production facility can satisfy the client's prescription order.

The online server 240 may be located in a variety of different places such as a separate on-line pharmacy, a physician's website, a healthcare provider's website, a health insurance website, a school, a university, or any other such entity that out-sources the multiple prescription packaging to the production facility described in further detail below. In the illustrative embodiment, the online server 240 comprises a web server inventory lookup module 244 that is operatively coupled to the inventory database module 242 and receives updates regarding the production facility's ability to satisfy the client's request.

In operation, the client 230 may access the production server 238 directly or through the illustrative online server 240 that may be associated with a separate on-line pharmacy, a physician, a health care provider, a health insurance provider, a school, a university or any other such entity. Additionally, physicians involved in the patient's care may utilize the Internet to generate a new prescription for the patient, or modify a previous prescription that may be stored on the production server 238.

Patient confidentiality may be preserved by using encryption technology and by requiring strong authentication. Using encryption technology such as Secure Sockets Layer (SSL) and Public Key Infrastructure (PKI), communications across the Internet 204 are kept secure. Illustrative embodiments may use available encryption tools such as Pretty Good Privacy (PGP), OpenPGP (the IETF's RFC 2440) and other available PKI encryption standards. Information stored on databases and servers may also be encrypted. Strong authentication may be obtained by asking the user for one or more unique identifiers such as date of birth (DOB), unique IP address, last 4 digits of a social security number, username, password, or any other such unique identifier.

Once the client 230 has been authenticated, the client is able to place a multiple prescription order using the illustrative graphic user interface (GUI) 100. In one illustrative example, a pharmacist's on-line server communicates with the production server 238 and the inventory database 242. The pharmacist's on-line server makes a request to determine whether the production facility can satisfy the pharmacist's order. The inventory database 242 is accessed to determine if the prescription order may be filled. Once the pharmacist's online server has received confirmation that the prescription order can be filled, the online server relays this information back to the clients computer via the Internet.

By way of example and not of limitation, the illustrative production server 238 comprises software to access the drug interaction database to determine if there may be possible interactions between the prescribed tablets stored. The production server 238 also communicates the order to production facility computers which control the various systems and subsystems involved in producing the tablet assembly, including printers for labeling the lidstock on each individually sealed container with medication instructions such as date and time to take the tablets in each individual container. The production server 238 may also communicate to production facility computers which are connected to a printer for labeling an area of the sleeve portion of the tablet assembly, with end user information, drug information and expiration date(s) for the medication stored within the individual containers. It should be noted that vitamins and herbal supplements may also be stored together with prescription drugs.

Figure 10:
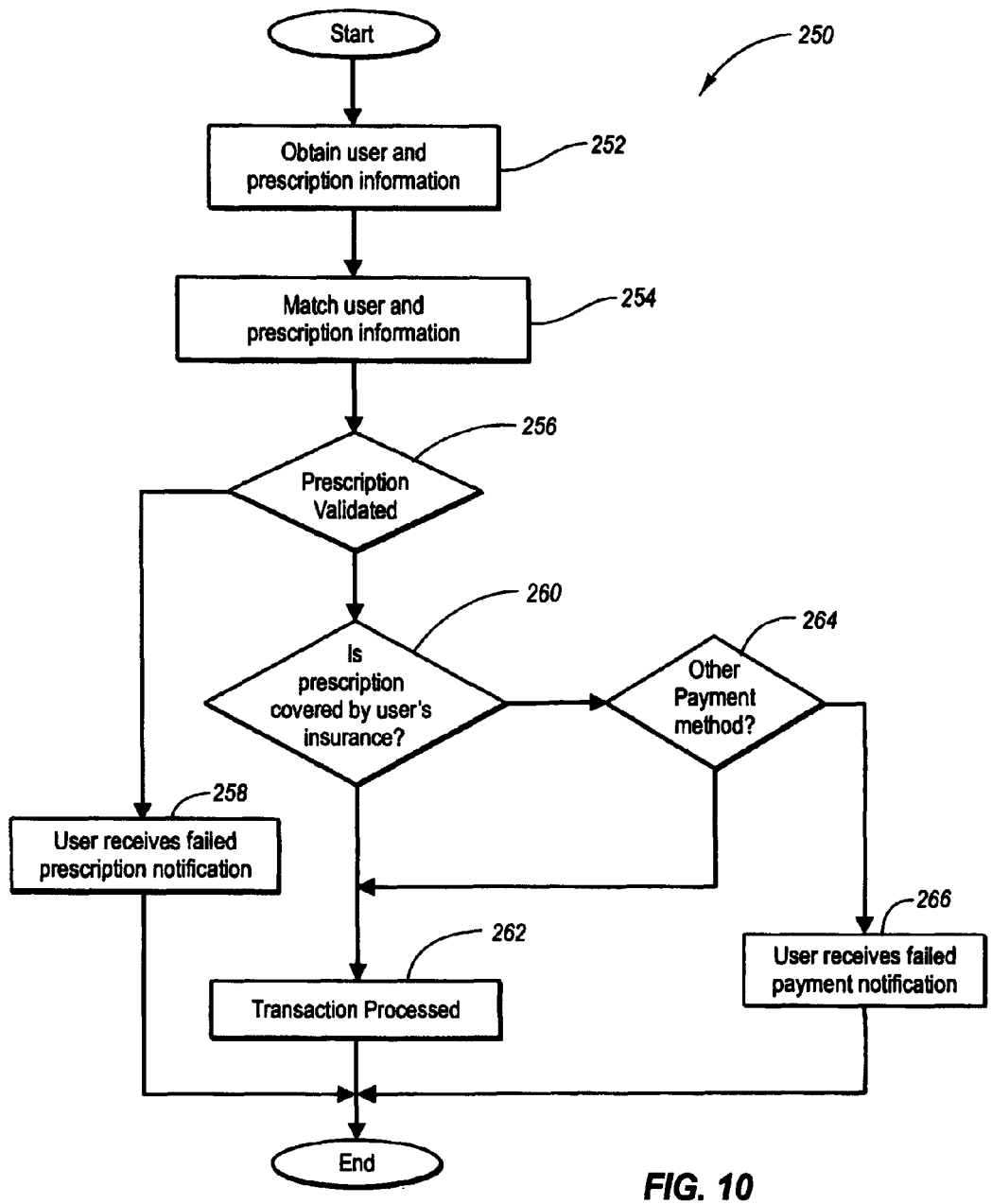
FIG. 10 is a flowchart showing a prescription validation process.

Referring now to FIG. 10 there is shown a flow chart of an illustrative prescription validation process 250. The prescription validation process is initiated at block 252 where user information and prescription order information is provided to either online server 206 or online server 240. The method then proceeds to block 254 where user information is matched against the prescription order information.

At decision diamond 256, the prescription order is validated if user information and prescription information also match information stored on the online server. Additionally, the prescription may be validated after the online server communicates with another server such as the medical provider's server. Alternatively, the prescription order may be simply validated if the user information matches the prescription information. For example, if either the patient information or the prescription order information does not match the information stored on the online server, then the method proceeds to block 258 where the user receives a failed prescription notification. By way of example and not of limitation, an explanation may be provided by the online server such as the patient's personal information is incorrect, or the prescription has expired, or a physician's examination is required before filling the order, or the patient needs to wait a couple more days before the prescription order may be filled. Those skilled in the art shall appreciate that the user information and prescription information may require being input more than once before a failed notification is provided to the user.

If the prescription order is validated by having the patient information match the prescription order information, the method proceeds to decision diamond 260 and determines if the prescription order is covered by the user's health insurance. As with prescription information, the insurance information for a specific user may be stored on a database associated with the online server of the production facility or the health insurance company's server may be queried by the online server via secured network about the accuracy of the user's insurance policy such as determining if the insured's policy is up-to-date. Additionally, information about the medications covered by the specific insurer may be queried, co-payment information, prescription drug policy, secondary insurance information, or any other such pertinent insurance information.

If the prescription order is paid for partially or fully by the user's health insurance, the method proceeds to process the transaction at block 262. A more detailed view of the transaction process 262 is provided below in FIG. 11.

The prescription order may not be covered, or may only be partially covered by the user's insurance and so the method proceeds to decision diamond 264 where alternative payment methods can be provided. By way of example and not of limitation, alternative payment methods include VISA transactions, debit card transactions, ATM transactions, PayPal transactions, Electronic Fund Transfers, and other such methods for performing on-line transactions. If the alternative payment method can be processed, the method proceeds to block 262 where the transaction is processed. However, if the alternative payment method cannot be effectively processed, the method proceeds to block 266 where the user receives a failed payment notification.

Figure 11:
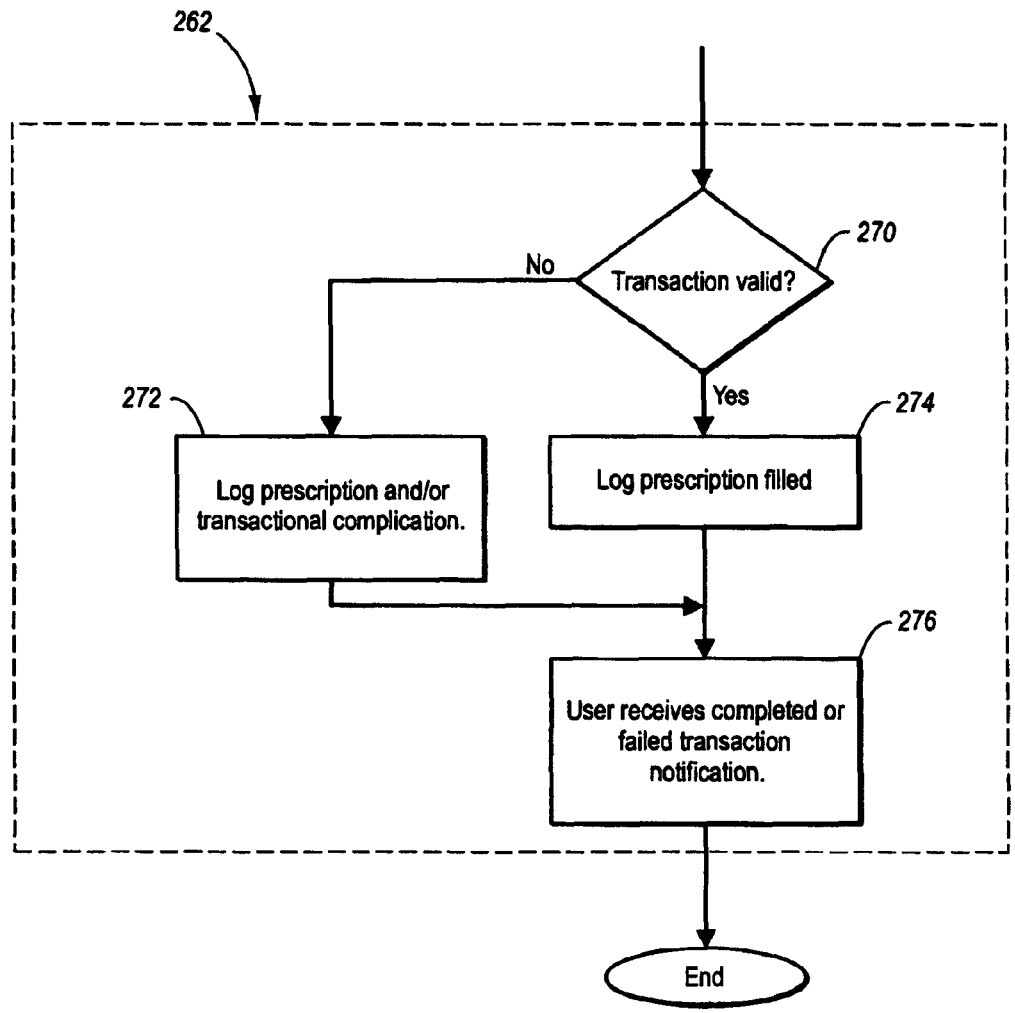
FIG. 11 is a flowchart showing a transaction being processed.

Referring to FIG. 11 there is shown an illustrative method for processing an illustrative transaction in block 262. At block 262, the online transaction is processed, which enables the online server to send confirmation that the prescription order has been filled. The method is initiated at decision diamond 270 where a determination is made concerning whether the transaction is valid. A transaction is valid when the information for payment of the multiple prescription order has been authenticated.

If a determination is made that the transaction is not a valid transaction, the method proceeds to block 272 where a log of either the prescription complication, transaction complication, or both is recorded. The prescription complication may arise because the production facility can not satisfy the order. The transactional complication may be caused by the payment method not being authenticated.

If the transaction is valid, the method proceeds to block 274 where the log indicates that prescription has been filled. The processing of the online transaction may also comprise confirming that the drugs requested are in the production facility's inventory and ready for dispensing. Inventory information may be stored on either the online server or the production server or on any other communicatively connected database or computer associated to the transaction component of the online server.

After determining whether the transaction is valid, the method proceeds to block 276 where the user receives a completed or failed transaction notification. In the illustrative example, the failed transaction notification comprises information explaining to the user that the transaction failed because an invalid credit card number was provided. If the transaction is determined to be valid, the prescription is logged as filled and the user receives a prescription completed notification via the network connection between the online server and the user's computer.

A multiple prescription container assembly comprises a plurality of containers that are configured to receive a plurality of medications, even though a single prescription may reside within an individual container. The multiple prescription container assembly is configured to dispense a plurality of different tablets to a particular individual. The illustrative multiple prescription container assembly comprises a plurality of containers made from a single piece of moldable material wherein the containers are ordered to permit sequential dispensing. At least one of the containers is configured to receive a first tablet associated with a first medication, and a second tablet associated with a second medication that is different from the first medication, the first tablet and the second tablet to be taken at approximately the same time by the particular patient. As described above, there is a flange on the top surface of each of the containers. The multiple prescription container assembly also comprises a plurality of lids, the lidstock configured to interface with the flange of each integrated container. Each lid seals each of the containers and has a surface that receives a printable indicia with specific information regarding the particular individual. Additionally, the multiple prescription assembly comprises a sleeve that is slidably coupled to the plurality of sealed containers wherein the sleeve is configured to permit sequential dispensing of each of the sealed containers.

Figure 12:
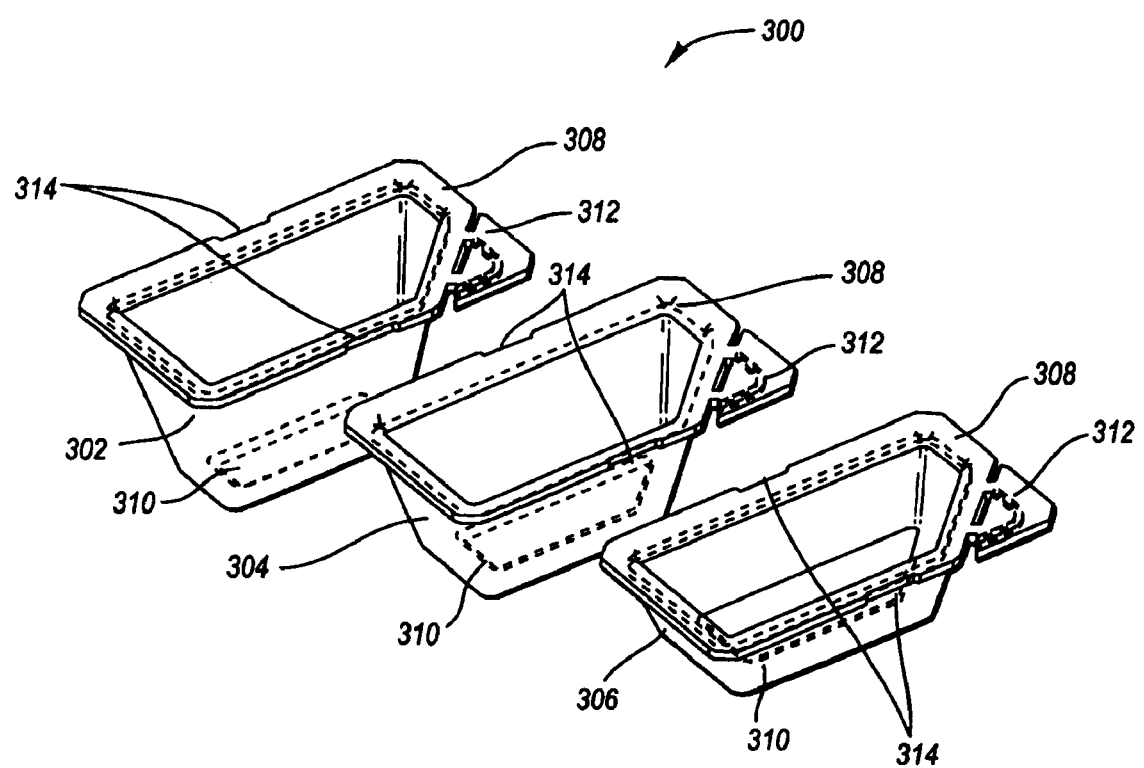
FIG. 12 is a diagram showing an illustrative multiple prescription container having various depths.

Referring to FIG. 12 there is shown a plurality of illustrative containers 300 having various depths that are configured to receive a plurality of tablets. The three individual containers 302, 304, and 306 are identical except for the depth of the cavity of the containers. The flanged top surface 308 and the bottom surface 310 are the same on all three containers shown in FIG. 12, and are configured to make the various sizes of containers stackable. Each of the containers further comprises a breakaway tab 312 on the sealing flange 308. The tab provides a handhold for easy opening and peeling back the lid from the container. Each of the containers also comprises a plurality of indentations 314 on at least one edge of the flanged top surface 308.

Each of the illustrative embodiments 302, 304 and 306 is an element of the multiple prescription container that stores tablets. It should be noted that a "tablet" is a small article which is swallowed. A tablet includes tablets, capsules, and caplets. A tablet may also be a solid dose of medication, i.e. pill, tablet, capsule or a liquid dose of medication, e.g. Vitamin E or (cod liver oil) provided in a capsule. In general, a tablet may be a prescription medication, supplements, or any other such article that is intended to be ingested to improve a user's health or wellbeing. A tablet may also be medication in the form of a suppository, or vitamins, herbal supplements and the like.

Figure 13A:
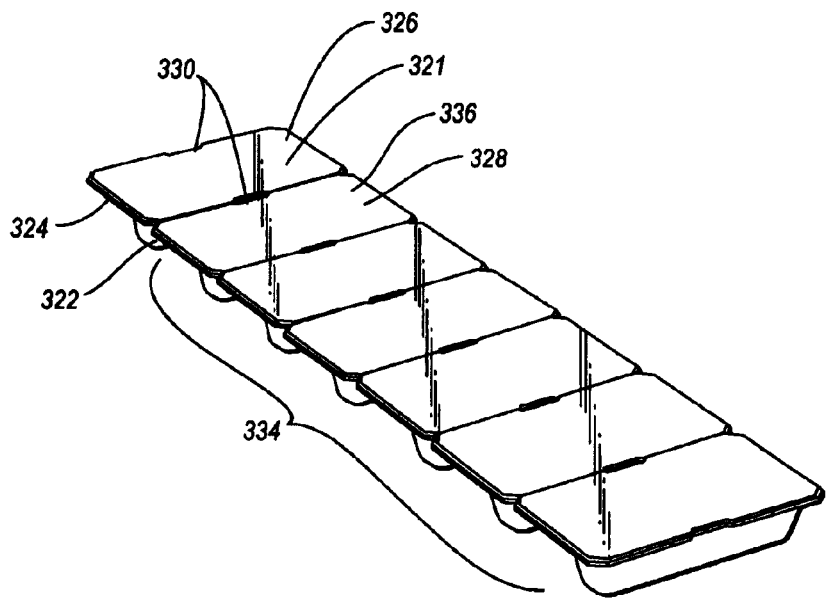
FIG. 13A and FIG. 13B shows a top view and a bottom view of a multiple prescription container assembly.
Figure 13B:
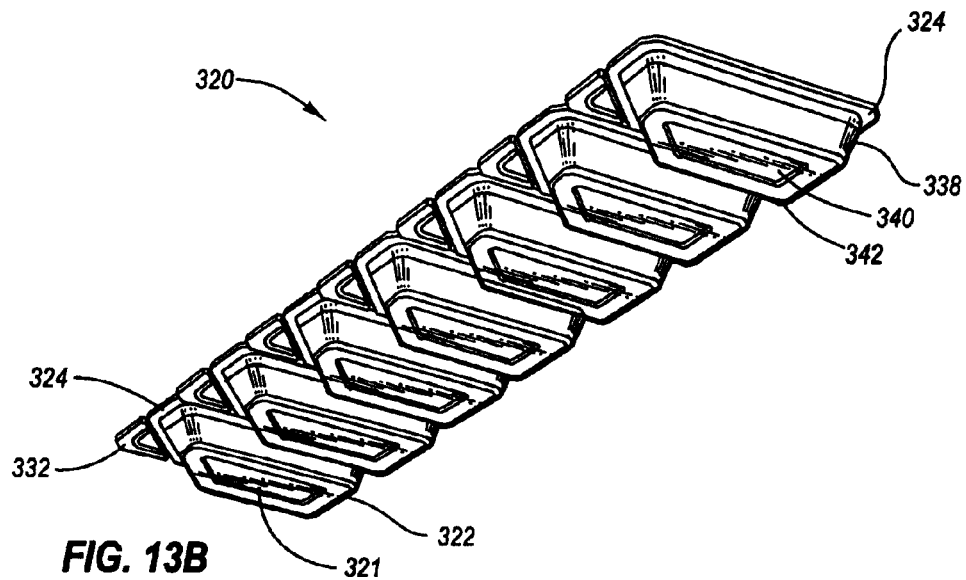

Referring to FIG. 13A and FIG. 13B there is shown a top view and a bottom view of a plurality of illustrative sealed multiple prescription containers 320. In FIG. 13A and FIG. 13B, both views reflect that one of the containers 321 comprises a tapered body container 322 with a cavity for holding a plurality of tablets. The tapered body container 322 allows a plurality of individual containers to be stacked for storage. Each container 320 has a flanged top surface 324 configured to be sealed with a lid 326. In certain embodiments, the tablet assembly may require individual containers that vary in depth depending on the amount of tablets needed to be dispensed at a specific time. While the depth of the individual containers may vary, the flanged top surface and collar remain constant for processing of different sized individual containers and for commonality with the assembly sleeve.

In one embodiment, the multiple prescription container assembly comprises a plurality of individual containers. In one illustrative embodiment, container 321 is coupled to container 328 with lid 326. The lid 326 seals one or more containers. The sequential connection enables a linear configuration for the individual containers. However, it should be noted that the quantity of containers in a multiple prescription assembly may vary as well as the interconnection configuration of the containers, e.g. a circular, an elliptical, polyhedral, etc.

In another embodiment, the plurality of multiple prescription containers are made from a single piece of moldable material having a plurality of indentations wherein each indentation is configured to form one container 321 in the set of containers 334. At least one of the containers is configured to receive a first tablet associated with a first medication, and a second tablet associated with a second medication that is different from the first medication. The set of containers 334 are connected to one another by frangible connections 336 or perforations positioned within the flanged edge 324 that are proximate to the adjacent container. The frangible connection 336, which is between containers, allows the containers to "break-away" from the set of containers 334 in a sequential manner. Once the lids are attached and/or sealed to the top flanged surface 324, this sequential connection enables a linear configuration as described above.

Each container may also comprise a collar 338 below the flanged edge 324 that allows the containers to be stored in a stackable configuration. Stacking of the containers can also be performed with the collar 338. Each container may also comprise a bottom surface 340 with at least one ridge 342. The ridge is useful in minimizing tablet-to-tablet collisions and avoiding medication sloughing off of a tablet due to collisions with other tablets. By limiting excessive movement of the tablets in each of the containers, the ridge or ridges on the bottom of the container(s) help preserve the integrity of the tablets within. The ridge may protrude outward from the bottom surface of the containers as shown in FIG. 13B, or in other embodiments, may be formed by an indentation of the bottom surface. The ridge(s) may be configured as a square, rectangle, circle, and a plurality of parallel lines as well as other geometric shapes.

The illustrative set of containers 334 comprises seven adjacent containers configured for sequential dispensing of the contents of each container. Sequential dispensing refers to individual containers being "dispensed one at a time," which is different from being "cherry picked" from a grid of individual containers. The number of containers in a set of integrated containers may vary due to the prescription prescribed for the user. While the illustrative embodiment describes seven containers, a set of containers may comprise at least two containers to about 20 containers, and more preferably about 5 to about 14 containers. It is expected that most of the containers will be of similar size for ease of filling the containers, but in certain embodiments varying container sizes may be needed. The set of containers 334 may be opaque but in preferred embodiments, the moldable material comprises enough clarity for the user to visualize the contents of the containers.

The illustrative lid 326 of container 321 comprises a printing surface where unique prescription-specific information is displayed for each container. The information displayed on the printing surface may include, but is not limited to, the patient's name, the date and the day of the week the contained mixed dosage medications (tablets) are to be taken, as well as the time of day that the tablets are to be taken. The markings on the containers inform the patient and/or caregiver the time in which the contents of the container are to be taken in the proper sequence. In general, the lid stock comes from a roll and the appropriate amount of lidstock is released from the roll to accommodate the designated number of containers to be sealed. For a thermoformed container, using polypropylene for the material for the lid stock, an unsealed area of lid film is generally used to help in the peeling of the lid. The breakaway tab 332 on the illustrative container 321 gives the user something to hold onto and is a useful feature to a container that is manufactured by injection molding with plastics like polyethylene or styrene.

Figure 14:
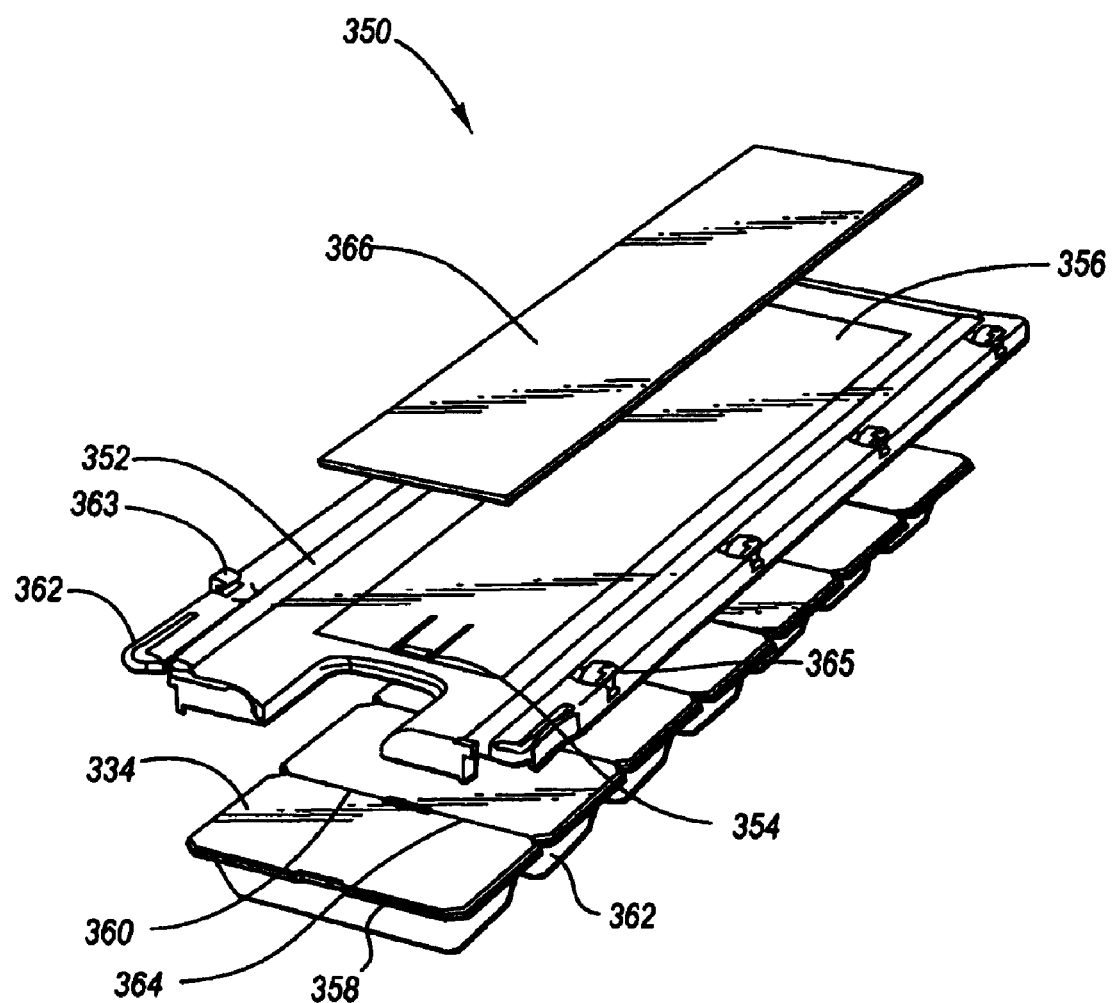
FIG. 14 is an exploded isometric view of the sleeve for the multiple prescription container assembly before it is slidably coupled to the sealed containers.

Referring to FIG. 14 there is shown an exploded isometric view of the multiple prescription container assembly 350 before slidably coupling the set of sealed containers 334 to the dispensing sleeve 352. The exploded view also shows a top tab 354 on the top surface 356 of the sleeve which holds the end container 358 by catching the rectangular void made by one of the indentations 360. When the user pushes down the sleeve tabs 362, the set of sealed containers are released and the top tab 354 is disengaged from the containers. The end container 358 can be slid out of the dispensing sleeve 352 if there are no other child protective features, and the top tab latches on to the next indentation (not shown). The user then can break the frangible connection 364 and remove the container. This two-step process of holding tabs 362 and pulling on the end of the sealed containers is a "child safety" feature. It shall be appreciated by those skilled in the art that certain embodiments can be made to conform to a more senior-friendly solution that is described in further detail below.

Additionally, there is shown a notch 363 that is configured to be fit into an illustrative cavity that is a square-shaped perimeter 365 and receives a notch similar to notch 363. The notch 363 permits two dispensing sleeves to "snap" together. The square shaped perimeter 365 is located on near the edge of the dispensing sleeve 352 and has a square cut and a lip.

Printed material 366 may be attached to the top surface 356 of the dispensing sleeve 352. Additional information about the prescription or other patient data can also be placed on the dispensing sleeve 352. The dispensing sleeve 352 may also comprise a surface for printable indicia, and the printable indicia may include patient data as well as prescription information.

Figure 15:
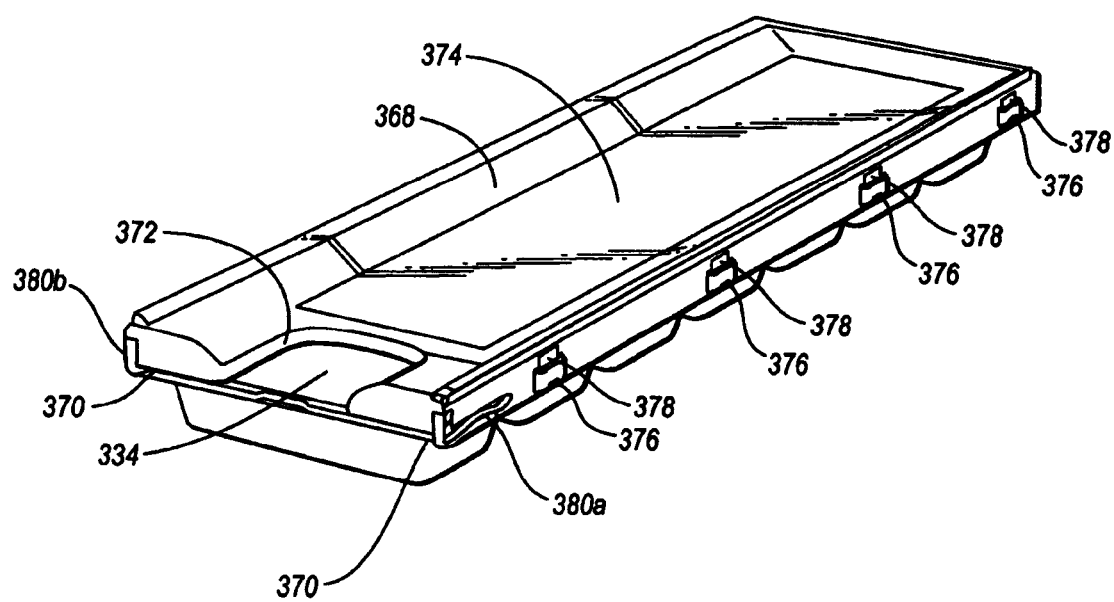
FIG. 15 is an isometric view of the sealed containers slidably coupled to the sleeve for sequential dispensing.

Referring to FIG. 15 there is shown an isometric view of the set of sealed containers slidably coupled to another sleeve for sequential dispensing. In this illustrative embodiment, the sealed multiple prescription containers are operatively coupled to the dispensing sleeve 368. The dispensing sleeve 368 is similar to the dispensing sleeve 352 in that both sleeves comprise grooves or slits 370 configured to allow the flanged top surface 324 (see FIG. 13) of each container to slide into the respective dispensing sleeve. Additionally, both sleeves comprise a thumb groove 372, which is configured for a human thumb or finger, allowing a patient or caregiver easy access to the sealed prescription container. The thumb groove 372 also acts as a display window to allow the patient to view the printed markings on each lid. The dispensing sleeve 368 also contains a printable area 374 large enough to accommodate a detailed label with information about each tablet in each of the containers. The dispensing sleeve 368 and 352 may be produced as one piece and is configured to lock onto another sleeve with a "snap and lock" means comprising at least one protruding section 376 that defines a cavity 378 of the dispensing sleeve. The protruding section is configured to receive a notch (not shown) that can interface directly with the protruding section 376. The dispensing sleeve may be injection molded or manufactured from plastics such as polypropylene and ABS.

Additionally, the particular sleeve 368 further comprises integral, mold-in release tabs 380a and 380b configured to allow the sealed containers to slide out of the dispensing sleeve 368 when pressure is applied to release tabs 380a and 380b. The container 350 is then removed by breaking the perforation mark between the containers. The release tabs are configured to "catch" the next container 350 so that one container is released at a time, thereby providing child resistance.

Figure 16:
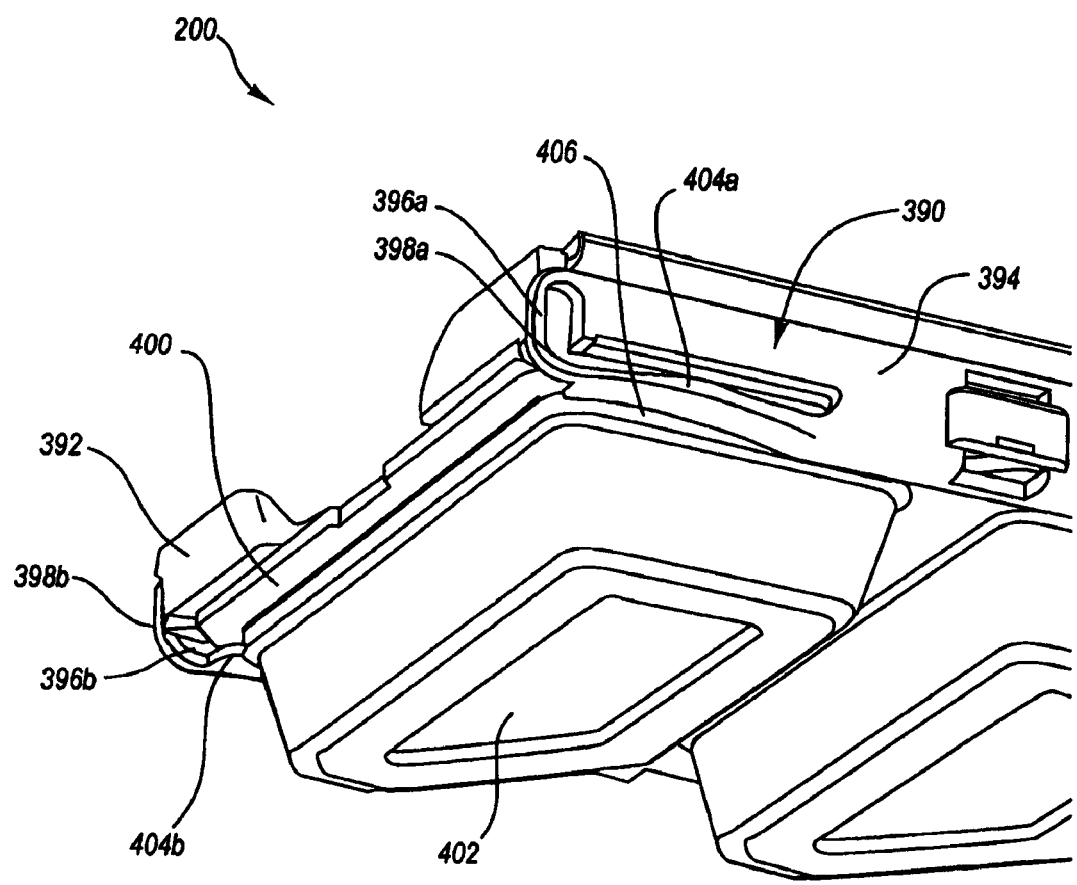
FIG. 16 is an exploded view of an illustrative child protective feature for a multiple prescription container assembly.

Referring to FIG. 16 there is shown an exploded view of an illustrative child protective feature 390 for a multiple prescription container assembly. The first end 392 of the dispensing sleeve 394 comprises release tabs 396a and 396b configured on the sides of the sleeve. The release tabs 396a and 396b each comprise a molded loop 398a and 398b configured to hold the top flanged surface 400 of the end container 402 in the dispensing sleeve 394. The molded loops 398a and 398b have concave sections 404a and 404b which contact the bottom side of the top flanged surface 406. When the end container 402 is to be taken out of the dispensing sleeve, the downward pressure of the user's thumb on the lid of container 402 in the thumb well pushes the concave section 404a and 404b downward, releasing the top flanged surface from the release tabs 396a and 396b, allowing container 402 to exit the dispensing sleeve 394. Other embodiments of the release tab(s) will readily suggest themselves to those of ordinary skill in the art.

Figure 17:
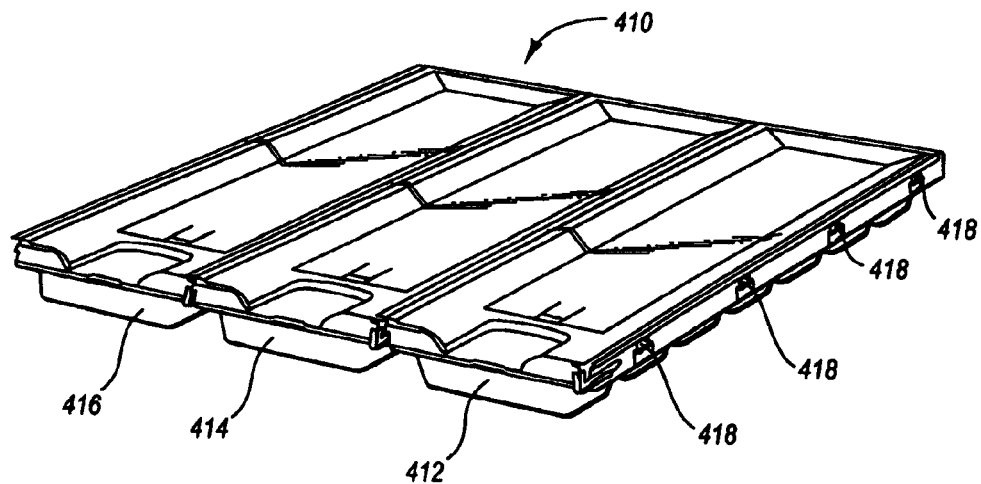
FIG. 17 is an illustrative embodiment of a plurality of dispensing sleeves that are connected to one another.

Referring to FIG. 17 there is shown an illustrative embodiment of a plurality of dispensing sleeves 410 that are configured to interface with at least one other sleeve having a plurality of sealed containers. The dispensing sleeves 410 are similar to dispensing sleeve 368 described above. The first dispensing sleeve 412 is fixedly coupled to dispensing sleeve 414, which in turn is fixedly coupled to dispensing sleeve 416. Each sleeve comprises a plurality of knobs or hooks on a first side of each sleeve 362 and a plurality of corresponding shaped grooves or knob receptacles 418 on the second side of each sleeve, which enables the sleeves to interlock. In this embodiment, each dispensing sleeves 412, 414, and 416 are grouped together for daily usage on a per week basis for a patient that needs to take medications three times per day.

Figure 18:
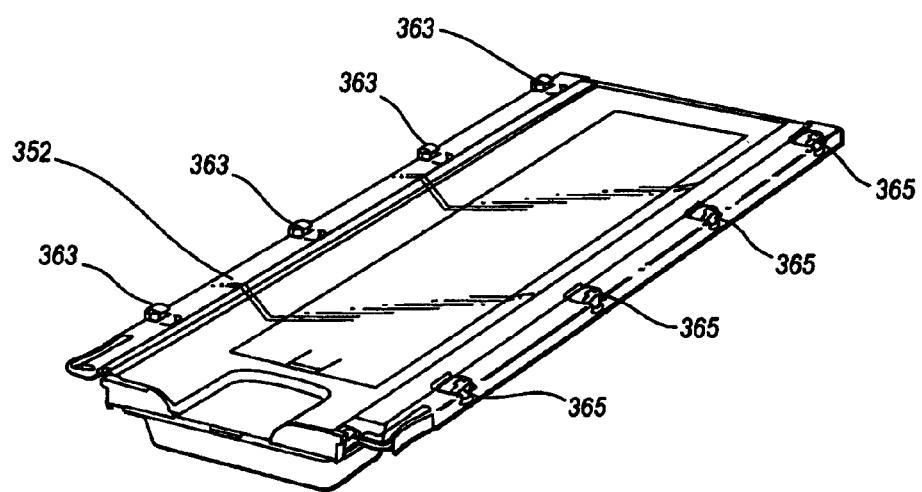
FIG. 18 shows illustrative notches of interlocking elements for an illustrative dispensing sleeve.

Referring to FIG. 18 there is shown illustrative notches of interlocking elements for the illustrative dispensing sleeve 352 shown in FIG. 14. The illustrative notches 363 are configured to be fit into a plurality of square-shaped perimeters 365 that define a cavity. The notches 363 and square shaped perimeters permit two dispensing sleeves 352 to fit together. The square shaped perimeters 365 define a cavity that is located adjacent to the edge of the dispensing sleeve 352. Additionally a small lip is shown that permits the notch to be locked into place.

Figure 19:
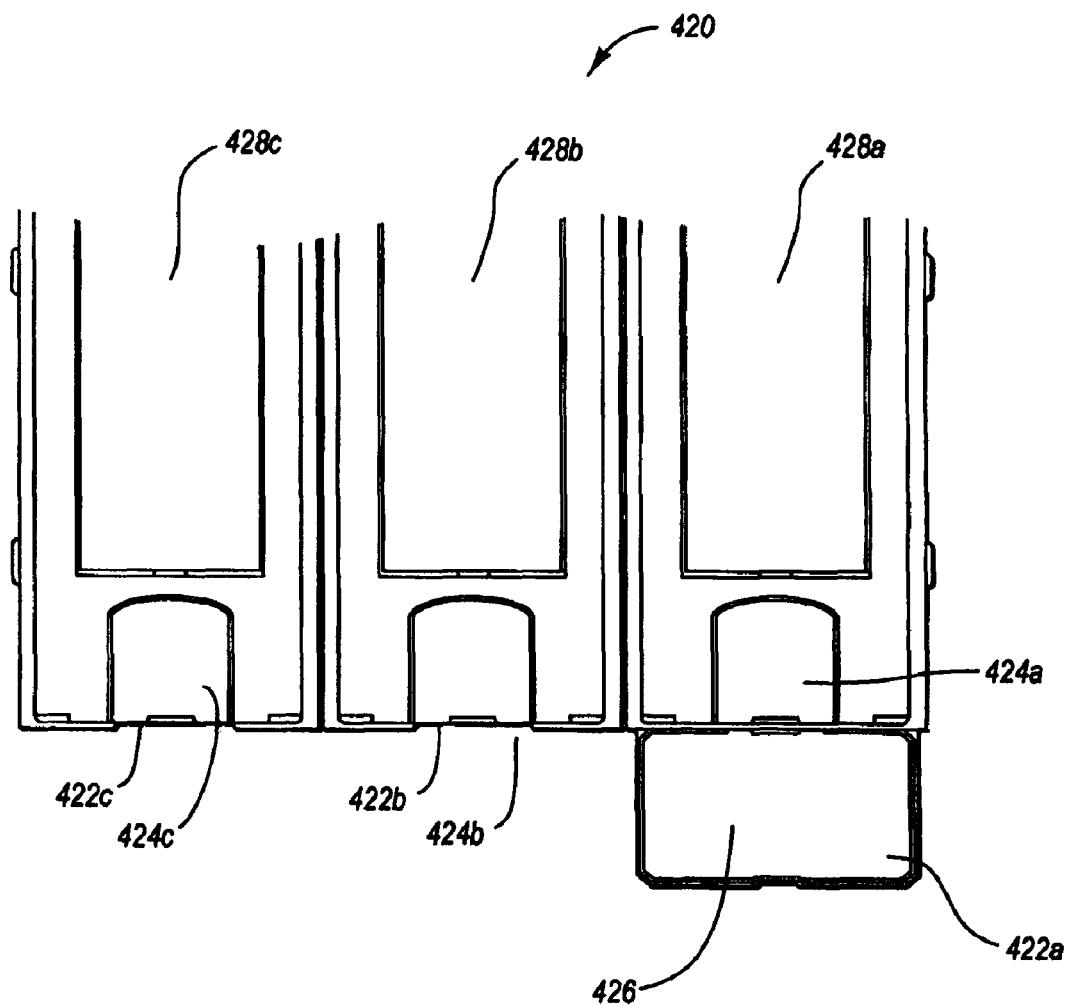
FIG. 19 is an illustrative top view of multiple sleeves coupled to one another and depicting the sequential dispensing of a container.

FIG. 19 is an illustrative top view of multiple sleeves coupled to one another and depicting the sequential dispensing of a container. In this illustrative example, the multiple prescription container assembly is for patients that must take multiple medications more than once a day. The multiple prescription container assembly 420 comprises a plurality of thermoformed (or molded) sets of sealed container 422a, 422b, and 422c that are heat sealed with a laminated lid 424a, 424b, and 424c, respectively. Each container within the set of containers 422a, 422b, and 422c contains the required medications that have been prescribed for a particular time. The containers are separated by perforations as described above. In the illustrative embodiment, each container contains printed markings 426 that identify the medications contained therein, and may also indicate the patient's name, and, most importantly for the purposes of this embodiment, the day and the time of day that the medications are to be taken.

In the illustrative embodiment of FIG. 19, each container is dedicated solely to a particular time of day. In the illustrative example, the set of containers 422a are taken in the morning, the set of containers 422b are taken at approximately noon, and the set of containers 422c are taken in the evening. Thus, it is possible to have a plurality of containers for each day of the week so that each container has the proper dosage that is to be taken at a particular time of day. In this illustrative embodiment, the patient is supplied with a complete set of containers for a particular week for a specific time of day.

Each individual container within each set of containers is to be taken at the correct, prescheduled time each day as marked 426 on each container. The multiple prescription container assembly 420 may be provided to the patient or caregiver as three separate sets of containers enclosed in three separate dispensing sleeves. The patient or caregiver can interlock the three separate dispensing sleeves 428a, 428b, and 428c.

Referring to FIG. 20A there is shown a top view of a dispensing sleeve housing a plurality of rounded multiple prescription containers. The illustrative rounded multiple prescription container 430 comprises a plurality of containers 432 that are adjacent to one another. Each container is wedge shaped so that the triangular surface area at the top of each container is greater than the triangular well at the bottom of each container. The illustrative container 432 is surrounded by a flanged edge 434. The dispensing sleeve 436 surrounds the rounded multiple prescription container 430. A release tab 438 on the sleeve 436 permits the rounded multiple prescription container 430 to be rotated within the sleeve 436. The axis of rotation is defined by the well 440 at the center of the plurality of containers. A plurality of ridges 442a, 442b, 442c, and 442d on the sleeve 436 hold cover, lidstock, or any other labels in place.

Referring to FIG. 20B there is shown a bottom view of the dispensing sleeve housing the rounded containers described in FIG. 20A. The bottom view shows the rounded multiple prescription container 430 and the illustrative container 432 with the flanged ends 434 that interface with the sleeve 436. The flanged ends 434 are slidably coupled to the sleeve 436 via a plurality of lips such as lip 444. The bottom view also shows the release tab 438 that permits the rounded containers to rotate around the sleeve.

Additionally, a rim 445 is shown that is the approximate depth of the container. The rim 445 receives printed information about the particular patient taking the prescribed medication. The rim 445 also permits the stacking of a plurality of rounded multiple prescription assemblies.

Figure 21B:
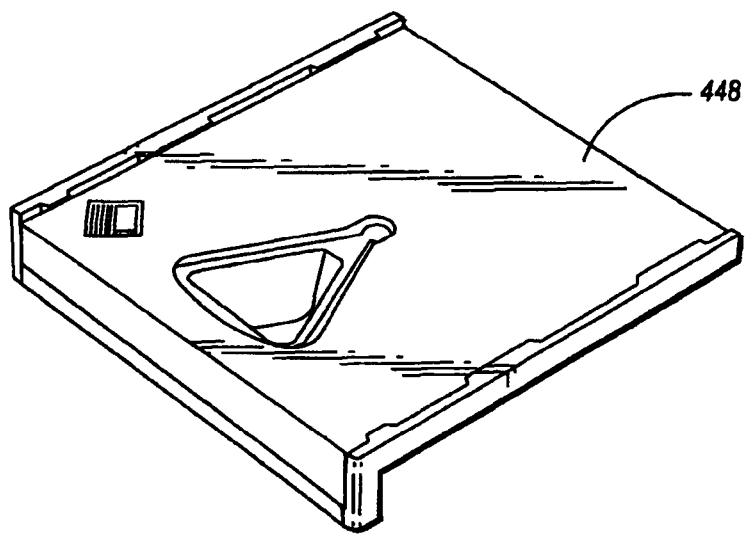

Referring to FIG. 21A there is shown the dispensing sleeve housing the rounded containers having a first lid and a cover. The first lid 446 is visible and is associated with a particular multiple prescription container and is adhesively coupled to the flanged edges of the container. The cover 448 shields the lids and containers within each sleeve. The combination of elements shown in FIG. 21A illustrates a rounded multiple prescription assembly 450. In FIG. 21B, the first lid 446 is removed, permitting access to the different medications within the container. There may be a variety of printed information on the lid 446 and/or the cover 448.

Referring to FIG. 22, there is shown an alternative sleeve 452 that does not comprise a rim 445. The sleeve 452 is configured to receive the rounded multiple prescription container 430, and the combination results in an alternative embodiment of the rounded multiple prescription container assembly 454.

Both of the multiple prescription container assemblies 450 and 454 are configured for sequential dispensing. While the illustrative embodiment describes seven containers, a set of containers may comprise at least two containers to about 20 containers, and more preferably about 5 to about 14 containers. It is expected that most of the containers will be of similar size for ease of filling the containers. Additionally, the illustrative moldable material comprises enough clarity for the user to visualize the contents of the containers.

The information displayed on the lid and cover may include the patient's name, the date and the day of the week the contained mixed dosage medications (tablets) are to be taken, as well as the time of day that the tablets are to be taken. The markings on the containers inform the patient and/or caregiver the time in which the contents of the container are to be taken in the proper sequence. In general, the lidstock comes from a roll and the appropriate amount of lidstock is released from the roll to accommodate the designated number of containers to be sealed. For a thermoformed container, using polypropylene for the material for the lid tock, an unsealed area of lid film is generally used to help in the peeling of the lid.

Referring to FIGS. 23A and 23B, there are shown two separate perspective views of a plurality of stacked rounded multiple prescription container assemblies. The stacked rounded multiple prescription assemblies 456 are composed of a plurality of rounded multiple prescription container assemblies 450. Each of the multiple prescription container assemblies 450 are stacked on top of one another with the rim 445, which permits the stacking of rounded, multiple prescription container assemblies.

Referring to FIG. 24A there is shown a perspective view of a circular multiple prescription container assembly. In this illustrative embodiment, the circular multiple prescription container assembly 460 comprises a set of multiple prescription containers 462 having flanged edges similar to the flanged ends 434 (described in FIG. 20A), a lid 464, and a cap 466. The lid 464 seals the multiple prescription containers 462. The cap 466 fits over the flanged ends (not shown) and has a triangular opening 468 cut into the cap 466. The cap 466 is configured to snap fit with the sealed multiple prescription containers. The triangular opening 468 permits the patient and/or caregiver to view writing on the lid 464 and to have access to the lid 464. Referring to FIG. 24B, there is shown an illustrative embodiment in which the lid 470 has printed information that identifies the patient, the date, and the time that the prescribed medications are to be taken.

Additionally, the illustrative lid 464 is cut to permit a patient to remove the lid by placing a finger underneath a cut 472. A ridge 474 permits the lid 464 to be more easily removed from the container. A more detailed view of a patient or caregiver removing the lid 464 is provided in FIG. 25. Once the contents of a particular container have been removed, the cap 466 is rotated, and provides access to the next sealed container.

Referring to FIG. 26 there is shown a flowchart of an illustrative method for dispensing tablets which utilizes a secondary package or sleeve for receiving a multiple prescription container 500. This embodiment of the method for dispensing tablets comprises providing a set of integrated containers 502, the containers adjacent to one another and filling each container with at least one tablet previously specified for each container. The method also comprises the set of integrated containers having a flanged edge and at least one frangible connection (e.g. perforated line) configured within the flanged edge between each of the plurality of containers 504. The method may also comprise providing a lidstock with a plurality of lids that may be adjacent to one another in a linear arrangement 506. The configuration of the lids is not limited to a linear arrangement and may be configured in any manner as to be capable of sealing the set of integrated containers. The method further comprises providing a frangible connection (e.g. perforated line) between each of the plurality of lids 508. The frangible connection may be a thinned region of plastic that is easily breakable, perforations in the film and the like.

The method comprises sealing the plurality of containers of the set of integrated containers with the corresponding plurality of lids 510 of the lidstock. The quantity of the containers in the tablet assembly is variable, depending on the prescription of the patient. The number of lids will correspond to the number of containers utilized in the tablet assembly. A printable surface is provided on each of the plurality of lids 512 in which specific printing indicia or information is placed 514 relating to the administration of the tablets held in the container sealed by the corresponding lid.

This method may also comprise providing a sleeve or secondary package for receiving the set of sealed containers 516 and placing the set of sealed containers into the sleeve 518. The patient completes the process of dispensing the tablets by expelling or manually moving one of the plurality of sealed containers out of the sleeve at the time printed on the corresponding lid 520. Once the container has been slid out from the secondary package, the container is removed from the set of containers as well as the secondary package and/or sleeve by tearing the frangible connection between the expelled container and the adjacent container remaining in the sleeve 522. The patient can then gain access to the tablets in the expelled container by removing the lid from the container 524. In some alternative embodiments, the method comprises providing extended tabs on the lids, break-away tabs and/or providing chamfered edges on the containers to make removing the lid off of the container more convenient.

In yet another embodiment, the method further comprises providing a child safety release tab on a secondary sleeve as seen on the tablet assembly embodiment shown above, to prevent unwanted tampering of the tablets in the containers by children. In this embodiment, at the proper time for dispensing the tablets from a container, the patient holds the dispenser and manually actuates the release tabs while simultaneously manually sliding the strip of containers in a direction "out of the dispenser." When the perforations or frangible connection between the first two containers in the strip reach the outer edge of the dispenser the release tab resets, thus locking the strip from further sliding motion. The patient then tears off, at the perforations, the protruding container that contains the correct medications for the stated time, pulls up on the extended corner of the lid, and opens the container by peeling back the lid, exposing the medications. The dispenser then is left with the correct printed markings showing in the thumb groove display window, ready for the next dosage to be taken.

Other embodiments of the methods of dispensing tablets comprise, providing a "senior friendly" tablet assembly instead of an assembly with a child safety tab for the convenience of patients with limited dexterity.

Referring to FIG. 27 there is shown a flowchart of the production facility processes 600 used by an illustrative production facility to fill a prescription order. After receiving the prescription order in one of the illustrative system and/or methods described above, the order processing system 602 begins controlling the filling of the prescription order. By way of example and not of limitation, the ordering processing system 602 interfaces with an online server, production server, or both, and receives data that relates to the type of medication or tablet, and the type of multiple prescription container assembly that needs to be filled with the appropriate medications and/or tablets. Those with ordinary skill in the art of manufacturing processes and robotic processes shall appreciate that the systems or methods for controlling production can be performed using a centralized control system or a distributed control system. For purposes of this patent, those with ordinary skill in the art shall appreciate that there will even be instances where a combination of centralized and distributed control are optimal, and depend on design requirements and expectations.

The order processing system 602 is in communication with a tablet management system 608. The tablet management system 608 controls the tablets that fill the pill refill modules, which in turn fill up the appropriate multiple prescription containers. The tablet management system 608 also communicates when a refill module is not properly being filled.

The order processing system 602 also communicates with a container selection process 604. The container selection process 604 may receive an order for a particular container assembly from the user placing the order, e.g. pharmacist, caregiver, patient, etc. Alternatively, the container selection process 604 may simply receive a multiple prescription order, and may have to select the appropriate container for filling the order, e.g. less than 5 tablets require a small container, 6-10 tablets require a mid-size container, and 10-20 tablets require a large container.

After the container selection process 604, there is a container inspection process 606 during which inspection of the appropriate container is performed, to ensure that the appropriate container or substitute container has been selected. Additionally, the inspection process 606 may include identifying whether the container is broken or has some obstruction that may cause some difficulty to downstream systems and/or processes.

After the container inspection 606, the container filling process 610 is initiated. In an illustrative example, the container filling process 610 occurs by placing the selected container on a pallet or tote and moving the pallet or tote on a conveyer, which moves the pallet to the appropriate filling location so that the appropriate tablets may fill the container.

After filling the appropriate container with a plurality of medications and/or tablets, an inspection of the filled containers is performed at block 612. The inspection may be conducted by using X-ray detection, near infrared detection, robotic detection at visual wavelengths, or any other such technique that looks at color, shape, density, or other such parameter to determine if the appropriate container has been filled with the correct prescription. Thus, in certain instances, a visual inspection by a pharmacist may be satisfactory.

After inspection, the method proceeds to the lid assembly process 614 during which the lid is applied to the multiple prescription container. The sleeve is then applied at the sleeve assembly process in block 616. Alternatively, a cap may be placed on the sealed multiple prescription container, as described above. For purposes of this patent, the term "sleeved container" encompasses a multiple prescription container having a cap, unless otherwise indicated.

At block 618, the inspection of the sleeved sealed containers is conducted. This inspection at block 618 is performed after the multiple prescription container has been sealed. Note, the inspection at block 612 was conducted before sealing. The need for the second inspection described in block 618 is in case a tablet or medication fell out of the container or was mislabeled. Additionally, one of the tablets or medications may also have been broken or otherwise compromised.

As stated above, the inspection may be conducted using a variety of different instruments including, but not limited to, robotic inspections at a visual wavelength, near IR, X-ray and any other detection means that can identify the type of tablets or medication in each container.

The method then proceeds to block 620 where the sleeved sealed container(s) are combined with printed materials in the tote. The printed materials may include labels as described in FIG. 5-7 above. Additional materials may also be provided such as printed materials from pharmaceutical companies, medical providers, pharmacists, and other such entities. The printed materials are controlled by the tote assembly system 622. The printed materials may be generated at the production facility or may be shipped to the production facility or any combination thereof.

After combining the printed materials and the sleeved sealed multiple prescription containers, the combination is shipped to a pharmacy or customer as described by block 624. As stated above, the customer may be a patient, a caregiver, a medical health professional, or any other such person Referring to FIG. 28, there is shown an illustrative production facility 628 that would occupy a warehouse. A plurality of container 630 are fed in a container feeding section by an operator 632 that places the containers on a pallet or tote that are carried by a conveyor belt 634 around the facility. The operator 632 is charged with container selection based on the information provided by the order processing system. Additionally, the operator 632 is charged with performing a visual inspection of the containers that are placed on the pallet or tote.

The powered conveyor then transports the tote having the empty containers to filler cells that have a particular medication or tablet. As the empty container passes under each filler cell 635, the tablet management system determines whether a tablet is to be dispensed. The container filling process requires a variety of different filling cells that have to be refilled by illustrative operators 636 and 638. The conveyor belts and filler cells are grouped into units for easier operation and maintenance. In the illustrative embodiment, the powered conveyers can travel to the appropriate filler cell in an efficient manner that permits a particular pallet to bypass traveling along the perimeter of the conveyor assembly. For example, a particular pallet may bypass traveling along the length of a conveyor via a bypass 640 or 642.

The filled containers are then inspected to determine if the container has been properly filled. An operator 644 mans the inspection equipment. If order adjustments are needed, another operator 646 is charged with resolving any problems with one or more orders. If the operator 644 determines that the prescription has been properly filled, then the appropriate lid is placed on the containers. A lidstock sealer 648 seals the lid on the multiple prescription container. The sleeve is then selected at the sleeve assembly 650 and then applied. The operator 652 inspects the sleeve. Alternatively, the operator 652 may be charged with combining the sleeved and sealed prescription container. A separate tote filling system 654 generates the printed materials that are combined with the pallet or tote having the sleeved and sealed multiple prescription containers. The conveyor 656 then transports the filled prescription order to a predetermined location so that the filled prescription order may be shipped to the pharmacy or customer.

Referring to FIG. 29 there is shown a perspective view of an illustrative tabletop system that can be used to have an illustrative pharmacist to fill the multiple prescription order. Although the warehouse size production facility is described above in FIG. 28, the tabletop system is much smaller and can also be used to fill a multiple prescription order. The illustrative table top system 660 receives a prescription order at station 662. The appropriate containers 664 are selected and placed on a conveyor (not shown) that are fed under fill cells 666. At workstation 668 the multiple prescription order is inspected by the illustrative pharmacist. A lid is generated at station 670 and sealed at station 672. The sleeve located at sleeve dispenser 674 is then applied. The sealed sleeve assembly is then inspected by the pharmacist. Printed materials are generated by printer 676, and the printed materials are combined with the sealed and sleeved multiple prescription container. The filled multiple prescription may then be picked up at a "pick-up" window 678. A pharmacist at station can then explain to the customer about the multiple prescription packaging.

Referring to FIG. 30 there is shown a block diagram of an illustrative order processing system 602. The order processing system 602 is configured to control the filling of the prescription order. The order processing system comprises a block 690 in which a multiple prescription order is received. The multiple prescription order may be received electronically or at a pharmacist's window. The system 602 then proceeds to check an inventory management system 692 and determines if the appropriate medication or tablets are available. At decision diamond 694, a decision to order additional inventory is made if the inventory of tablets or medication are running low. If inventories are running low, then at block 696 an order is placed for additional tablet inventory. However, if there is a satisfactory inventory, block 698 communicates tablet type, size, quantity, frequency, packaging, and time for taking the prescribed medications in the container selection process 604 and the pill management system 608.

The order processing system 602 also accommodates receiving the tablet received in block 700, after having placed the order for additional inventory in block 696. After receiving the order tablets, the inventory management system is updated as indicated in block 702. The updated inventory is then communicated to the pill management system 608. The order processing system 602 is intended to make it more efficient for a production facility and/or pharmacist to manage the tablet or medication inventory stored at the local facility. By creating a system and method for automated ordering, the order processing system can provide a more efficient means for controlling inventory and thereby more efficiently control the filling of multiple prescription orders in multiple prescription containers.

Referring to FIG. 31 there is shown a flowchart of an illustrative container selection process 604. The container selection process 604 may receive an order for a particular container assembly from the user placing the order, e.g. pharmacist, caregiver, patient, etc. Alternatively, the container selection process 604 may simply receive a multiple prescription order, and may have to select the appropriate container for filling the order, e.g. less than 5 tablets require a small container, 6-10 tablets require a mid-size container, and 10-20 tablets require a large container. For either embodiment, the container selection process 604 is initiated by receiving the appropriate tablet and/or container information. For example in block 704, tablet data and/or container selection data is received that may comprise type of tablet or medication, size of the tablet or medication and the frequency with which the tablet or medication needs to be consumed.

At block 706, the method may determine the type of container to use based on the types of medications, size, and frequency. The determination of the type of container may be performed without receiving a user's request for a particular multiple prescription container assembly as described above. The determination of container availability is then made at decision diamond 708. If a particular container is not available, the method may return to block 706 to select an alternative container. Issues associated with container availability are reported to the inventory management system 702. If the containers are available, the method proceeds to block 710 where the containers are de-nested and then placed on the appropriate pallet, at block 712. The method then proceeds to container inspection at block 706.

Referring to FIG. 32, there is shown an illustrative block diagram of an illustrative tablet management system 608. The illustrative tablet management system 608 controls the tablets that fill the pill refill modules (described above). The tablet management system 608 also communicates when a refill module is not properly being filled. Bulk tablets are received at block 720 and then are fed into an illustrative hopper 722. The tablets are then separated by a separator 724 and are then inspected 726 to determine if they have been placed in the appropriate refill module.

A tablet refill control system 728 manages the tablet being distributed to the appropriate refill module 730. Additionally, the tablet refill control system receives tablet information 732, and this tablet information is stored on the tablet refill control system 728. The additional tablet inventory and is then communicated to the inventory management system 702.

Referring to FIG. 33 there is shown an illustrative refill module 730. The illustrative refill module includes a hopper 734, separator 736, and sensor 738 that counts the tablets. The tablet refill control system 728 communicates with the illustrative refill module 730. A plurality of feeding tubes 740 distributes one or more tablets to the illustrative containers 742. Broken tablets are collected in bottle 744 after being inspected by sensor 738.

Referring to FIG. 34 there is shown a flowchart of an illustrative multiple prescription container filling process 610. Recall, the container filling process 610 occurs by placing the selected container on a pallet or tote and moving the pallet or tote on a conveyer that moves the tote or pallet to the appropriate filling location so that the appropriate tablets may fill the container. In the illustrative production facility described in FIG. 28 or the illustrative bench system in FIG. 29, an operational conveyor system is used to transport the containers. Thus, in the illustrative examples an operation conveyer system 750 is required. However, those skilled in the art shall appreciate that a conveyer system may not be required and may instead rely on being gravity fed and placed into a particular container configured to hold a plurality of medications or tablets.

The illustrative conveyer system receives a container pallet or tote at block 752. The containers then stop at the appropriate refill module and are filled with tablets as described in block 754. Additionally, each refill module may comprise a sensor 738 that counts the number of tablets that are distributed by the refill module, and this count may be communicated to the tablet refill control system 728. A container tracking system 756 tracks the location of each container so that the appropriate medications or tablets are filled by the appropriate filling modules. By way of example and not of limitation, the container tracking system 756 and the refill module are communicatively coupled to the tablet refill control system 728. After the containers are filled by the plurality of refill modules, the illustrative unsealed containers are inspected at block 714.

Referring to FIG. 35 there is shown an exploded perspective view of the illustrative tabletop system 660 that comprises order processing, pill management, container selection, container inspection, container filling, lid generation and lid placement. As described above, the illustrative table top system 660 receives a prescription order at station 662. The appropriate containers 664 are selected. By way of example and not of limitation, there are three different size containers, e.g. small, medium, and large. The appropriate containers are selected by the pharmacist and are then placed on a conveyor 665, which feeds these multiple prescription containers to refill cells 666. The refill cells 666 are configured to deposit the appropriate tablets and/or medications into the containers. At workstation 668 the filled multiple prescription order are visually inspected by the pharmacist. Alternatively, there may be other means of inspecting the filled, yet unsealed, multiple prescription containers such as near infrared, X-ray, or such means for inspection. A lid is then generated at station 670.

Referring to FIG. 36 there is shown a flowchart with a more detailed flow of the inspection of filled multiple prescription containers that have not been sealed. After filling the appropriate container with a plurality of medications and/or tablets, an inspection of the filled containers is performed at block 612. The inspection may be conducted by simply providing an image to the pharmacist so that the pharmacist can see if the appropriate tablet or medication is in each container, as represented by block 760. Additionally, precision weighing 762 may be used to make sure that the appropriate tablets or medications are deposited in the appropriate multiple prescription container. The inspection may also be conducted by using X-ray detection 764 or some other form of detecting such as near infrared detection, robotic detection at visual wavelengths, or any other such technique that looks at color, shape, density, or other such parameter to determine if the appropriate container has been filled with the correct prescription. If a determination is made that the multiple prescription container has not been properly filled, then order adjustment 766 may be performed. After inspection, the process continues to lid assembly processing.

Referring to FIG. 37 there is shown a flowchart describing an illustrative lid assembly process 614. After inspection, the method proceeds to the lid assembly process 614 during which the lid is applied to the multiple prescription container. The lid assembly process 614 comprises receiving blank lidstock 770, and placing the lidstock 772 in a position so that lidstock printing 774 can take place. To perform the printing on the lidstock, a printing ink, toner, or ribbon is needed.

In the illustrative production facility 628, a pallet is used to transport the multiple prescription container to the appropriate lid assembly section, as described by block 778. In another embodiment 660, a pallet is not needed and the container simply travels along the conveyer. In yet another embodiment, a conveyer is not needed. However, regardless of the system and method used to transfer the filled multiple prescription container, a label needs to be applied. In this illustrative embodiment, the appropriate label is generated as described above and placed on the filled multiple prescription container as represented by block 780. The method then proceeds to block 782 where the lidstock is heat sealed to the filled multiple prescription container. The sleeve is then applied at the sleeve assembly process 616.

Referring to FIG. 38 there is shown a flowchart of an illustrative sleeve assembly process 616 where the sleeve is applied to the sealed multiple prescription container. By way of example and not of limitation, the sealed multiple prescription container is communicated using a pallet, as represented by block 790. The sleeve is then combined with the sealed multiple prescription container at block 792.

The illustrative sleeve is generated by receiving a blank sleeve 794 and placing the sleeve 796 in the appropriate position so that a printed label 798 can be placed on the sleeve. The printed label 798 may be generated locally with printing ink, toner, or a ribbon 802. The complete sleeve assembly 804 is then ready to be coupled to the sealed multiple prescription container. As described above, a cap may also be placed on the sealed multiple prescription container, instead of a sleeve.

Figure 39:
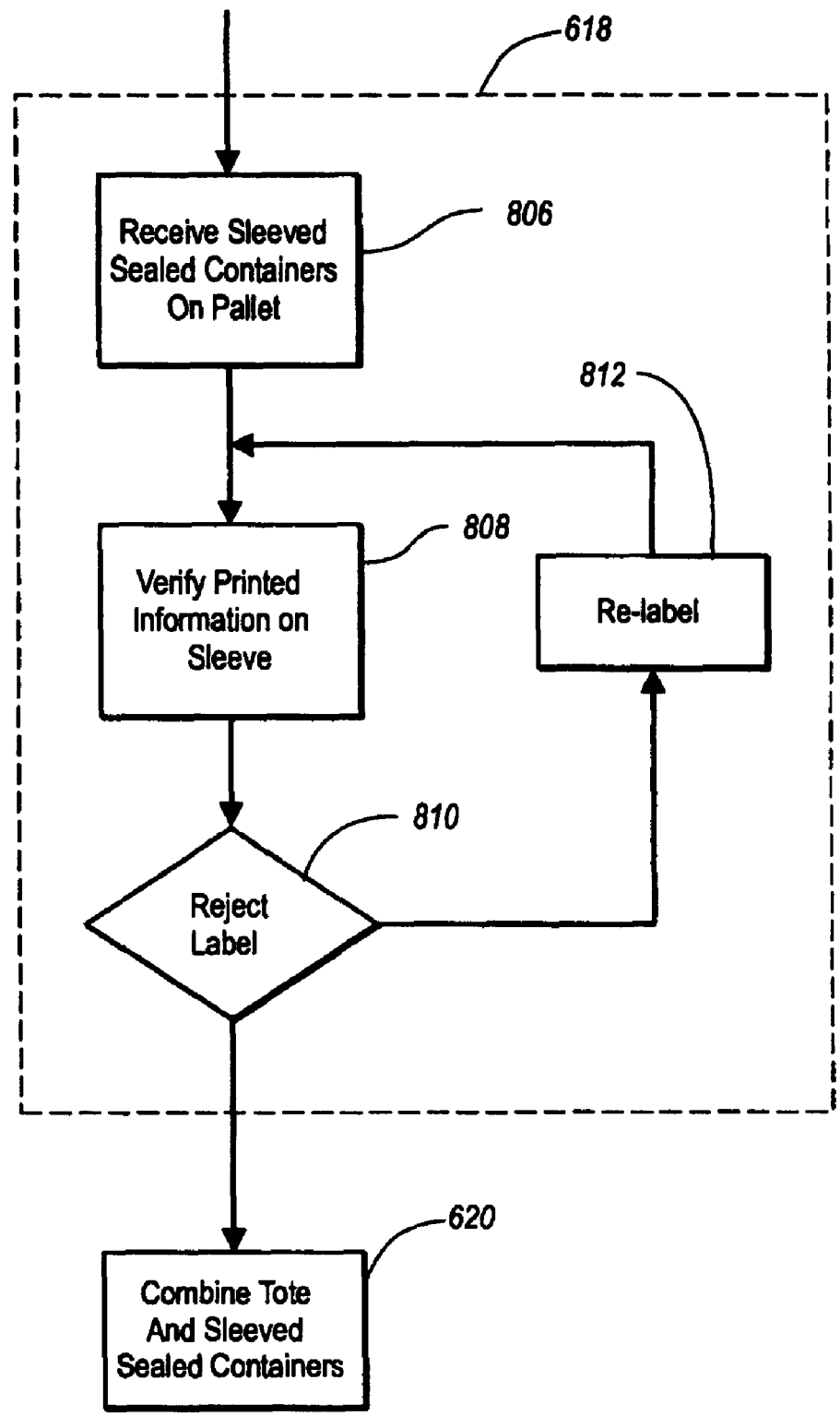

Refer to FIG. 39 there is shown a more detailed flowchart of the inspection of the sleeved containers conducted at block 618. This inspection at block 618 is performed after the multiple prescription container has been sealed. The need for this second inspection is to maintain a high degree of quality assurance and quality control (QA/QC). For example, a tablet or medication may have fallen out of the multiple prescription container during the lid sealing process described above. Additionally, the wrong printed information may have been placed on the lidstock, sleeve, or cap. In the illustrative production facility embodiment, the sleeved sealed containers are received in block 806. At block 808, the printed information on the sleeve and/or lid is verified. If the label is incorrect then the label is rejected at decision diamond 810, and a new label is placed on the sleeve 812. If the label is accurate, then the method proceeds to block 620 where tote printed materials are combined with the sleeved multiple prescription containers.

Note, that other problems that may also be identified during the inspection process 618 include identifying tablets or medication being broken, compromised, or too many tablets being dispensed at one particular time. Additionally, the inspection may not be limited to simply checking the label, and a more exhaustive secondary inspection may be conducted using a variety of different instruments including, but not limited to, robotic inspections at a visual wavelength, near IR, X-ray, precision weighing and any other detection means that can identify the type of tablets or medication in each container.

Referring to FIG. 40 there is shown an exploded perspective view of the illustrative tabletop system with the lid assembly process, sleeve assembly process, and inspection. The illustrative table top system includes generating a lid at station 670, and sealing the lid at station 672. The container travels along conveyor 665. The sleeve located at sleeve dispenser 674 is then applied. The sleeve label is generated at sleeve label station 675. The pharmacist then proceeds to combine the sleeve and the sealed multiple prescription container. The pharmacist then may perform a visual inspection. Printed materials are generated by printer 676, and the printed materials are combined with the multiple prescription container assembly.

Referring to FIG. 41 there is shown a block diagram of the tote assembly system 622 that controls the printed materials. Prior to generating the printed materials the illustrative tote assembly system performs an order consolidation process 820. The order consolidation process comprises accessing a database with patient prescriptions and orders and consolidating various prescriptions or orders. For example, a patient may request vitamin supplements with prescribed medications, and so order consolidation may be necessary. Additionally, there may be two separate prescriptions from two different doctors that need to be combined. The method then proceeds to block 822 where the patient-specific information is printed. This patient-specific information may include the labels described above in FIGS. 5-7 above. At block 824, prescription literature that is provided by a pharmaceutical company, medical provider, insurance company, or other such health professional may be included. These printed materials may be generated at the production facility or may be shipped to the production facility or any combination thereof. In the illustrative tote assembly system, shipper packaging information may also be processed at block 826, so that the illustrative production facility may accommodate shipping using a variety of different carriers, e.g. FedEx, UPS, USPS, DHL, etc. The appropriate shipping label is then generated at block 828. The method then proceeds to block 620 where the sleeved sealed container(s) are combined with printed materials in the tote or pallet.

Referring to FIG. 42 there is shown a block diagram describing the combining of the tote and sealed multiple prescription containers at block 620. At block 830, the illustrative production facility conveys the pallet or tote with the multiple prescription container assembly. At block 832, the multiple prescription container assembly is then combined with the printed materials generated by the tote assembly system 622. After the prescription order is filled, a record of the filled prescription is recorded and communicated to the appropriate entities as represented by block 834. The multiple prescription container assembly and associated materials are then shipped to the pharmacy or customer as reflected by block 624.

Referring to FIG. 43 there is shown a perspective view of an illustrative sealed outer box or final package for an alternative packaging assembly and apparatus. In this alternative package, the illustrative sealed outer box or "final package" 910 comprises a lid 912 that is coupled to the back sidewall (not shown) of the outer box 910. The remaining sidewalls 914 abut the lid 912. An illustrative label 916 seals the outer box 910 by coupling the lid 912 with a front sidewall. The label 916 includes a plurality of information such as the patient name 918, e.g. Mary M. Additionally, the label may include an illustrative dosing interval 920, e.g. A.M. (morning intervals for taking the medications), and additional information 922 about the different medications within the outer box 910. The additional information 922 may include the type of prescriptions within the box, a serial number associated with the patient, the prescribing physician, the pharmacy that filled the prescription, the dosage period, a bar code, or any other such information that may be placed on the label. To open the outer box 910, a patient or caregiver simply breaks the label 916 to access the components within the outer box 910.

The final package 910 comprises a plurality of primary packages as described below. Additionally, the final package may comprise package inserts and PRN medications as described in further detail below.

Referring to FIG. 44 there is shown the opened final package of FIG. 43, and a plurality of sealed containers or "primary packages" within the outer box 910. The illustrative final package 910 provides medications for the 28-day dosing period. Within the illustrative outer box 910 there are four primary packages 930, 932, 934, and 936. The size of each primary package depends on the quantity and type of tablets held by each container. Each primary package is initially sealed, and provides medications for a 7-day dosing period. Each primary package comprises a plurality of primary packages e.g. pouches and a container that houses the preliminary packages. Additionally, the container is configured to receive labeling information as described herein.

The first primary package 930 is shown after having been taken out of the final package 910. The container 930 comprises an illustrative label 938 that provides information such as the patient name 940, e.g. Mary M, the dosing interval 942, and additional information 944, e.g. "week 1" dosing period. Furthermore, the additional information 944 may include the type of prescriptions within the container, a serial number associated with the patient, the prescribing physician, the pharmacy that filled the prescription, the dosage period, or any other such information that may be placed on the label. The first primary container 930 is initially sealed and has a front face 946, which can be torn open by lifting the bottom lip 948, and tearing the front face along the perforations 950. The illustrative front face also comprises a plurality of tear-off tabs 952 or removable elements, e.g. circular perforations, for each day of the week during the 7-day dosing period, in which the tear-off tabs are seen through a cut-out. Additional labels or printed materials can also be provided on the front face 946, such as "warning" information, or emergency contact information, or any other text based or Braille information. Those of ordinary skill in the art shall appreciate that the description of the illustrative first primary package 930 also applies to the remaining containers 932, 934, and 936.

Referring to FIG. 45 there is shown a perspective view of an opened primary package housing a plurality of pouches or "preliminary packages." In the illustrative embodiment, the opened container 930 is opened by lifting the bottom lip 948 and tearing the front face along the perforations resulting in perforated edges 956 on the front face of the container 930. The resulting container lid 958 is fixedly coupled to the back sidewall of the container. The container lid 958 comprises an opening or cutout 960 that serves as a window to view the tear-off tabs 952.

Within the container 930 are a plurality of pouches 962a through 962g, e.g. a seven-day supply of medications. An illustrative preliminary package 962a is lifted from the container. The illustrative pouch 962a comprises a plurality of printed text that may include the patient's name 964, a number of pouches 966 that are to be consumed, a date and time 968 associated with consuming the contents within the packet, tablet information 970 such as name of the particular prescribed medications, dosage concentration, lot number, and other such information. Additionally, an expiration date 972 is provided. In the illustrative example, the pouch is transparent and the medications within the pouch are visible for a variety of reasons including QA/QC.

After the preliminary package is consumed, the patient or caregiver may remove one of the applicable tear-off tabs 952. By way of example and not of limitation, the date that the pouch is consumed is Sep. 21, 2006, which falls on Thursday. The patient or caregiver may remove the Thursday tab 976 so that the patient or caregiver can quickly determine that the medications were taken on specific prescribed days. After consuming the medication in the packet 962a, the container 930 is closed by putting the bottom lip 948 of the container lid 958 into the slot 978 on the front face of container 930. The primary package may also contain additional labeling information on the underside of the container lid 958 as shown in FIG. 50A, which is described in further detail below.

Referring to FIG. 46A there is shown an exploded view of the illustrative sealed preliminary package 962a comprising a plurality of tablets associated with different medications. The preliminary package provides a more detailed view of the transparent pouch or packet having a plurality of tablets associated with different medications. The labeling or printing on the pouch 962a is similar to the labeling shown in FIG. 45, and comprises printed text that may include the patient's name 964, a number of pouches 966 that are to be consumed during a particular dosing interval, a date and time 968 associated with consuming the contents within the preliminary package, e.g. pouch. The illustrative tablet information 970 includes the name of particular prescribed medications, the generic or trademarked name, manufacturer, the concentration associated with the tablet, the lot number, and other such information that is associated with the tablets or medications. For medications that must be consumed within a particular period of time, an "expiration" date 972 may also be provided. Furthermore, contact information 980 may also be provided, so that additional information associated with the tablets or medications can be obtained. For example, an order may have to be refilled so pharmacy information may also be located on the pouch.

Referring to FIG. 46B there is shown an additional label that is associated with illustrative primary package in FIG. 46A. The additional label 982 may be an empty pouch that has additional information that could not be printed on the pouch 962*a*. The additional information may include a bar code 984 for tracking the medications within the pouch. Other information such as the dispensing pharmacy 986 may also be provided. Furthermore, additional medical information may also be provided such as side effects and warnings associated with the tablets may be provided on the label 982.

Referring to FIG. 47 there is shown a perspective view of the opened primary package being placed back into the final package. The primary package may easily be removed from the final package and is readily accessible. Additional labeling may be added to primary package and final package to accommodate the need of individuals having special needs, handicaps, reduced mental capacity, blindness, or other such disability including but not limited to arthritis.

Referring to FIG. 48, there is shown a flowchart that describes the method for accessing a plurality of different medications described above. The method is initiated at block 1002 when the final package is opened. Within the final package is the plurality of primary packages. Additionally, the final package may house package inserts and PRN medications. At block 1004, the appropriate primary package is selected. Appropriate labeling of the primary package indicates which container should be selected. The correct primary package or container is opened at block 1006. The primary package comprises a container and a plurality of preliminary packages, e.g. pouches, and the required labeling. The preliminary package may also comprise one or more package inserts. Before (or after) taking the medication in the illustrative pouch, the patient or caregiver has the option of removing a reminder tear-off tab 952 shown in FIG. 45. At block 1010, the patient consumes or takes the medication in the multi-prescription pouch. After consuming the medication, the method proceeds to block 1012 where the patient closes the container, and waits until the next time interval or period for taking the prescribed medication, vitamins, supplements, or any combination thereof. At decision diamond 1014, the determination is made whether to take the next preliminary package having a plurality of different medications. If it is time to take the next does, the method proceeds to decision diamond 1016 where the availability of the next multi-prescription package is made by the patient or the caregiver. If the preliminary package or pouch is available, then the method proceeds to either block 1008 or 1006 depending on the status of the primary package, i.e. open or closed. If the next pouch is not available or the preliminary packages are running low, a refill is requested at block 1018. Those skilled in the art shall appreciate that various design parameters, requirement, ruling, orders, and statutes may affect the precise method employed. The general principles for using the final package, the primary package, and the preliminary package have been disclosed.

Referring to FIG. 49A through FIG. 49C there is shown an illustrative flowchart for the assembly of the final package, the primary package and a multiple prescription package. A multiple prescription package refers to a package that combines a plurality of different medications into a single package. A multiple prescription package is also referred to as a primary package, and the terms are used interchangeably throughout this specification. A multiple prescription order is required to generate a multiple prescription package. A multiple prescription package or "primary package" comprises a preliminary package. The preliminary package may be a pouch, a cup, a matchbook, a blister pack, or any other similar packaging means that can hold a plurality of different medications. The multiple prescription package or primary package also comprises a container configured to hold a plurality of preliminary packages, which hold a plurality of different medications. In one embodiment, the multiple prescription package or primary package is combined with package inserts, and possibly PRN medications to produce a "final package." The final package is ready for pick-up of shipping.

A multiple prescription order or a plurality of single prescription orders are required to produce a primary package. A multiple prescription order comprises a plurality of medications that are different from one another. Additionally, the multiple prescription order may indicate the frequency with which the medications are to be consumed. Furthermore, the prescription may indicate the particular time interval that each medication should be taken, i.e. morning, noon, evening, and bedtime.

The description provided herein describes systems, apparatus, labeling techniques, and methods that can be used to take a preliminary package and convert this to a multiple prescription package or primary package, which can then be integrated with package inserts to produce a final package that is ready for pick-up or delivery. A method for assembling the multiple prescription package that can be easily transported and administered is also described. The final package is properly validated to assure that the appropriate medications are in the primary package. Additionally, the final package accommodates package inserts. Furthermore, a method for verifying the prescription, the preliminary package, and the primary package is described.

The illustrative flowchart is initiated in FIG. 49A at block 1102 where a multiple prescription order is received from a customer. After receiving the prescription order, a technician may proceed to input the customer information into a graphical user interface (GUI) for a pharmacy management program such as PharmaServ, which is a pharmacy management system available by McKesson. The Pharmaserv pharmacy management system performs operations including prescription processing, claims adjudication, inventory management, and integration with automation and workflow. Additionally, the technician may also scan the prescription order to generate a digitized copy of the prescription order.

In one embodiment, after inputting the customer information into the pharmacy management system, the pharmacy management system performs the claims adjudication process and generates a hard copy of the prescription, and prints out any notes received from the patient. A variety of labels may be printed separately using a personal computer and printer. The illustrative labels may be conventional labels having an adhesive backing affixed to wax paper. The illustrative labels may also be fastened using other methods such as stapling, taping, or other such fastening means. The thickness of the illustrative labels also varies. In another embodiment, the prescription, labels and notes are associated with a particular bar code or other identification means, e.g. RFID that is associated with the prescription order. The hard copy of the prescription, the plurality of labels, and any notes are placed into a tote. The process of producing a tote having the labels, prescription, and bar code is shown at block 1104.

In the illustrative flowchart, the pharmacist proceeds to block 1106 where the pharmacist reviews the patient history, the prescriptions, and the notes associated with the patient. In the illustrative embodiment, the pharmacist keys in the patient information from the hard copy of the prescription that is within the tote into the pharmacy management program. Additionally, the patient history that is stored in the pharmacy management program is reviewed by the pharmacist. Furthermore, the pharmacist verifies each new prescription or existing prescription associated with the patient. Further still, the pharmacist checks to see if there are any patient notes that require taking action.

After reviewing the prescription, patient history and notes associated with the patient, the prescription and labels are verified by the pharmacist at block 1108. The verification process may comprise determining that the patients name and date of birth are correct on each label and that the correct date has been provided. Additionally, the drug strength, quantity, and refill status may be checked. The pharmacist may also determine whether the medical professional prescribing the medication is correct and has provided a valid signature. Furthermore, in the illustrative embodiment, the pharmacist may proceed to determine whether a "dispense as written" (DAW) designation is correct. The DAW designation limits the pharmacist to dispensing a prescription according to a specific provision authorized by the patient's health plan. If the prescription and labels can not be properly verified, the pharmacist will attempt to correct the error. However, if any error identified in the verification process can not be corrected, the prescription and labels are rejected.

In another embodiment, an additional bar code or other identification means is used to track and verify the prescription and labels. The illustrative bar code or other identification means may be associated with the name of the patient, the patient's date of birth, the prescription, the drugs or medications, the drug strength, the quantity, the refill status, the medical professional prescribing the medication, the DAW designation, or any combination thereof.

The verification of the labels is not a trivial process. Referring now to FIG. 50A and FIG. 50B, there is shown two illustrative labels 1200 and 1201 that may be placed on an illustrative container that receives a plurality of filled multiple prescription order. By way of example and not of limitation, the labels may show: the date 1202; the patient's name and address 1204; the name of the prescribing physician 1205; the prescription serial number of the practitioner who filled the prescription (not shown); the prescription number 1206; the proprietary or generic name of the drug or medicine 1208 as written by the prescribing physician; the concentration 1210 of the associated drug; the number of dosage units; specific directions for use given by the prescribing practitioner; the expiration date of the effectiveness of the drug or medicine that is dispensed; the strength of the drug or medicine; the appropriate label warnings; the number of refills 1212; expiration date for refills 1214; substitutions 1216; the lot number 1218; identification means such as a bar code 1220; the interval 1222 for consuming medication, e.g. morning, noon, afternoon, or bedtime; or any combination thereof. Additionally, the label may include a bar code and a date that can be used for tracking and verification purposes.

In the illustrative embodiment the label 1200 is applied to the inside cover 980 of the illustrative primary package 930 described above in FIG. 45. The second label 1201 is applied to the top surface of the primary package 930.

Returning back to FIG. 49A, after the pharmacist verifies the prescription and label at block 1108, the pharmacist indicates that the prescription has been validated in block 1109. To indicate that the prescription has been verified and accepted, a label from the tote is affixed the back of the prescription hard copy. The pharmacist then proceeds to initial the hard copy of each prescription, which is returned to the tote for later inspection.

The verified prescription is then released and is forwarded to the filling system as represented by block 1110. By way of example and not of limitation, the filling system is a McKesson PACMED high-speed packager. The illustrative filling system is configured to generate a preliminary package, which is a pouch having a plurality of different medications. For purposes of this description the terms preliminary package and pouch are used interchangeably. Alternative filling systems as described above may also be used. Each pouch may receive a bar code, medication data, patient data and order data on the exterior of the pouch. Additionally, the illustrative filling system may be configured to apply the bar-code for pouch packaging purposes during the filling process. The output pouches generated by the filling system are then placed in the tote having the labels described above.

The method then proceeds to block 1112 shown in FIG. 49B, where an inspection of the illustrative filled pouches and the associated labels that are in the tote is initiated. The inspection of the pouches is initiated at block 114 and comprises verifying or checking the patient's name on the pouches, and checking that the name on the pouches matches the name on the labels, and matches the hard copy of the prescription. In the additional embodiment, the bar code or identification means may also be scanned to verify that the correct pouches and labels are associated with the correct prescription.

If the patient's name matches, a visual inspection of each pouch may be performed. In the illustrative embodiment, the preliminary package or pouches are transparent and the visual inspection may include validating that the correct quantity of tablets is in the pouch as shown in block 1116. The inspection may then proceed to block 1118 where the color and shape of the tablets are also visually inspected. The visual inspection may then proceed to block 1120 where the tablet ID printed on the pouch is compared to the tablet ID on the tablet itself. At block 1122, the inspection process may also comprise verifying the concentration or dosage of each tablet within the pouch by checking the markings on the table. Thus, the correct quantity of tablets is verified, the type of medications within the pouch is verified, and the concentration or dosage is also verified.

The pharmacist may then proceed to block 1124 where each hard copy of the prescriptions is initialed by the registered pharmacist. The initialed or signed hard copy is filed and retained for at least two years. The tote having the preliminary packages and labels then proceeds to a boxing station.

At block 1126, the tote having the labels and preliminary packages are received at the boxing station, and the labels are applied to one or more boxes. Additionally, the appropriate labels are also attached to the shipping container. At a minimum, the labeling that is applied to both the pouches and the container will need to comply with regulatory requirements for that particular jurisdiction. Although each pouch has a surface that can receive written text, the size of the pouch limits the available area for receiving text. Therefore, to comply with regulatory requirements additional information beyond that which can be placed on each pouch may be required. This additional information can be applied on another label, such as label 1200 described above. Label 1200 may then be applied to an illustrative container that is similar to the containers described above. The label may be placed on the inside cover of the illustrative container.

In another illustrative embodiment, another corresponding label is also applied to each of the pouches having the different medications. This additional labeling may be required to comply with regulatory labeling requirements. Furthermore, the additional labeling may be used to for a particular patient group that may have special requirements. For example, the pouches may have to be adapted for usage by arthritic patients, blind patients, or other patients having special needs.

For example, for an arthritic patient group, the pouches may be quite difficult to open, and so the additional corresponding label is applied to the preliminary package to ease the process of opening the pouch. This additional label may be composed of a stiff paper backing and may have a notch with perforations to ease the tearing of the label and the underlying pouch material. For a blind patient group, the blind patients may be unable to distinguish one pouch from another, or be unable to tell when to consume the appropriate medications. Thus, the labeling for a blind patient group may require the use of Braille lettering or other encoding schemes that would allow a blind person to distinguish between preliminary packages or pouches and intervals for consuming their medication.

At block 1128, the preliminary packages are loaded into the outer box or boxes to create a "primary package." The primary package complies with the regulatory labeling and distribution requirements. In the illustrative example, the primary package comprises a plurality of pouches that are placed within a container. By way of example and not of limitation, there may be a seven-day supply of medications within each container. The container is configured to accommodate a seven-day supply of medication. In another embodiment, a container may be configured to accommodate a 28-day supply of medication. As described previously, the container is also configured to receive a label that indicates the time of day or interval during which the medications within the pouch are to be consumed, e.g. morning, noon, evening, or bedtime.

At block 1130, the primary package is sealed or glued. The illustrative primary package comprises a plurality of preliminary packages and a container. For the illustrative primary package there is a label on the exterior of the container that indicates the name of the patient and the interval when the patient should consume the medication, e.g. AM or morning. After sealing the primary package, the primary package is inspected to ensure that the appropriate labeling information is on the exterior of the primary package. In the additional illustrative embodiment, the bar code on the container may be recorded and a database may be used to track that the container has been sealed. The inspection comprises making sure that the necessary label information is on the outside of the package.

At block 1132, the package insert or inserts (PIS) are prepared for the multiple prescription order. The package inserts have detailed information about indications, warnings, precautions, side effects, dosage, administration, and clinical pharmacology. The package inserts may also include summaries of the various medications being taken, and summaries of the side effects, and the associated administration. Although the package inserts are written primarily for a physician and pharmacist, the package inserts may be simplified so that they are easier to understand. In the illustrative embodiment, the package insert is associated with the primary package and put into the final package, as described in block 1134. The package insert is configured to be distinguishable from other package inserts associated with another patient. Thus, the package insert is associated with all the medications in the primary package. The package insert may also comprise a variety of different identification means such as the name of the patient, a bar code or any other such identification means. In the additional embodiment, the package insert is also configured to comprise a bar code to ensure that the correct package insert is associated with the corresponding prescription. Alternatively, the package insert may be combined with the primary package so that the primary package comprises a plurality of pouches, the package insert, and the outer box. The package insert should not be confused with the labels that are applied to either the container or to the pouches themselves.

At block 1136, the PRN prescription is filled. In a majority of cases, PRN prescriptions will not be filled, however, PRN prescriptions do account for a substantial number of prescription orders. PRN prescriptions are consumed on an as needed basis. The acronym PRN refers to dosage of prescribed medication that is not scheduled and for which administration is left to the caregiver or the patient's prerogative. PRN is the acronym for "pro re nata" that is commonly used to mean "as needed." Most often PRN medications are analgesics such as Tylenol®, laxatives, sleeping aids, and similar medications. In the additional embodiment, the bar code described previously may also be associated with the PRN prescription.

At block 1138, the final package is assembled. The final package comprises the primary package and the package inserts. In certain instances the final package also comprises the PRN medications. The final package may also require shipping labels or other such labels indicating that the final package is ready for pick-up.

The method then proceeds to block 1140 where the final package is validated. The final package validation may include checking the events associated with the assembly of the final package. Therefore, the validation process may comprise checking to see if a pharmacist reviewed the prescription and labels, confirming that each pouch was checked after being filled, checking the method used to confirm the correct medications were in the pouch, confirming that a pharmacist had initialed the prescription after the prescription was filled, confirming that each tote has no labels, confirming that each container was sealed, checking to see that a PIS was generated, and that the PRN was filled, or any combination thereof. Thus, the validation process evaluates each of the process steps and determines whether or not each process step was performed. In the additional embodiment that comprises the bar code, the scanning or identification of the bar code at each process step may be required. After the final package is validated, the final package is released and is ready for pick-up or shipping.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A method for verifying a filled prescription order for a plurality of different medications, said method comprising:

enabling a pharmacy management system to receive a digitized copy of a prescription order;

generating a verified multiple prescription order at the pharmacy management system, wherein the verified multiple prescription order is associated with a particular patient, the verified multiple prescription order comprising a plurality of medications including a first medication that is different from a second medication, wherein the first medication and second medication are configured to be taken by the patient at a same time;

generating a patient bar code associated with the particular patient, said patient bar code comprising of patient information such as patient's name, patient's address or patient's date of birth;

producing a plurality of labels with a printer coupled to a computer, the labels associated with the prescription order;

validating the plurality of labels by comparing the labels to the multiple prescription order;

generating a multiple prescription order label bar code disposed on at least one label that is associated with the multiple prescription order, said multiple prescription order label bar code comprising of prescription information such as types of medications in the order, amounts of medication or dosage information;

receiving the verified multiple prescription order at a filling system;

generating a plurality of packages at the filling system, the plurality of packages configured to hold the first medication and the second medication in each package of the plurality of packages;

counting a number of medications dispensed in each package with a sensor after the medications have been dispensed;

generating a package bar code that is associated with at least one of the plurality of packages;

applying one of the labels and at least one of the bar codes to at least one secondary package configured for dispensing the packages;

placing the packages into the secondary package; and scanning each of the bar codes to verify that the correct plurality of packages, the secondary package and labels are associated with the correct prescription.

2. The method of claim 1 further comprising labeling the secondary package to indicate a same time for consuming the medications.

3. The method of claim 2 wherein the same time for consuming the medications is selected from the group consisting of: morning, noon, evening, bedtime, AM and PM.

4. The method of claim 1 further comprising verifying a tablet ID.

5. A system for verifying a filled prescription order for a plurality of different medications, comprising:

a pharmacy management system configured to receive and verify a digitized copy of a prescription order to produce a verified multiple prescription order that is associated with a particular patient, the verified multiple prescription order having a first medication that is different from a second medication, wherein the first medication and second medication are to be taken by the patient at a same time, the pharmacy management system further comprising:

a patient bar code associated with the particular patient, said patient bar code comprising of patient information such as patient's name, patient's address or patient's date of birth;

a printer coupled to a computer that is configured to produce a plurality of labels associated with the verified multiple prescription order, the labels validated by comparison to the multiple prescription order;

a multiple prescription order label bar code disposed on at least one label associated with the verified multiple prescription order said multiple prescription order label bar code comprising of prescription information such as types of medications in the order, amounts of medication or dosage information;

a filling system that receives the verified multiple prescription order from the pharmacy management system, the filling system includes, a plurality of packages configured to receive the first medication and the second medication in each package of the plurality of packages, a sensor configured to count a number of medications dispensed in each package after the medications have been dispensed;

a package bar code associated with at least one of the plurality of packages, at least one secondary package configured to dispense the plurality of packages, the at least one-secondary package having one of the labels applied; and a means for scanning each package bar code to verify that the correct plurality of packages, the secondary package and labels are associated with a correctly filled verified multiple prescription order.

6. The system of claim 5 wherein the at least one secondary package includes a label indicating a same time for consuming the medications.

7. The system of claim 6 wherein the same time for consuming the medications is selected from the group consisting of: morning, noon, evening, bedtime, AM and PM.

8. The system of claim 5 further comprising a tablet ID that is verified.

9. A system for verifying a filled prescription order for a plurality of different medications, comprising:

a means for pharmacy management that includes, a digitized copy of a prescription order, a means for receiving a verified multiple prescription order that is associated with a particular patient, the verified multiple prescription order having a first medication that is different from a second medication, wherein the first medication and second medication are configured to be taken by the patient at a same time, a patient bar code associated with the particular patient, said patient bar code comprising of patient information such as patient's name, patient's address or patient's date of birth;

a printer coupled to a computer that is configured to produce a plurality of labels associated with the prescription order, the labels validated by comparison to the multiple prescription order, a multiple prescription order label bar code disposed on at least one label associated with the multiple prescription order, said multiple prescription order label bar code comprising of prescription information such as types of medications in the order, amounts of medication or dosage information;

a filling means that receives the verified multiple prescription order form the pharmacy management means, the filling means includes, a plurality of packages configured to receive the first medication and the second medication in each package of the plurality of packages, a sensor configured to count a number of medications dispensed in each package after the medications have been dispensed;

a package bar code associated with at least one of the plurality of packages, at least one secondary package configured to receive the plurality of packages, the at least one secondary package having one of the labels applied; and a means for scanning each of the bar codes to verify that the correct plurality of packages, the secondary package and labels are associated with the correct prescription.

10. The system of claim 9 wherein the at least one secondary package includes a label indicating a same time for consuming the medications.

11. The system of claim 10 wherein the same time for consuming the medications is selected from the group consisting of: morning, noon, evening, bedtime, AM and PM.

12. The system of claim 9 further comprising a tablet ID that is verified.

* * * * *